(12) United States Patent
Krause et al.

(10) Patent No.: US 10,596,168 B2
(45) Date of Patent: Mar. 24, 2020

(54) ANTAGONISTS OF THE THYROID-STIMULATING HORMONE RECEPTOR (TSHR)

(71) Applicant: Forschungsverbund Berlin e.V., Berlin (DE)

(72) Inventors: Gerd Krause, Berlin (DE); Inna Hoyer, Panketal (DE); Edgar Specker, Berlin (DE); Jens Furkert, Glienicke (DE); Patrick Marcinkowski, Berlin (DE); Jens-Peter Von Kries, Panketal (DE); Martin Neuenschwander, Berlin (DE); Marc Nazare, Berlin (DE)

(73) Assignee: Forschungsverbund Berlin e.V., Berlin (DE)

(*) Notice: Subject to any disclaimer, the term of this patent is extended or adjusted under 35 U.S.C. 154(b) by 0 days.

(21) Appl. No.: 16/096,868

(22) PCT Filed: Apr. 26, 2017

(86) PCT No.: PCT/EP2017/059930
§ 371 (c)(1),
(2) Date: Oct. 26, 2018

(87) PCT Pub. No.: WO2017/186793
PCT Pub. Date: Nov. 2, 2017

(65) Prior Publication Data
US 2019/0134024 A1 May 9, 2019

(30) Foreign Application Priority Data
Apr. 27, 2016 (EP) ..................................... 16167304

(51) Int. Cl.
*A61K 31/429* (2006.01)
*A61K 31/495* (2006.01)
(Continued)

(52) U.S. Cl.
CPC .......... *A61K 31/495* (2013.01); *A61K 31/429* (2013.01); *A61P 5/14* (2018.01); *A61P 35/00* (2018.01)

(58) Field of Classification Search
CPC .............. A61K 31/495; A61K 31/4015; A61K 31/403; A61P 5/14
(Continued)

(56) References Cited

U.S. PATENT DOCUMENTS 7,655,688 B2 * 2/2010 Salvati ................. A61K 31/403
514/307

FOREIGN PATENT DOCUMENTS

WO WO 02/067939 A1 9/2002

OTHER PUBLICATIONS

Schapira et al, PNAS (2003), vol. 100 (2), pp. 7354-7359. (Year: 2003).*
(Continued)

*Primary Examiner* — Craig D Ricci
*Assistant Examiner* — Janet L. Coppins
(74) *Attorney, Agent, or Firm* — Knobbe, Martens, Olson & Bear, LLP

(57) ABSTRACT

Chemical compounds are useful in the treatment of a subject afflicted by a thyroid disease. The compounds exhibit activity as thyroid-stimulating hormone receptor (TSHR) antagonists and can be used in the treatment of hyperthyroidism, Graves' disease, Graves' Ophthalmopathy and thyroid cancer.

19 Claims, 11 Drawing Sheets

(51) Int. Cl.
*A61P 5/14* (2006.01)
*A61P 35/00* (2006.01)

(58) Field of Classification Search
USPC .................................................. 514/252.12
See application file for complete search history.

(56) References Cited

OTHER PUBLICATIONS

Atamanyuk, et al. 2008 "Synthesis and anticancer activity of novel thiopyrano [2, 3- d] thiazole-based compounds containing norbornane moiety" *Journal of Sulfur Chemistry* 29(2): 151-162.

Lesyk, et al. 2011 "Thiazolidinone motif in anticancer drug discovery. Experience of DH LNMU medicinal chemistry scientific group." *Biopolymers and Cell* 27(2): 107-117.

* cited by examiner

A

B

C

D

E

A

B

A

B

C

D

ANTAGONISTS OF THE THYROID-STIMULATING HORMONE RECEPTOR (TSHR)

The invention relates to chemical compounds that are useful in the treatment of a subject afflicted by a thyroid disease, in particular to compounds that exhibit activity as thyroid-stimulating hormone receptor (TSHR) antagonists and their use in the treatment of hyperthyroidism, Graves' disease, Graves' Ophthalmopathy and thyroid cancer.

BACKGROUND OF THE INVENTION

About 40% of hyperthyroidism patients suffer from Graves' disease (Morbus Basedow), an autoimmune disease in which autoantibodies activate the thyrotropin receptor, mimicking its natural hormone ligand, the thyroid-stimulating hormone (TSH). This pathological activation of TSH-Receptor (TSHR) leads to uncontrolled production of thyroid hormones causing hyperthyroidism. TSH and the TSHR are key proteins in the control of thyroid function. In fact, TSHR is mainly expressed in follicular epithelial cells of the thyroid gland, but also in a variety of additional cell types such as retro-orbital fibroblasts, kidney, adipocytes and bone cells. TSH binds to its receptor and leads to the stimulation of second messenger pathways involving predominantly cAMP. Inositol 1,4,5-triphosphate ($IP_3$) and diacylglycerol (DAG) pathways are also activated at higher TSH concentrations.

The treatment of choice applied in the clinics for decades involves thyrostatic drugs blocking the production of thyroid hormones (TH). This medication plays a role further downstream in the signal cascade of the thyroid upon activation of the TSHR. Since thyroid hormones $T_3$, $T_4$ are secreted in the thyroid gland and these medications induce an inhibition of their synthesis. Thus, the current primary anti-thyroid treatment does not target the causative molecular activation of the TSHR by antibodies and patients are therefore burdened by a rate of at least 5% adverse effects (Sato et al. 2014). This demands frequent controls of the thyroid hormone levels and adjustments of thyrostatics dosage. In contrast to these drugs, which regulate the thyroid hormone level, the most promising target is the TSHR itself. However, small allosteric antagonists acting directly at the TSHR are not available on the market yet.

Therapeutic Gap for Graves' Ophthalmopathy

Moreover, about 25% of Graves' disease patients also develop an orbitopathy referred to as "Graves' Ophthalmopathy" (GO), a related organ-specific autoimmune disease affecting the appearance and functioning of the eyes. Progression to severe forms occurs rarely, no more than 3% to 6% of cases, however available therapies (Eckstein et al. 2012) are largely imperfect and remain still a dilemma (Bartalena 2011). There is considerable evidence that expression of the TSHR in the orbital fibroblasts (OF) and orbital adipocytes behind the eye may contribute to this difficult-to-treat orbitopathy, and thyroid stimulating antibodies titer tend to correlate with severity of GO. Orbital fibroblast have been recognized as primary target cells of autoimmune attack and TSHR acts as a primary autoantigen in GO. The pathological activation of TSHR leads to the production of the extracellular matrix by involvement of hyaluronan acid (HA), fibrosis and swelling of extraocular muscle as well as adipogenesis of orbital fibroblasts (orbital fat expansion) (Sorisky et al. 1996; Feliciello et al. 1993). The increase in tissue volume in the orbit often causes diplopia and compression of the optic nerve and exophthalmos. Human retroocular fibroblasts have been utilized as in vitro models to study GO.

Apart from glucocorticoids and the IGF-1 receptor, which is also considered as antigen in GO, the TSHR is reckoned to be a potential target for pharmacological intervention of GO which is due to the following facts: TSHR expression is increased with adipogenesis, the TSAb (M22) itself enhances adipogenesis, it has been shown that the TSHR is linked with the HA production, since the M22 stimulated HA synthesis can be inhibited by a $PI_3K$ inhibitor or by an inhibitor of mTOR, and different TRAb induce divergent signaling pathways downstream of the TSHR such as c-Raf-ERK via Gq as unique cascade, which is not activated by TSH, which primarily activates Gs.

Taken together autoimmune autoantibodies are activating TSHR in the orbita as well, but in contrast to the thyroid different molecular mechanisms are activated. Therefore, the anti-thyroid drugs available on the market blocking the thyroid hormone synthesis in the thyroid are non-effective for treatment of thyroid eye disease. This unveils the therapeutic gap for the treatment of severe GO patients in the clinics. This apparent problem has been repeatedly expressed at the annual international congresses of the European Thyroid Association (Bartalena 2013).

Pharmacological Approaches to Tackle Graves' Ophthalmopathy

A potential approach for the therapy of GO could be the suppression of the pathological activation caused by autoantibodies directly on the TSHR by drug like small molecule ligands (SM). Thus orally active small allosteric antagonists have a strong therapeutic potential underlining their therapeutic importance for TSHR-mediated GO. In contrast to the activating autoantibodies that bind like the TSH to the extracellular region of the TSHR, such synthetic SMs preferentially bind elsewhere, for example allosterically into a binding pocket located within the heptahelical transmembrane domain of the receptor (FIG. 1).

Presently some success has been obtained by the application of antibodies that block TSHR activation, which bind similarly to TSH at the extracellular binding site of the TSHR. Crystal structures of activating (M22) and blocking (K1-70) monoclonal antibodies identified the different interacting residues at the extracellular leucine rich repeat domain (LRRD) for both types. Immunomodulation is also considered a feasible approach to tackle GO. However, for example introducing an antibody for immunomodulation as a potential drug will be difficult to produce in large quantities with uniform quality and it is in magnitudes more cost-intensive than small molecules.

Analysis of Allosteric Transmembrane Binding Pocket at TSHR

Together with the lutropin receptor (LHCGR) and follitropin (FSH) receptor (FSHR), the TSHR (Kleinau & Krause 2009) belongs to the subfamily of glycoprotein-hormone receptors (GPHRs) within the rhodopsin/adrenergic receptor family 1 of the GPCR superfamily. A special feature of GPHRs is the very large extracellular portion, where the hormone binds between a leucine rich repeat domain (LRRD) and a hinge region and thereby the activation is initiated (FIG. 11).

For the TSHR the functional and structural dimensions of its extracellular region were defined and an intramolecular agonistic unit was suggested (Kleinau, Mueller, et al. 2011). The signal is then conveyed through the heptahelical transmembrane domain into the cell via the heterotrimeric G-protein. It has been shown that the developed small agonist compound 2 (FIG. 1) is interacting in the transmembrane binding pocket (Neumann et al. 2009). The allosteric binding pocket was investigated in more detail by modelling driven mutagenesis of about 30 mutations. This led to distinct constitutively activating mutations (CAM) by V421I, Y466A, T501A, L587V, M637C, M637W, S641A, Y643F L645V, Y667A (G. Kleinau et al. 2010) and silencing mutations V4241, L467V, Y582A, Y582F, Y643A, L665V (Haas et al. 2011) indicating not only key amino acids covering the allosteric binding pocket at the TSHR but also positions, where the TSHR conformation can be changed to an active or inactive state respectively.

Allosteric Modulators for the GPHRs, Focusing on the TSHR

One low molecular weight agonist for a GPHR, org41841, was reported as selective for the lutropin receptor LHCGR (van Straten et al. 2002). It was shown that org41841 is also a partial agonist for the TSHR and it binds allosterically into a transmembrane binding pocket (Jäschke et al. 2006). The identification and characterization of an additional binding pocket located in the transmembrane domain of GPHRs led to the development of drug like small molecules targeting this family. An antagonistic compound (NIDDK/CEB-52 (c52)) was developed, albeit with low affinity at TSHR, exhibiting no effects at FSHR but partial agonistic activity at LHCGR (G Kleinau et al. 2008).

A high-throughput screen (HTS) for TSHR agonists (Titus et al. 2008) together with structure-functional analyses led to the TSHR agonists described in WO/2010/047674 and the identification of the first nanomolar TSHR selective agonist named 'compound 2', (Neumann et al. 2009). Modifications of compound 2 led to an inverse agonist (S2-7) with micromolar affinity for the TSHR, which inhibits basal signaling at wild type and at four constitutively active mutants of TSHR (Neumann et al. 2010). This antagonistic compound was also tested on orbital fibroblasts involved in pathogenesis of GO (Turcu et al. 2013) and in mice (Neumann et al. 2014). However, one has to note that this compound exhibits a cross-reactivity towards the FSHR.

The tetrahydroquinoline compound Org274179-0, was reported as a nanomolar TSHR antagonist (van Koppen et al. 2012), but exhibits cross-reactivity for the FSHR and LHCGR as well. This fact is not surprising as the tetrahydroquinoline scaffold is a derivative of the strong FSHR antagonist previously developed by the former company Organon (van Straten et al. 2005). For this reason therapeutical application of this substance type is disadvantageous, since the side effects by blocking the FSHR activation, resulting for example in reduced spermatogenesis in men, would be unfavorable. Taken together, according to the best knowledge of the inventors there is no TSHR antagonist described previously in clinical use, and only two other small molecules with antagonistic effects at TSHR (S2-7, Org274179-0) have been published, but both with cross reactivity to FSHR, albeit with different strengths.

Chemical compounds with nuclear hormone modulatory function have been disclosed in the art. WO 2002/067939 discloses fused cyclic succinimide compounds and analogs thereof as modulators of nuclear hormone receptor function, in particular as modulators of the androgen receptor (AR), the estrogen receptor (ER), the progesterone receptor (PR), the glucocorticoid receptor (GR), the mineralocorticoid receptor (MR), the aldosterone receptor (ALDR) and the steroid and xenobiotic receptor (SXR), potentially for use in the treatment of autoimmune thyroiditis. No disclosure is evident that such compounds exhibit a TSHR antagonistic activity suitable in treating hyperthyroidism.

Atamanyuk et al. (Journal of Sulfur Chemistry, 2008, 29:2, p 151-162) disclose an anti-cancer activity of thiopyrano(2,3-d)thiazole-based compounds containing a norbornane moiety. Lesyk et al. (Biopolimery I Kletka, 2011, 27:2, p 107-111) disclose 4-thiazolidinones and related heterocyclic compounds and their anti-cancer activity. No mention is made in either document of a TSHR antagonistic activity of such compounds that would be suitable in treating hyperthyroidism.

In light of the prior art there remains a significant need in the art to provide additional means for the treatment of hyperthyroidism, in particular for providing compounds that act as TSHR antagonists.

SUMMARY OF THE INVENTION

In light of the prior art the technical problem underlying the present invention is to provide alternative and/or improved means for the treatment of thyroid disease, in particular TSHR antagonists for the treatment of hyperthyroidism. A further objective of the invention may be considered providing compounds with an activity specific to the TSHR, preferably with reduced cross-reactivity to the FSHR compared to those compounds described in the art.

This problem is solved by the features of the independent claims. Preferred embodiments of the present invention are provided by the dependent claims.

The invention therefore relates to a compound according to Formula I (embodiment a) for use in the treatment of a subject afflicted by a hyperthyroidism,

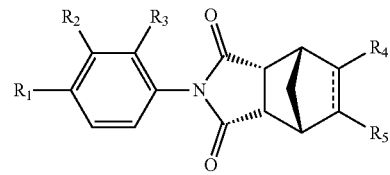

Formula I wherein
$R_1$=H, OH, alkyl, alkoxy, carbonyl, alkoxycarbonyl, $NH_2$, halogen, an optionally substituted 6-member ring, preferably an aryl group, such as phenyl, wherein said optional substituent is selected from the group consisting of OH, alkyl, alkoxy, carbonyl, alkoxycarbonyl, $NO_2$, amine, halogen, $CX_3$, wherein X is a halogen, or wherein

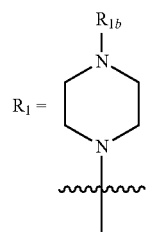

wherein $R_{1b}$=alkyl, an optionally substituted 6-member ring, preferably an aryl group, such as phenyl, wherein said optional substituent is selected from the group consisting of OH, alkyl, alkoxy, carbonyl, alkoxycarbonyl, $NO_2$, amine, halogen, $CX_3$, wherein X is a halogen;

$R_2$=H, OH, alkyl, alkoxy, carbonyl, alkoxycarbonyl, $NO_2$, amine, aminocarbonyl;

$R_3$=H, OH, alkyl, alkoxy, carbonyl, alkoxycarbonyl, halogen;

$R_4$, $R_5$=H, alkyl, alkoxy, carbonyl, alkoxycarbonyl, wherein $R_4$ and $R_5$ can be the same or different, or wherein $R_4$ and $R_5$=

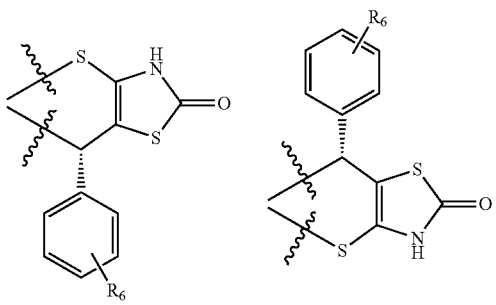

wherein $R_6$=H, OH, alkyl, alkoxy, carbonyl, alkoxycarbonyl, $NO_2$, amine, aminocarbonyl, halogen, $CX_3$, wherein X is a halogen.

It was entirely surprising that the compounds comprising a structure of formula I exhibit TSHR antagonist activities. In particular, the stereoisomeric configuration of the norbonene/norbornane moiety positioned adjacently to the di-substituted thiazolone ring enables TSHR antagonism, and potentially high specificity.

As is shown in more detail below, the stereoisomers S37 and S36, as specific isomers of S4, falling under formulae I and II, constitute a special form of diastereoisomerism. They are endo- and exo-isomers to each other, whereby only S37, comprising the stereoisomeric configuration of formula I and II, shows the desired activity, and S36 is inactive. FIG. 3 provides illustration of the structural differences based on the stereoisomerism described herein.

A similar effect is observed between the stereoisomers of S9, falling under formula I and III, as seen (in structurally distinct but similar) in isomers 34 and 35 (refer table 1 below).

The stereoisomerism of the compounds of the present invention therefore provides a distinguishing feature over the prior art, which could not have been expected by a skilled person.

In a preferred embodiment the invention relates to a compound for use in the treatment of a subject afflicted by hyperthyroidism, according to Formula I (embodiment a) as above, wherein $R_1$ to $R_3$ are as described above (embodiment a), and wherein $R_4$ and $R_5$=

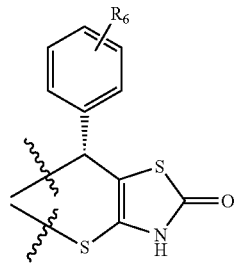

wherein $R_6$=H, OH, alkyl, alkoxy, carbonyl, alkoxycarbonyl, $NO_2$, amine, aminocarbonyl, halogen, $CX_3$, wherein X is a halogen.

This embodiment is directed to compounds of general formula I (embodiment a) corresponding to the preferred enantiomer S37a, as described in more detail below. The compounds of any given formula described herein are—in some embodiments—defined by the enantiomeric conformation corresponding to S37a.

It was entirely surprising that the enantiomers corresponding to S37a would show enhanced antagonism of an activated TSHR compared to the enantiomer corresponding to S37b. The embodiments directed to enantiomers corresponding to S37a are therefore preferred embodiments of the invention.

In a preferred embodiment the invention relates to a compound according to Formula I (embodiment b) for use in the treatment of a subject afflicted by a hyperthyroidism, Formula I

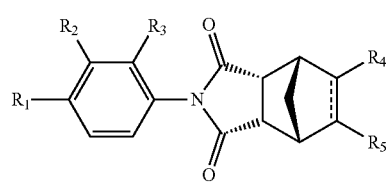

wherein $R_1$=H, OH, alkyl, O-alkyl, CO-alkyl, C(O)O-alkyl, $NH_2$, halogen, preferably F, an optionally substituted 6-member ring, preferably phenyl, wherein said optional substituent is selected from the group consisting of OH, alkyl, O-alkyl, CO-alkyl, C(O)O-alkyl, $NO_2$, $NH_2$, halogen, $CX_3$, wherein X is halogen, or wherein

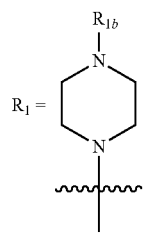

wherein $R_{1b}$=alkyl, an optionally substituted 6-member ring, preferably phenyl, wherein said optional substituent is selected from the group consisting of OH, alkyl, O-alkyl, CO-alkyl, C(O)O-alkyl, $NO_2$, $NH_2$, halogen, $CX_3$, wherein X is a halogen, preferably F;

$R_2$=H, OH, alkyl, O-alkyl, CO-alkyl, C(O)O-alkyl, $NO_2$, $NH_2$, $NHR_{2a}$, $NHR_{2a}R_{2b}$, $NHCOR_{2c}$, wherein $R_{2a}$, $R_{2b}$, $R_{2c}$ is alkyl;

$R_3$=H, OH, alkyl, O-alkyl, C(O)O-alkyl, halogen;

$R_4$, $R_5$=H, alkyl, wherein $R_4$ and $R_5$ can be the same or different, or wherein $R_4$ and $R_5$=

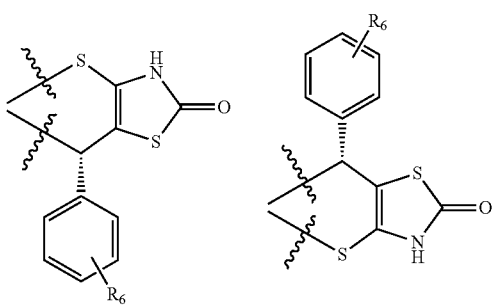

wherein $R_6$=H, OH, alkyl, O-alkyl, CO-alkyl, C(O)O-alkyl, $NO_2$, $NH_2$, $NHR_{2a}$, $NHR_{2a}R_{2b}$, $NHCOR_{2c}$, wherein $R_{2a}$, $R_{2b}$, $R_{2c}$ is alkyl, X, $CX_3$, wherein X is a halogen, preferably F;

and wherein any one or more of said alkyl groups is straight-chained or branched, preferably C1-C6, more preferably Me or Et.

In a preferred embodiment the invention relates to a compound for use in the treatment of a subject afflicted by hyperthyroidism, according to Formula I (embodiment b), wherein $R_1$ to $R_3$ are as in embodiment b,
and wherein $R_4$ and $R_5$=

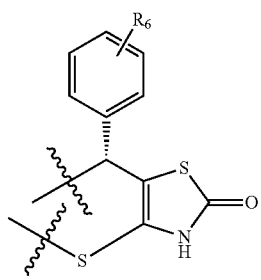

wherein $R_6$=H, OH, alkyl, O-alkyl, CO-alkyl, C(O)O-alkyl, $NO_2$, $NH_2$, $NHR_{2a}$, $NHR_{2a}R_{2b}$, $NHCOR_{2c}$, wherein $R_{2a}$, $R_{2b}$, $R_{2c}$ is alkyl, X, $CX_3$, wherein X is a halogen, preferably F; and wherein any one or more of said alkyl groups is straight-chained or branched, preferably C1-C6, more preferably Me or Et.

This embodiment is directed to compounds of general formula I (embodiment b) corresponding to the preferred enantiomer S37a, as described in more detail below.

In a preferred embodiment of the invention the compound for use as a medicament in the treatment of a subject afflicted by a hyperthyroidism is according to Formula II (embodiment a)

Formula II

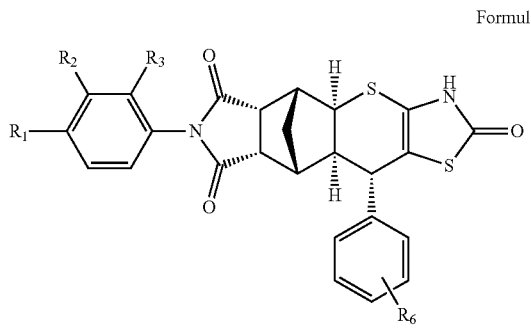

wherein $R_1$=H, OH, alkyl, alkoxy, carbonyl, alkoxycarbonyl, $NH_2$, halogen, an optionally substituted 6-member ring, preferably an aryl group, such as phenyl, wherein said optional substituent is selected from the group consisting of OH, alkyl, alkoxy, carbonyl, alkoxycarbonyl, $NO_2$, amine, halogen, $CX_3$, wherein X is a halogen, or wherein

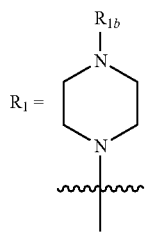

wherein $R_{1b}$=alkyl, an optionally substituted 6-member ring, preferably an aryl group, such as phenyl, wherein said optional substituent is selected from the group consisting of OH, alkyl, alkoxy, carbonyl, alkoxycarbonyl, $NO_2$, amine, halogen, $CX_3$, wherein X is a halogen;

$R_2$=H, OH, alkyl, alkoxy, carbonyl, alkoxycarbonyl, $NO_2$, amine, aminocarbonyl;

$R_3$=H, OH, alkyl, alkoxy, carbonyl, alkoxycarbonyl, halogen;

$R_6$=H, OH, alkyl, alkoxy, carbonyl, alkoxycarbonyl, $NO_2$, amine, aminocarbonyl, halogen, $CX_3$, wherein X is a halogen;

wherein this embodiment described for Formula II encompasses enantiomers of the structure disclosed.

In a preferred embodiment the invention relates to a compound for use as a medicament according to Formula III (embodiment a)

Formula III

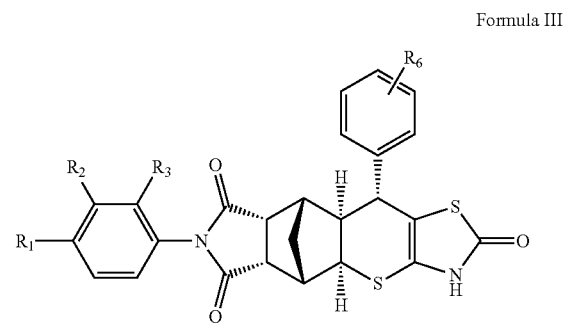

wherein $R_1$=H, OH, alkyl, alkoxy, carbonyl, alkoxycarbonyl, $NH_2$, halogen, an optionally substituted 6-member ring, preferably an aryl group, such as phenyl, wherein said optional substituent is selected from the group consisting of OH, alkyl, alkoxy, carbonyl, alkoxycarbonyl, $NO_2$, amine, halogen, $CX_3$, wherein X is a halogen, or wherein

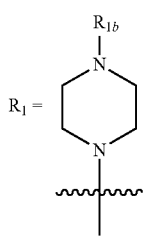

wherein R$_{1b}$=alkyl, an optionally substituted 6-member ring, preferably an aryl group, such as phenyl, wherein said optional substituent is selected from the group consisting of OH, alkyl, alkoxy, carbonyl, alkoxycarbonyl, NO$_2$, amine, halogen, CX$_3$, wherein X is a halogen;

R$_2$=H, OH, alkyl, alkoxy, carbonyl, alkoxycarbonyl, NO$_2$, amine, aminocarbonyl;

R$_3$=H, OH, alkyl, alkoxy, carbonyl, alkoxycarbonyl, halogen;

R$_6$=H, OH, alkyl, alkoxy, carbonyl, alkoxycarbonyl, NO$_2$, amine, aminocarbonyl, halogen, CX$_3$, wherein X is a halogen.

This embodiment is directed to compounds of general formula III (embodiment a) corresponding to the preferred enantiomer S37a, as described in more detail below.

In a preferred embodiment of the invention the compound for use as a medicament in the treatment of a subject afflicted by a hyperthyroidism is according to Formula II (embodiment b)

Formula II

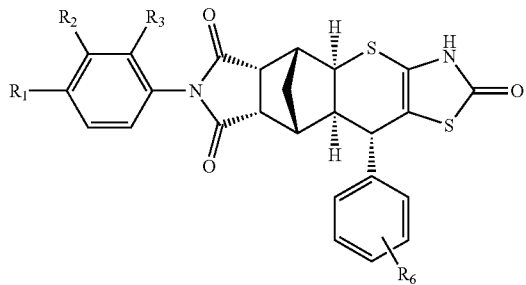

wherein
R$_1$=H, OH, alkyl, O-alkyl, CO-alkyl, C(O)O-alkyl, NH$_2$, halogen, preferably F, an optionally substituted 6-member ring, preferably phenyl, wherein said optional substituent is selected from the group consisting of OH, alkyl, O-alkyl, CO-alkyl, C(O)O-alkyl, NO$_2$, NH$_2$, halogen, CX$_3$, wherein X is halogen, or wherein

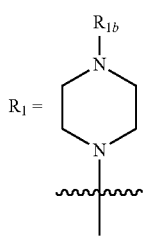

wherein R$_{1b}$=alkyl, an optionally substituted 6-member ring, preferably phenyl, wherein said optional substituent is selected from the group consisting of OH, alkyl, O-alkyl, CO-alkyl, C(O)O-alkyl, NO$_2$, NH$_2$, halogen, CX$_3$, wherein X is a halogen, preferably F;

R$_2$=H, OH, alkyl, O-alkyl, CO-alkyl, C(O)O-alkyl, NO$_2$, NH$_2$, NHR$_{2a}$, NHR$_{2a}$R$_{2b}$, NHCOR$_{2c}$, wherein R$_{2a}$, R$_{2b}$, R$_{2c}$ is alkyl;

R$_3$=H, OH, alkyl, O-alkyl, C(O)O-alkyl, halogen;

R$_6$=H, OH, alkyl, O-alkyl, CO-alkyl, C(O)O-alkyl, NO$_2$, NH$_2$, NHR$_{2a}$, NHR$_{2a}$R$_{2b}$, NHCOR$_{2c}$, wherein R$_{2a}$, R$_{2b}$, R$_{2c}$ is alkyl, halogen, CX$_3$, wherein X is a halogen, preferably F;

and wherein any one or more of said alkyl groups is straight-chained or branched, preferably C1-C6, more preferably Me or Et, wherein this embodiment described for Formula II encompasses enantiomers of the structure disclosed.

In a preferred embodiment the invention relates to a compound for use as a medicament according to any one of the preceding claims, according to Formula III (embodiment b)

Formula III

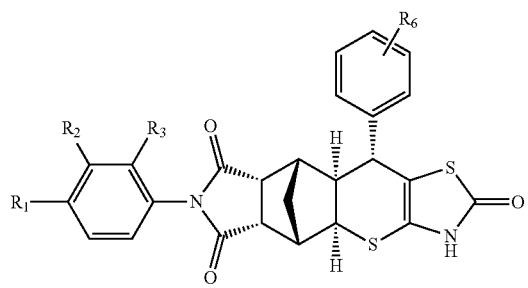

R$_1$=H, OH, alkyl, O-alkyl, CO-alkyl, C(O)O-alkyl, NH$_2$, halogen, preferably F, an optionally substituted 6-member ring, preferably phenyl, wherein said optional substituent is selected from the group consisting of OH, alkyl, O-alkyl, CO-alkyl, C(O)O-alkyl, NO$_2$, NH$_2$, halogen, CX$_3$, wherein X is halogen, or wherein

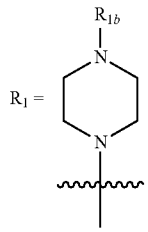

wherein R$_{1b}$=alkyl, an optionally substituted 6-member ring, preferably phenyl, wherein said optional substituent is selected from the group consisting of OH, alkyl, O-alkyl, CO-alkyl, C(O)O-alkyl, NO$_2$, NH$_2$, halogen, CX$_3$, wherein X is a halogen, preferably F;

R$_2$=H, OH, alkyl, O-alkyl, CO-alkyl, C(O)O-alkyl, NO$_2$, NH$_2$, NHR$_{2a}$, NHR$_{2a}$R$_{2b}$, NHCOR$_{2c}$, wherein R$_{2a}$, R$_{2b}$, R$_{2c}$ is alkyl;

R$_3$=H, OH, alkyl, O-alkyl, C(O)O-alkyl, halogen;

R$_6$=H, OH, alkyl, O-alkyl, CO-alkyl, C(O)O-alkyl, NO$_2$, NH$_2$, NHR$_{2a}$, NHR$_{2a}$R$_{2b}$, NHCOR$_{2c}$, wherein R$_{2a}$, R$_{2b}$, R$_{2c}$ is alkyl, halogen, CX$_3$, wherein X is a halogen, preferably F;

and wherein any one or more of said alkyl groups is straight-chained or branched, preferably C1-C6, more preferably Me or Et.

This embodiment is directed to compounds of general formula III (embodiment b) corresponding to the preferred enantiomer S37a, as described in more detail below.

In a further preferred embodiment of the invention the compound for use as a medicament in the treatment of a subject afflicted by a hyperthyroidism is according to Formula I (embodiment c)

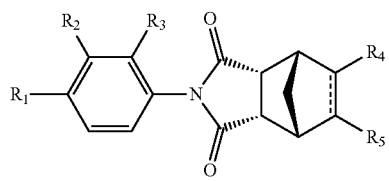

Formula I wherein

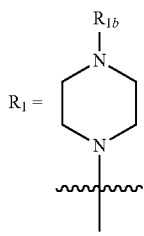

wherein $R_{1b}$=alkyl, an optionally substituted 6-member ring, preferably an aryl group, such as phenyl, wherein said optional substituent is selected from the group consisting of OH, alkyl, alkoxy, carbonyl, alkoxycarbonyl, $NO_2$, amine, halogen, $CX_3$, wherein X is a halogen;

$R_2$=H, OH, alkyl, alkoxy, carbonyl, alkoxycarbonyl, $NO_2$, amine, aminocarbonyl;

$R_3$=H, OH, alkyl, alkoxy, carbonyl, alkoxycarbonyl, halogen;

$R_4$, $R_5$=H, alkyl, alkoxy, carbonyl, alkoxycarbonyl.

In a preferred embodiment of the invention the compound for use as a medicament in the treatment of a subject afflicted by a hyperthyroidism is according to Formula I (embodiment d)

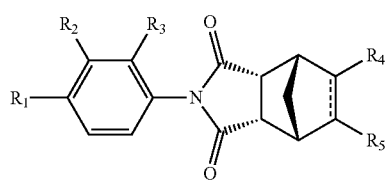

Formula I wherein

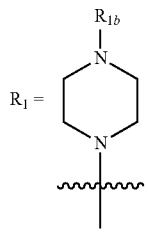

wherein $R_{1b}$=alkyl, an optionally substituted 6-member ring, preferably phenyl, wherein said optional substituent is selected from the group consisting of OH, alkyl, O-alkyl, CO-alkyl, C(O)O-alkyl, $NO_2$, $NH_2$, halogen, $CX_3$, wherein X is a halogen, preferably F;

$R_2$=H, OH, alkyl, O-alkyl, CO-alkyl, C(O)O-alkyl, $NO_2$, $NH_2$, $NHR_{2a}$, $NHR_{2a}R_{2b}$, $NHCOR_{2c}$, wherein $R_{2a}$, $R_{2b}$, $R_{2c}$ is alkyl;

$R_3$=H, OH, alkyl, O-alkyl, C(O)O-alkyl, halogen;

$R_4$, $R_5$=H, alkyl, preferably H;

and wherein any one or more of said alkyl groups is straight-chained or branched, preferably C1-C6, more preferably Me or Et.

In a preferred embodiment of the invention the compound for use as a medicament in the treatment of a subject afflicted by a hyperthyroidism according to Formula II or III (with reference to all previously mentioned embodiments and/or enantiomers) is characterized in that $R_1$=H, OH, Me, O-Me, CO-Me, C(O)O-Me, $NH_2$, halogen, phenyl, or substituted phenyl comprising a C(O)O-Me group, or wherein

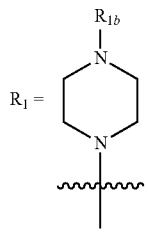

wherein $R_{1b}$=Me, phenyl;
$R_2$=H, Me, $NO_2$, $NH_2$;
$R_3$=H, OH, Me, O-Me, C(O)O-Me;
$R_6$=H, OH, Me, O-Me, CO-Me, C(O)O-Me, $N(CH_3)_2$, F, $CF_3$.

In a preferred embodiment of the invention the compound for use as a medicament in the treatment of a subject afflicted by a hyperthyroidism according to Formula I (embodiment e) is characterized in that

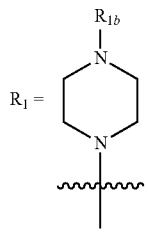

wherein $R_{1b}$=Me, $C(O)O(CH_2)_2CH_3$, phenyl, or substituted phenyl comprising a $CF_3$ group;

$R_2$=H, Me, $NO_2$, $NH_2$;
$R_3$=H, OH, Me, O-Me, C(O)O-Me;
$R_4$, $R_5$=H.

In further preferred embodiments of the invention the compound for use as a medicament according to Formula I or II is selected from the group consisting of

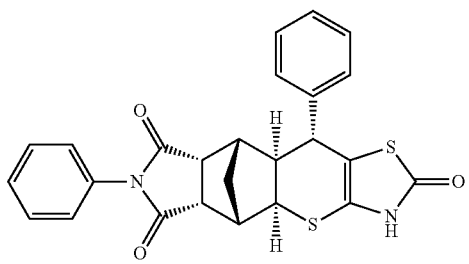

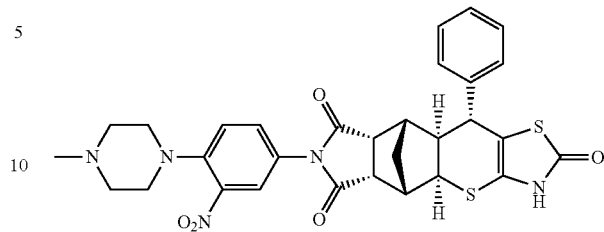

In further embodiments of the invention the compound for use as a medicament as described herein according to Formulae I, II or III is selected from the group provided in Table 1.

TABLE 1

Preferred compounds of Formula I or II of the present invention, represented as enantiomers.

| Structure | ID | Empirical Formula | Molar Mass |
|---|---|---|---|
| 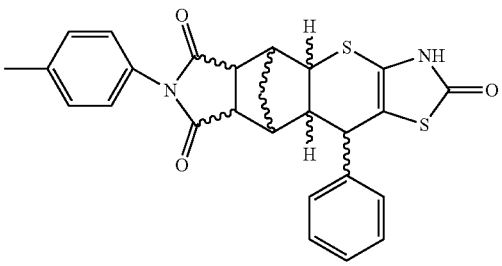 | S4 | $C_{26}H_{22}N_2O_3S_2$ | 474.11 |
| 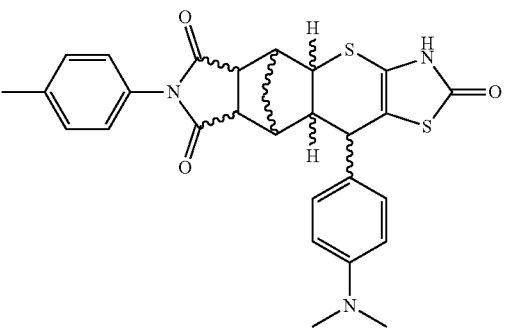 | S18 | $C_{28}H_{27}N_3O_3S_2$ | 517.15 |
| 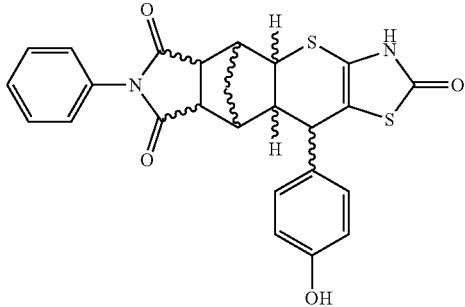 | S19 | $C_{25}H_{20}N_2O_4S_2$ | 476.09 |

TABLE 1-continued

Preferred compounds of Formula I or II of the present invention, represented as enantiomers.

| Structure | ID | Empirical Formula | Molar Mass |
|---|---|---|---|
| 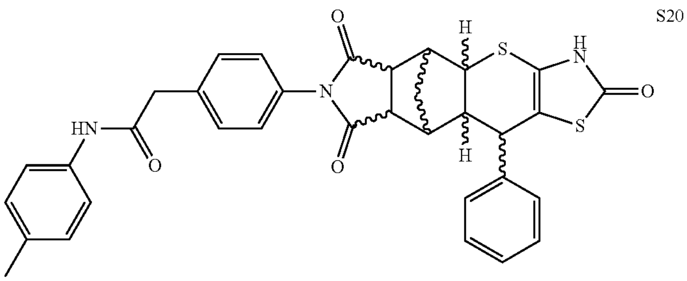 | S20 | $C_{28}H_{25}N_3O_4S_2$ | 531.13 |
| 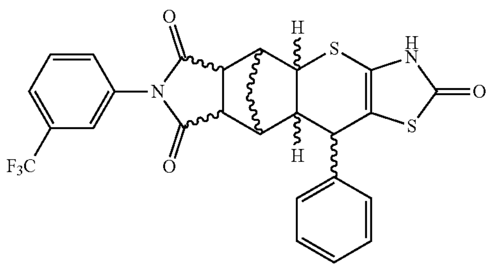 | S21 | $C_{26}H_{19}F_3N_2O_3S_2$ | 528.08 |
| 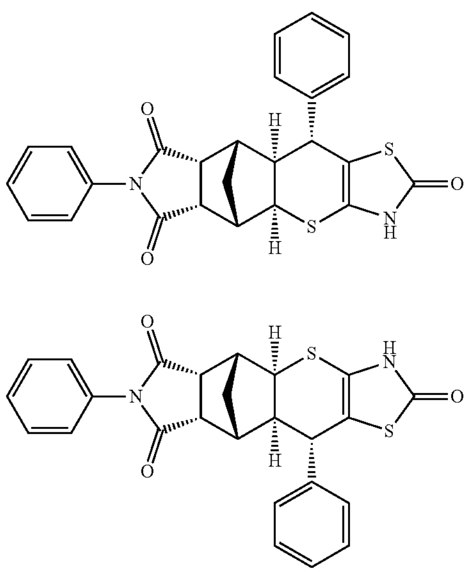 | S37 | $C_{25}H_{20}N_2O_3S_2$ | 460.09 |
| 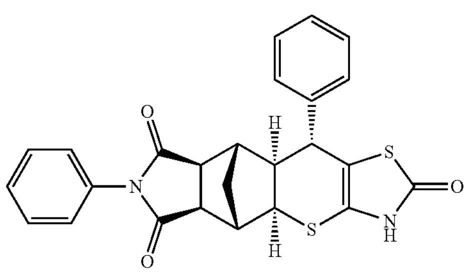 [SMILES: O=C1[C@@H]2[C@@H]3C[C@H]([C@@H]2C(=O)N1c1ccccc1)[C@H]1[C@H](c2ccccc2)c2sc(=O)[nH]c2S[C@@H]31] | S36 | $C_{25}H_{20}N_2O_3S_2$ | 460.09 |

TABLE 1-continued

Preferred compounds of Formula I or II of the present invention, represented as enantiomers.

| Structure | ID | Empirical Formula | Molar Mass |
|---|---|---|---|
| 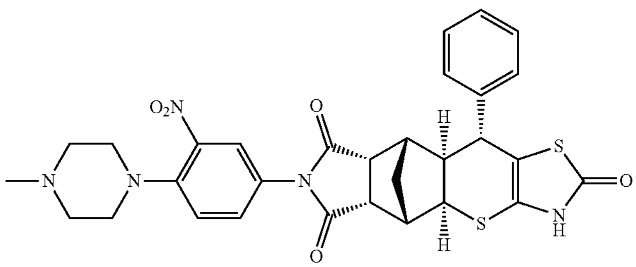 [SMILES: CN1CCN(c2ccc(N3C(=O)[C@@H]4[C@H]5C[C@H]([C@@H]6Sc7[nH]c(=O)sc7[C@@H](c7ccccc7)[C@H]56)[C@@H]4C3=O)cc2[N+](=O)[O-])CC1] | S38 | C$_{30}$H$_{29}$N$_5$O$_5$S$_2$ | 603.71 |
| 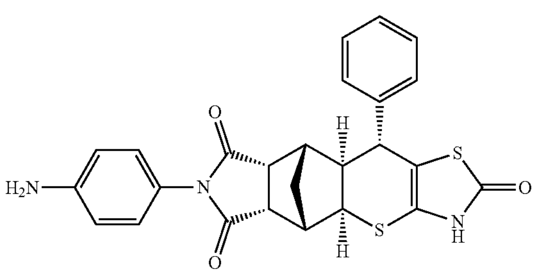 [SMILES: Nc1ccc(N2C(=O)[C@@H]3[C@H]4C[C@H]([C@@H]5Sc6[nH]c(=O)sc6[C@@H](c6ccccc6)[C@H]45)[C@@H]3C2=O)cc1] | S79 | C$_{25}$H$_{21}$N$_3$O$_3$S$_2$ | 475.10 |

TABLE 1-continued

Preferred compounds of Formula I or II of the present invention, represented as enantiomers.

| Structure | ID | Empirical Formula | Molar Mass |
|---|---|---|---|
| 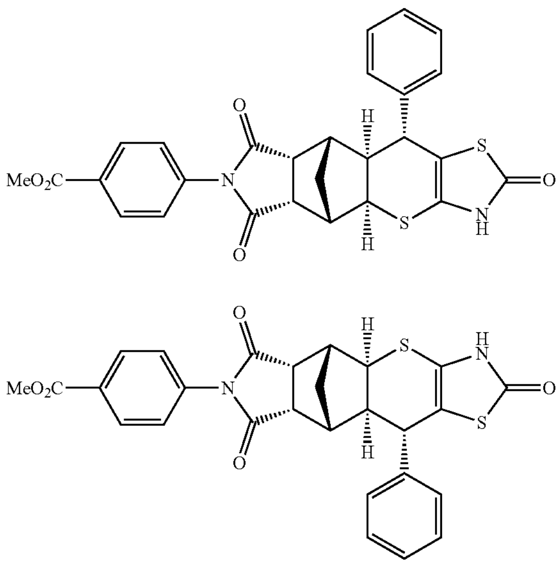 | S87 | $C_{27}H_{22}N_2O_5S_2$ | 518.10 |
| 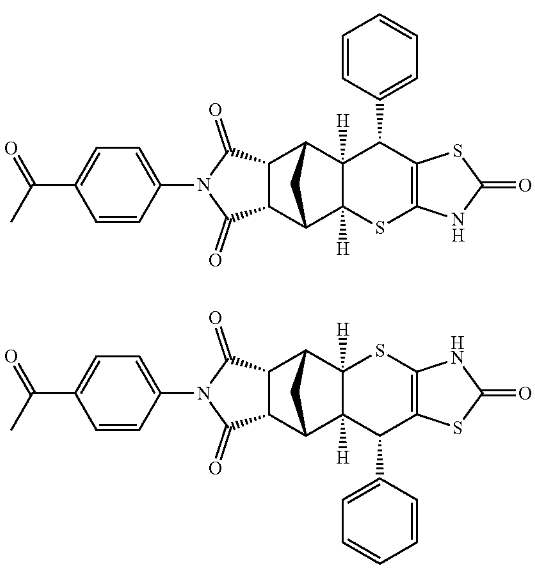 | S80 | $C_{27}H_{22}N_2O_4S_2$ | 502.10 |
| 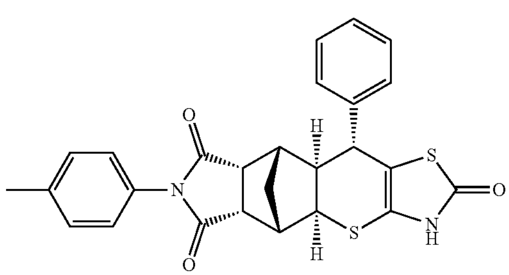 [SMILES: Cc1ccc(N2C(=O)[C@@H]3[C@H]4C[C@H]([C@@H]5Sc6[nH]c(=O)sc6[C@@H](c6ccccc6)[C@H]45)[C@@H]3C2=O)cc1] | S90 | $C_{26}H_{22}N_2O_3S_2$ | 474.11 |

TABLE 1-continued

Preferred compounds of Formula I or II of the present invention, represented as enantiomers.

| Structure | ID | Empirical Formula | Molar Mass |
|---|---|---|---|
| 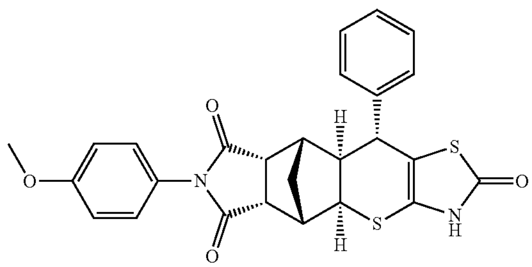 [SMILES: COc1ccc(N2C(=O)[C@@H]3[C@H]4C[C@H]([C@@H]5Sc6[nH]c(=O)sc6[C@@H](c6ccccc6)[C@H]45)[C@@H]3C2=O)cc1] | S89 | C₂₆H₂₂N₂O₄S₂ | 490.10 |
| | | | |
| 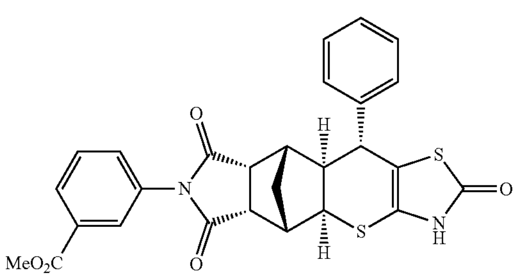 [SMILES: COC(=O)c1cccc(N2C(=O)[C@@H]3[C@H]4C[C@H]([C@@H]5Sc6[nH]c(=O)sc6[C@@H](c6ccccc6)[C@H]45)[C@@H]3C2=O)c1] | S96 | C₂₇H₂₂N₂O₅S₂ | 518.10 |
| | | | |

TABLE 1-continued

Preferred compounds of Formula I or II of the present invention, represented as enantiomers.

| Structure | ID | Empirical Formula | Molar Mass |
|---|---|---|---|
| 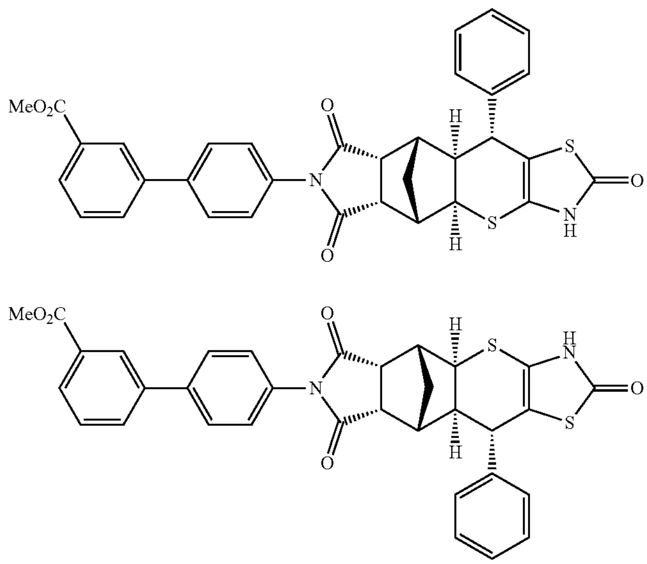 | S98 | $C_{33}H_{26}N_2O_5S_2$ | 594.13 |
| 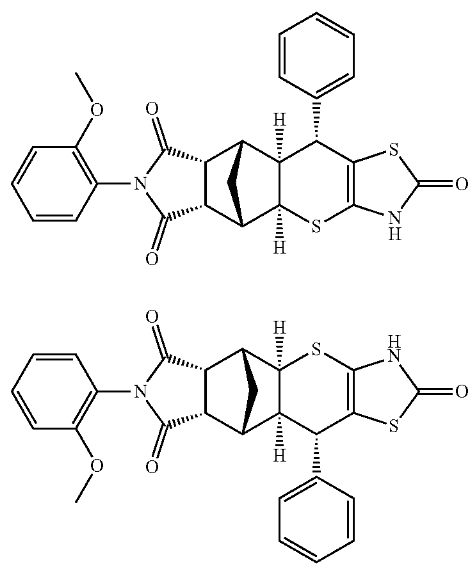 | S99 | $C_{26}H_{22}N_2O_4S_2$ | 490.10 |
| 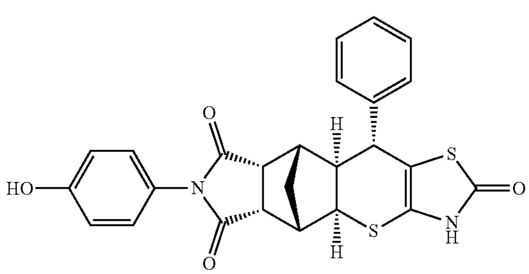 [SMILES: O=C1[C@@H]2[C@H]3C[C@H]([C@@H]4Sc5[nH]c(=O)sc5[C@@H](c5ccccc5)[C@H]34)[C@@H]2C(=O)N1c1ccc(O)cc1] | S100 | $C_{25}H_{20}N_2O_4S_2$ | 476.09 |

TABLE 1-continued

Preferred compounds of Formula I or II of the present invention, represented as enantiomers.

| Structure | ID | Empirical Formula | Molar Mass |
|---|---|---|---|
| 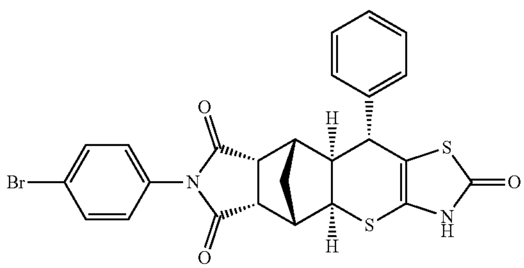 [SMILES: O=C1[C@@H]2[C@H]3C[C@H]([C@@H]4Sc5[nH]c(=O)sc5[C@@H](c5ccccc5)[C@H]34)[C@@H]2C(=O)N1c1ccc(Br)cc1] | S101 | $C_{25}H_{19}BrN_2O_3S_2$ | 538.00 |
| 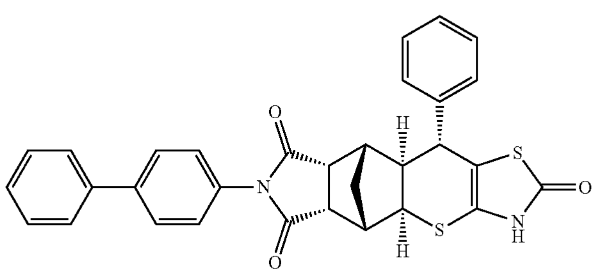 [SMILES: O=C1[C@@H]2[C@H]3C[C@H]([C@@H]4Sc5[nH]c(=O)sc5[C@@H](c5ccccc5)[C@H]34)[C@@H]2C(=O)N1c1ccc(-c2ccccc2)cc1] | S102 | $C_{31}H_{24}N_2O_3S_2$ | 536.12 |

TABLE 1-continued

Preferred compounds of Formula I or II of the present invention, represented as enantiomers.

| Structure | ID | Empirical Formula | Molar Mass |
|---|---|---|---|
| 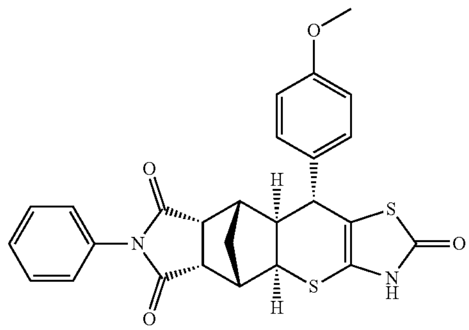 [SMILES: COc1ccc([C@@H]2c3sc(=O)[nH]c3S[C@H]3[C@H]4C[C@H]([C@H]5C(=O)N(c6ccccc6)C(=O)[C@@H]45)[C@@H]23)cc1] | S123 | $C_{26}H_{22}N_2O_4S_2$ | 490.10 |
| 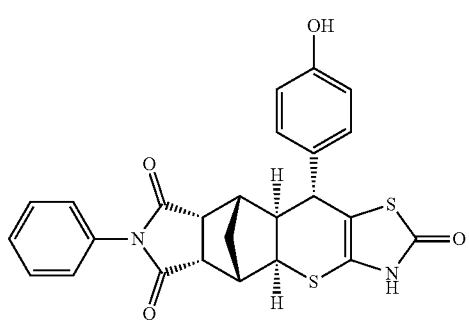 [SMILES: O=C1[C@@H]2[C@H]3C[C@H]([C@@H]4Sc5[nH]c(=O)sc5[C@@H](c5ccc(O)cc5)[C@H]34)[C@@H]2C(=O)N1c1ccccc1] | S122 | $C_{25}H_{20}N_2O_4S_2$ | 476.09 |

TABLE 1-continued

Preferred compounds of Formula I or II of the present invention, represented as enantiomers.

| Structure | ID | Empirical Formula | Molar Mass |
|---|---|---|---|
|  | S121 | $C_{27}H_{25}N_3O_3S_2$ | 503.13 |
|  | S124 | $C_{25}H_{19}FN_2O_3S_2$ | 478.08 |

TABLE 1-continued

Preferred compounds of Formula I or II of the present invention, represented as enantiomers.

| Structure | ID | Empirical Formula | Molar Mass |
|---|---|---|---|
| 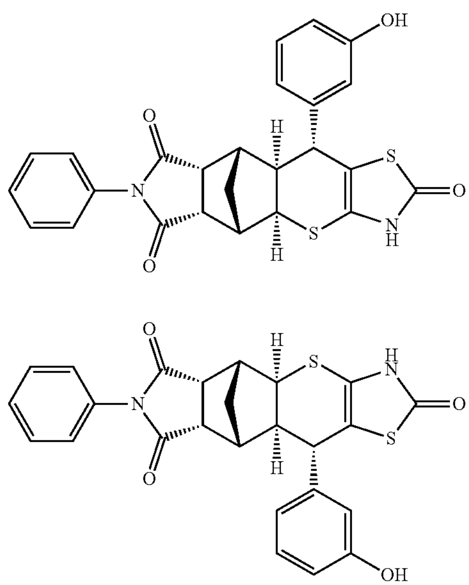 | S125 | $C_{25}H_{20}N_2O_4S_2$ | 476.09 |
| 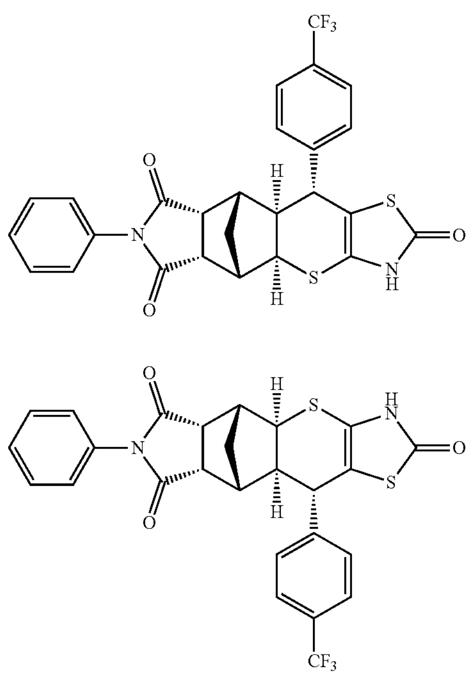 | S128 | $C_{26}H_{19}F_3N_2O_3S_2$ | 528.08 |
| 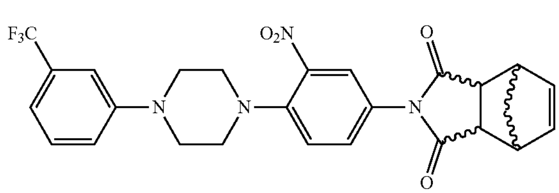 | S9 | $C_{26}H_{23}F_3N_4O_4$ | 512.48 |

TABLE 1-continued

Preferred compounds of Formula I or II of the present invention, represented as enantiomers.

| Structure | ID | Empirical Formula | Molar Mass |
|---|---|---|---|
| 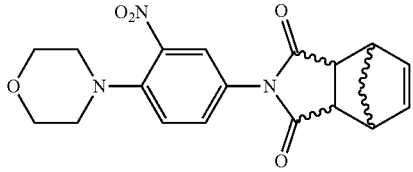 | S26 | $C_{19}H_{19}N_3O_5$ | 369.13 |
| 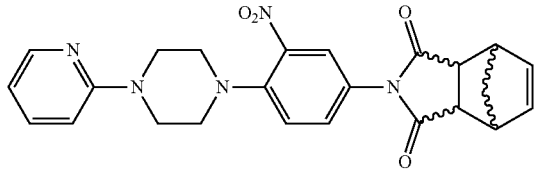 | S30 | $C_{25}H_{24}N_4O_4$ | 444.18 |
| 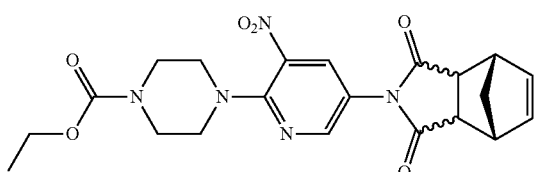 | S34 | $C_{21}H_{23}N_5O_6$ | 440.17 |
| 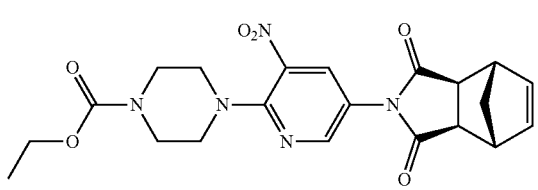 [SMILES: CCOC(=O)N1CCN(c2ncc(N3C(=O)[C@@H]4[C@H](C3=O)[C@H]3C=C[C@@H]4C3)cc2[N+](=O)[O-])CC1] | S35 | $C_{21}H_{23}N_5O_6$ | 440.17 |

In further embodiments of the invention the compound for use as a medicament as described herein according to Formula I or III is selected from the group consisting of:

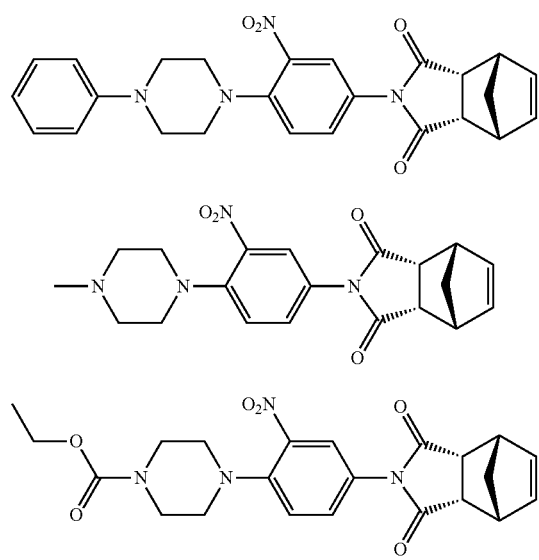

In a preferred embodiment the compound for use as a medicament according to any one of the formulae described herein is characterized in that the thyroid disease to be treated is associated with defective thyroid-stimulating hormone receptor (TSHR) signaling.

In a preferred embodiment the compound for use as a medicament according to any one of the formulae described herein is characterized in that the thyroid disease to be treated is hyperthyroidism.

In a preferred embodiment the compound for use as a medicament according to any one of the formulae described herein is characterized in that the thyroid disease to be treated is an autoimmune disorder.

In a preferred embodiment the compound for use as a medicament according to any one of the formulae described herein is characterized in that the thyroid disease to be treated is Graves' disease.

In a preferred embodiment the compound for use as a medicament according to any one of the formulae described herein is characterized in that the thyroid disease to be treated is Graves' ophthalmopathy and/or Graves' dermopathy.

In a preferred embodiment the compound for use as a medicament according to any one of the formulae described herein is characterized in that the thyroid disease to be treated is thyroid cancer, preferably a thyroid cancer associated with hyperthyroidism.

In a further aspect of the invention the compound for use as a medicament according to any one of the formulae described herein is provided in the form of a pharmaceutical composition for the treatment of a subject afflicted by a thyroid disease, wherein the composition comprises a pharmaceutically acceptable carrier substance.

The present invention also relates to a method of treating hyperthyroidism, such as those particular embodiments of hyperthyroidism described herein, comprising the administration of a compound as described herein to a subject suffering from or at elevated risk of suffering from hyperthyroidism.

DETAILED DESCRIPTION OF THE INVENTION

All cited documents of the patent and non-patent literature are hereby incorporated by reference in their entirety.

The present invention is directed to the treatment of a subject afflicted by a thyroid disease via administration of the compounds disclosed herein. The term "subject" includes both human and veterinary subjects. The term "treatment" refers to a therapeutic intervention that ameliorates a sign or symptom of a disease or pathological condition after it has begun to develop. As used herein, the term "ameliorating", with reference to a disease or pathological condition, refers to any observable beneficial effect of the treatment. The beneficial effect can be evidenced, for example, by a delayed onset of clinical symptoms of the disease in a susceptible subject, a reduction in severity of some or all clinical symptoms of the disease, a slower progression of the disease, an improvement in the overall health or well-being of the subject, or by other parameters well known in the art that are specific to the particular disease.

The present invention encompasses both treatment and prophylactic treatment of a subject. A "prophylactic" treatment is a treatment administered to a subject who does not exhibit signs of a disease or exhibits only early signs for the purpose of decreasing the risk of developing pathology.

The present invention relates further to pharmaceutically acceptable salts of the compounds described herein. The term "pharmaceutically acceptable salt" refers to salts or esters prepared by conventional means that include basic salts of inorganic and organic acids, including but not limited to hydrochloric acid, hydrobromic acid, sulfuric acid, phosphoric acid, methanesulfonic acid, ethanesulfonic acid, malic acid, acetic acid, oxalic acid, tartaric acid, citric acid, lactic acid, fumaric acid, succinic acid, maleic acid, salicylic acid, benzoic acid, phenylacetic acid, mandelic acid and the like. Any chemical compound recited in this specification may alternatively be administered as a pharmaceutically acceptable salt thereof.

"Pharmaceutically acceptable salts" are also inclusive of the free acid, base, and zwitterionic forms. Descriptions of suitable pharmaceutically acceptable salts can be found in Handbook of Pharmaceutical Salts, Properties, Selection and Use, Wiley VCH (2002). For therapeutic use, salts of the compounds are those wherein the counter-ion is pharmaceutically acceptable. However, salts of acids and bases which are non-pharmaceutically acceptable may also find use, for example, in the preparation or purification of a pharmaceutically acceptable compound.

The term "alkyl" refers to a branched or unbranched saturated hydrocarbon group of 1 to 24 carbon atoms, such as methyl, ethyl, n-propyl, isopropyl, w-butyl, isobutyl, f-butyl, pentyl, hexyl, heptyl, octyl, decyl, tetradecyl, hexadecyl, eicosyl, tetracosyl and the like. Preferred alkyl groups have 1 to 6 carbon atoms, more preferably 1 to 4 carbon atoms. Any one or more of the alkyl groups described herein may be "substituted alkyls", wherein one or more hydrogen atoms are substituted with a substituent such as halogen, cycloalkyl, alkoxy, amino, hydroxyl, aryl, or carboxyl.

The term "alkoxy" refers to a straight, branched or cyclic hydrocarbon configuration and combinations thereof, including from 1 to 20 carbon atoms, preferably from 1 to 8 carbon atoms, more preferably from 1 to 4 carbon atoms, that include an oxygen atom at the point of attachment (such as O-alkyl). An example of an "alkoxy group" is represented by the formula —OR, where R can be an alkyl group, optionally substituted with an alkenyl, alkynyl, aryl, aralkyl, cycloalkyl, halogenated alkyl, or heterocycloalkyl group. Suitable alkoxy groups include methoxy, ethoxy, n-propoxy, i-propoxy, n-butoxy, i-butoxy, sec-butoxy, tert-butoxy cclopropoxy, cyclohexyloxy, and the like.

"Carbonyl" refers to a radical of the formula —C(O)—. Carbonyl-containing groups include any substituent containing a carbon-oxygen double bond (C=O), including acyl groups, amides, carboxy groups, esters, ureas, carbamates, carbonates and ketones and aldehydes, such as substituents based on —COR or —RCHO where R is an aliphatic, heteroaliphatic, alkyl, heteroalkyl, hydroxyl, or a secondary, tertiary, or quaternary amine.

"Alkoxycarbonyl" refers to an alkoxy substituted carbonyl radical (such as —C(O)OR), wherein R represents an optionally substituted alkyl, aryl, aralkyl, cycloalkyl, cycloalkylalkyl or similar moiety.

The term "alkyl amino" refers to alkyl groups as defined above where at least one hydrogen atom is replaced with an amino group.

"Aminocarbonyl" alone or in combination, means an amino substituted carbonyl (carbamoyl) radical, wherein the amino radical may optionally be mono- or di-substituted, such as with alkyl, aryl, aralkyl, cycloalkyl, cycloalkylalkyl, alkanoyl, alkoxycarbonyl, aralkoxycarbonyl and the like. An aminocarbonyl group may be —N(R)—C(O)—R (wherein R is a substituted group or H) or —C(O)—N(R).

The term "aryl" refers to any carbon-based aromatic group including, but not limited to, benzene, naphthalene, etc. The term "aromatic" also includes "heteroaryl group," which is defined as an aromatic group that has at least one heteroatom incorporated within the ring of the aromatic group. Examples of heteroatoms include, but are not limited to, nitrogen, oxygen, sulfur, and phosphorous. The aryl group can be substituted with one or more groups including, but not limited to, alkyl, alkynyl, alkenyl, aryl, halide, nitro, amino, ester, ketone, aldehyde, hydroxy, carboxylic acid, or alkoxy, or the aryl group can be unsubstituted.

"Carboxyl" refers to a —COOH radical. Substituted carboxyl refers to —COOR where R is aliphatic, heteroaliphatic, alkyl, heteroalkyl, or a carboxylic acid or ester.

The term "hydroxyl" is represented by the formula —OH.

The term "hydroxyalkyl" refers to an alkyl group that has at least one hydrogen atom substituted with a hydroxyl group. The term "alkoxyalkyl group" is defined as an alkyl group that has at least one hydrogen atom substituted with an alkoxy group described above.

The term "amine" refers to a group of the formula —NRR', where R and R' can be, independently, hydrogen or an alkyl, alkenyl, alkynyl, aryl, aralkyl, cycloalkyl, halogenated alkyl, or heterocycloalkyl group described above.

The term "amide" or "amido" is represented by the formula —C(O)NRR', where R and R' independently can be a hydrogen, alkyl, alkenyl, alkynyl, aryl, aralkyl, cycloalkyl, halogenated alkyl, or heterocycloalkyl group described above. A suitable amido group is acetamido.

The term "aralkyl" refers to an aryl group having an alkyl group, as defined above, attached to the aryl group, as defined above. An example of an aralkyl group is a benzyl group.

Optionally substituted groups, such as "optionally substituted alkyl," refers to groups, such as an alkyl group, that when substituted, have from 1-5 substituents, typically 1, 2 or 3 substituents, selected from alkoxy, optionally substituted alkoxy, acyl, acylamino, acyloxy, amino, aminoacyl, aminoacyloxy, aryl, carboxyalkyl, optionally substituted cycloalkyl, optionally substituted cycloalkenyl, halogen, optionally substituted heteroaryl, optionally substituted heterocyclyl, hydroxy, sulfonyl, thiol and thioalkoxy. In particular, optionally substituted alkyl groups include, by way of example, haloalkyl groups, such as fluoroalkyl groups, including, without limitation, trifluoromethyl groups. These potential optional substituents apply to any group of the formula disclosed herein where an optional substituent is recited. Preferable optional substituents are hydroxyl, alkyl, alkoxy, carbonyl, alkoxycarbonyl, $NO_2$, amine.

A dotted line in the position of a double bond represents an optional double bond, which may be present or absent.

Protected derivatives of the disclosed compound also are contemplated. A variety of suitable protecting groups for use with the disclosed compounds are disclosed in Greene and Wuts Protective Groups in Organic Synthesis; 3rd Ed.; John Wiley & Sons, New York, 1999. In general, protecting groups are removed under conditions which will not affect the remaining portion of the molecule. These methods are well known in the art and include acid hydrolysis, hydrogenolysis and the like.

Particular examples of the presently disclosed compounds include one or more asymmetric centers; thus these compounds can exist in different stereoisomeric forms. Accordingly, compounds and compositions may be provided as individual pure enantiomers or as stereoisomeric mixtures, including racemic mixtures. In certain embodiments the compounds disclosed herein are synthesized in or are purified to be in substantially enantiopure form, such as in a 90% enantiomeric excess, a 95% enantiomeric excess, a 97% enantiomeric excess or even in greater than a 99% enantiomeric excess, such as in enantiopure form.

It is understood that substituents and substitution patterns of the compounds described herein can be selected by one of ordinary skill in the art to provide compounds that are chemically stable and that can be readily synthesized by techniques known in the art and further by the methods set forth in this disclosure.

Disclosed herein are compounds that are antagonists of TSHR, that is, they inhibit signaling stimulated by TSH.

TSHR in thyroid cells, and likely in fibroblasts and adipocytes in the supporting tissue behind the eye (in the retro-orbital space), also are stimulated by TSHR-stimulating antibodies (TSAbs), resulting in Graves' disease. Graves' disease, which is an autoimmune disease that occurs in 1% of the US population, has two important clinical components—1) hyperthyroidism from stimulation of TSHR on thyroid cells and 2) Graves' orbitopathy (or Graves' ophthalmopathy or thyroid eye disease), which appears to result from stimulation of TSHR on retro-orbital fibroblasts and/or adipocytes.

Hyperthyroidism, in particular Graves' hyperthyroidism, is a hypermetabolic state that affects virtually every tissue/cell in the body and can lead to, in particular, cardiovascular dysfunction and death. Graves' hyperthyroidism can be treated by surgical resection, therapeutic doses of radioactive iodine, or pharmacologically (methimazole or propylthiouracil). However, each of these treatment modalities has side effects associated with it (Cooper D S, 2005 N Engl J Med, 352, 905-917).

Graves' ophthalmopathy, also known as Graves' orbitopathy, occurs in 80% of Graves' hyperthyroid patients as diagnosed by computerized tomographic scan. Symptoms range from mild to moderate to severe to sight-threatening. Protrusion of the eyeball (proptosis) and varying degrees of extra-ocular muscle weakness or paralysis leading to double vision (diplopia) can be disfiguring and incapacitating.

Graves Dermopathy, also known as Pretibial myxedema, thyroid dermopathy, Jadassohn-Dössekker disease or *Myxoedema tuberosum*, is an infiltrative dermopathy, resulting as a complication of Graves' disease, with an incidence rate of about 1-5% in patients. The disease usually presents itself as a waxy, discolored induration of the skin on the anterior aspect of the lower legs.

A further disease that can be treated by TSHR antagonists is thyroid cancer. TSHR is expressed in thyroid cancer cells and regulates the growth, proliferation and metastatic potential of thyroid cancer cells.

The thyroid gland is, as is well known, one site of metabolic control within the body. Cancer of the thyroid gland is not particularly common, but the high rate of disease re-occurrence necessitates long term surveillance. Usually, during treatment for cancer of the thyroid, the majority of the thyroid tumor is removed, but a small amount often remains that must be treated by radioactive iodide therapy. Indeed, thyroid cancer is characterized by a high likelihood of relapses in up to 30% of patients, even after successful therapy.

In rare cases, the TSHR contains a hereditary mutation that makes it more active than the normal TSHR, resulting in hereditary non-immune hyperthyroidism. TSHR antagonists could be effective treatment for these patients also.

A "TSHR antagonist" as described herein blocks or inhibits the action of the agonists (TSH or thyroid-stimulating antibodies for TSHR), but does not inhibit basal/constitutive TSHR activity. Small-molecule ligands for the TSHR (antagonists) typically bind to an intra-membrane domain of the receptor, and act by inducing a conformational change rather than simply competing for TSH binding to its extracellular site on the receptor.

Small molecule (for example, less than 1000 daltons) antagonists are attractive agents because they are more easily employed as probes and drugs compared to TSH, its analogs or anti-TSHR antibodies, can be synthesized chemically in large amounts at moderate cost, and can be given orally because they are not degraded within, and can be absorbed from, the gastrointestinal tract.

Disclosed are TSHR antagonists that may be used for probes of TSHR biology or treating subjects with Graves' orbitopathy and/or Graves' hyperthyroidism.

In certain embodiments, the antagonists may be selective antagonists for TSHR (i.e, the compounds do not activate or modulate other hormone receptors, particularly luteinizing hormone/chorionic gonadotropin receptor (LHCGR) and follicle-stimulating hormone receptor (FSHR)).

In certain embodiments, the antagonists disclosed herein may be used for treating hyperthyroidism in a subject. For example, the antagonists may inhibit mutant TSHRs with higher than normal basal signaling activities (CAMs) that cause an unusual form of hyperthyroidism. In another example, the antagonists may inhibit stimulation by antibodies found in Graves' disease, which is the most common form of hyperthyroidism.

In certain embodiments, the TSHR antagonists are useful for treating TSHR-mediated thyroid cancer or hyperthyroidism by blocking TSHR-stimulating antibodies (TSAbs) in Graves' hyperthyroidism.

The invention comprises antibody-drug conjugates (ADCs) that comprise one or more antibodies or fragments thereof linked to a compound of the present invention. By combining the unique targeting capabilities of antibodies, for example monoclonal antibodies targeting the TSHR, with the antagonistic activity of the compounds of the present invention, antibody-drug conjugates may enable additional increases in TSHR-specificity. For example, the compound S9 and derivatives thereof, preferably according to the embodiments described herein relating to formula III, may be conjugated to an anti-TSHR antibody, thereby increasing specificity for the TSHR and reducing the effects at the LHCGR or FSHR. ADCs may also be contemplated for compounds of Formula I, or II, in order to enhance specificity or targeting to relevant tissues. A linker molecule may be employed conjugating the antibody or fragment thereof to the compound of the present invention. A stable link between the antibody and compound is a key aspect of an ADC. Linkers may be based on chemical motifs including disulfides, hydrazones or peptides (potentially cleavable peptides), or thioethers (non-cleavable). Cleavable and non-cleavable types of linkers have been tested and are known to a skilled person.

Another aspect of the disclosure includes pharmaceutical compositions prepared for administration to a subject and which include a therapeutically effective amount of one or more of the compounds disclosed herein. In certain embodiments, the pharmaceutical compositions are useful for treating Graves' disease, thyroid cancer, hyperthyroidism (particularly Graves' hyperthyroidism), or Graves' orbitopathy. The therapeutically effective amount of a disclosed compound will depend on the route of administration, the species of subject and the physical characteristics of the subject being treated. Specific factors that can be taken into account include disease severity and stage, weight, diet and concurrent medications. The relationship of these factors to determining a therapeutically effective amount of the disclosed compounds is understood by those of skill in the art.

Pharmaceutical compositions for administration to a subject can include at least one further pharmaceutically acceptable additive such as carriers, thickeners, diluents, buffers, preservatives, surface active agents and the like in addition to the molecule of choice. Pharmaceutical compositions can also include one or more additional active ingredients such as antimicrobial agents, anti-inflammatory agents, anesthetics, and the like. The pharmaceutically acceptable carriers useful for these formulations are conventional. Remington's Pharmaceutical Sciences, by E. W. Martin, Mack Publishing Co., Easton, Pa., 19th Edition (1995), describes compositions and formulations suitable for pharmaceutical delivery of the compounds herein disclosed.

In general, the nature of the carrier will depend on the particular mode of administration being employed. For instance, parenteral formulations usually contain injectable fluids that include pharmaceutically and physiologically acceptable fluids such as water, physiological saline, balanced salt solutions, aqueous dextrose, glycerol or the like as a vehicle. For solid compositions (for example, powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

The pharmaceutical compositions can be administered to subjects by a variety of mucosal administration modes, including by oral, rectal, intraocular, intranasal, intrapulmonary, or transdermal delivery, or by topical delivery to other surfaces. Optionally, the compositions can be administered by non-mucosal routes, including by intramuscular, intraocular, subcutaneous, intravenous, intra-arterial, intra-articular, intraperitoneal, intrathecal, intracerebroventricular, or parenteral routes.

The compositions of the disclosure can alternatively contain as pharmaceutically acceptable carrier substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, and triethanolamine oleate. For solid compositions, conventional nontoxic pharmaceutically acceptable vehicles can be used which include, for example, pharmaceutical grades of mannitol, lactose, starch, magnesium stearate, sodium saccharin, talcum, cellulose, glucose, sucrose, magnesium carbonate, and the like.

In accordance with the various treatment methods of the disclosure, the compound can be delivered to a subject in a manner consistent with conventional methodologies associated with management of the disorder for which treatment or prevention is sought. In accordance with the disclosure herein, a prophylactically or therapeutically effective amount of the compound and/or other biologically active agent is administered to a subject in need of such treatment for a time and under conditions sufficient to prevent, inhibit, and/or ameliorate a selected disease or condition or one or more symptom(s) thereof.

"Administration of" and "administering a" compound should be understood to mean providing a compound, a prodrug of a compound, or a pharmaceutical composition as described herein. The compound or composition can be administered by another person to the subject (e.g., intravenously) or it can be self-administered by the subject (e.g., tablets).

Dosage can be varied by the attending clinician to maintain a desired concentration at a target site (for example, the lungs or systemic circulation). Higher or lower concentrations can be selected based on the mode of delivery, for example, trans-epidermal, rectal, oral, pulmonary, or intra-nasal delivery versus intravenous or subcutaneous delivery. Dosage can also be adjusted based on the release rate of the administered formulation, for example, of an intrapulmonary spray versus powder, sustained release oral versus injected particulate or transdermal delivery formulations, and so forth.

The present invention also relates to a method of treatment of subjects suffering from the various medical conditions disclosed herein. The method of treatment comprises preferably the administration of a therapeutically effective amount of a compound disclosed herein to a subject in need thereof.

A "therapeutically effective amount" refers to a quantity of a specified agent sufficient to achieve a desired effect in a subject being treated with that agent. For example, this may be the amount of a compound disclosed herein useful in treating a disease of the thyroid in a subject. The therapeutically effective amount or diagnostically effective amount of an agent will be dependent on the subject being treated, the severity of the affliction, and the manner of administration of the therapeutic composition. Dosage regimens can be adjusted to provide an optimum prophylactic or therapeutic response. A therapeutically effective amount is also one in which any toxic or detrimental side effects of the compound and/or other biologically active agent is outweighed in clinical terms by therapeutically beneficial effects. A non-limiting range for a therapeutically effective amount of a compound and/or other biologically active agent within the methods and formulations of the disclosure is about 0.001 mg/kg body weight to 50 mg/kg body weight, 0.01 mg/kg body weight to about 20 mg/kg body weight, such as about 0.05 mg kg to about 5 mg/kg body weight, or about 0.2 mg/kg to about 2 mg/kg body weight.

The instant disclosure also includes kits, packages and multi-container units containing the herein described pharmaceutical compositions, active ingredients, and/or means for administering the same for use in the prevention and treatment of diseases and other conditions in mammalian subjects.

FIGURES

The invention is further described by the following figures. These are not intended to limit the scope of the invention, but represent preferred embodiments of aspects of the invention provided for greater illustration of the invention described herein.

DETAILED DESCRIPTION OF THE FIGURES

Figure 1:
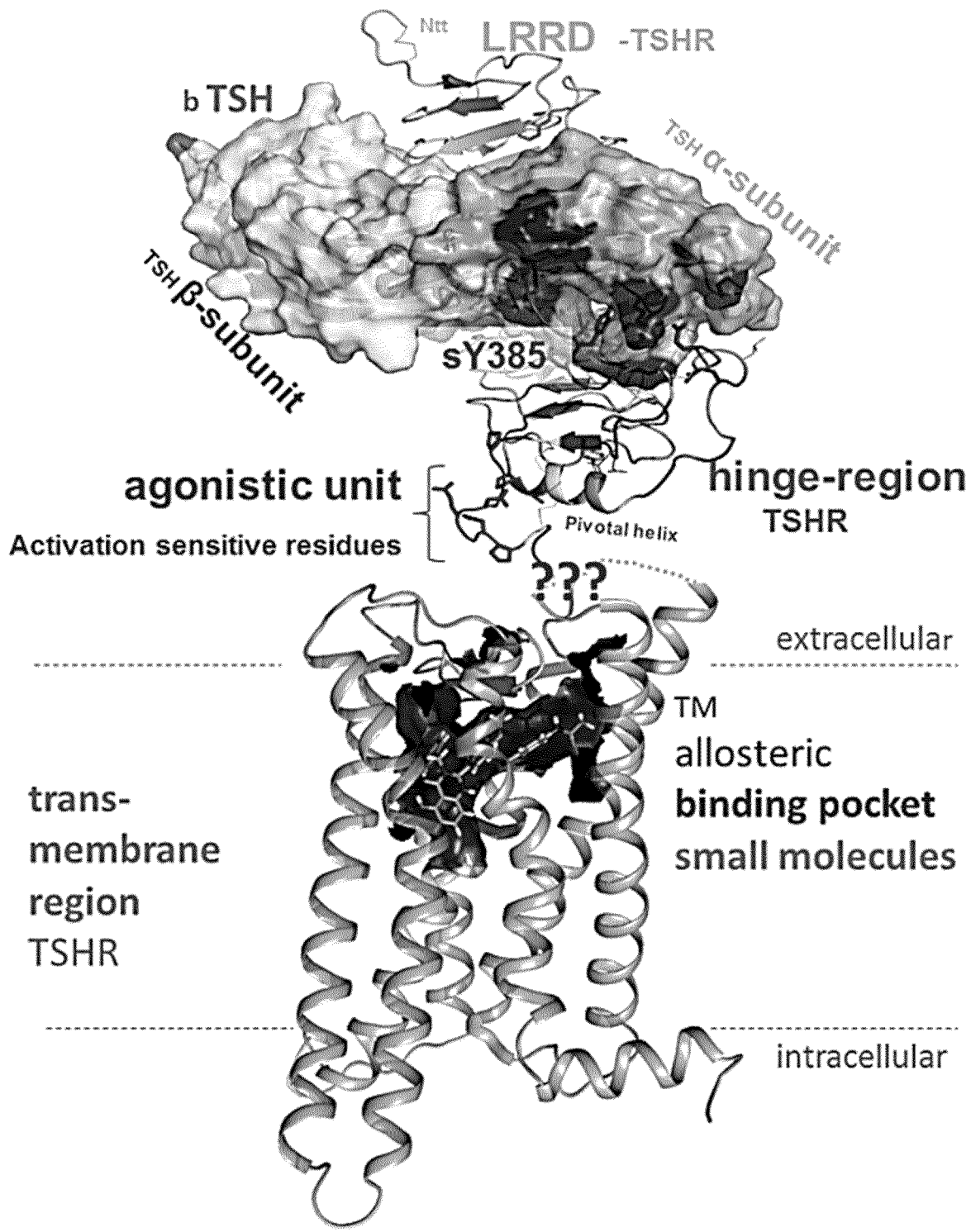
FIG. 1: TSHR structural models (according Krause et al. 2012); the extracellular fragment consist of the leucine rich repeat domain (LRRD) and hinge region.

FIG. 1: TSHR structural models (according Krause et al. 2012); the extracellular fragment consist of the leucine rich repeat domain (LRRD) and hinge region. TSH is bound between LRRD and hinge region, where sulfated Tyr385 of TSHR is bound between alpha and beta subunit of TSH. Upon TSH binding the pivotal helix and the intramolecular agonistic unit are displaced and therewith conveying the signal towards the heptahelical transmembrane domain of TSHR, here shown as second fragment. The TM domain contains an allosteric binding pocket for small molecules (shown is agonist C2, Neumann S, Krause G et al. PNAS 2009) embedded the 7 TM domain.

Figure 2:
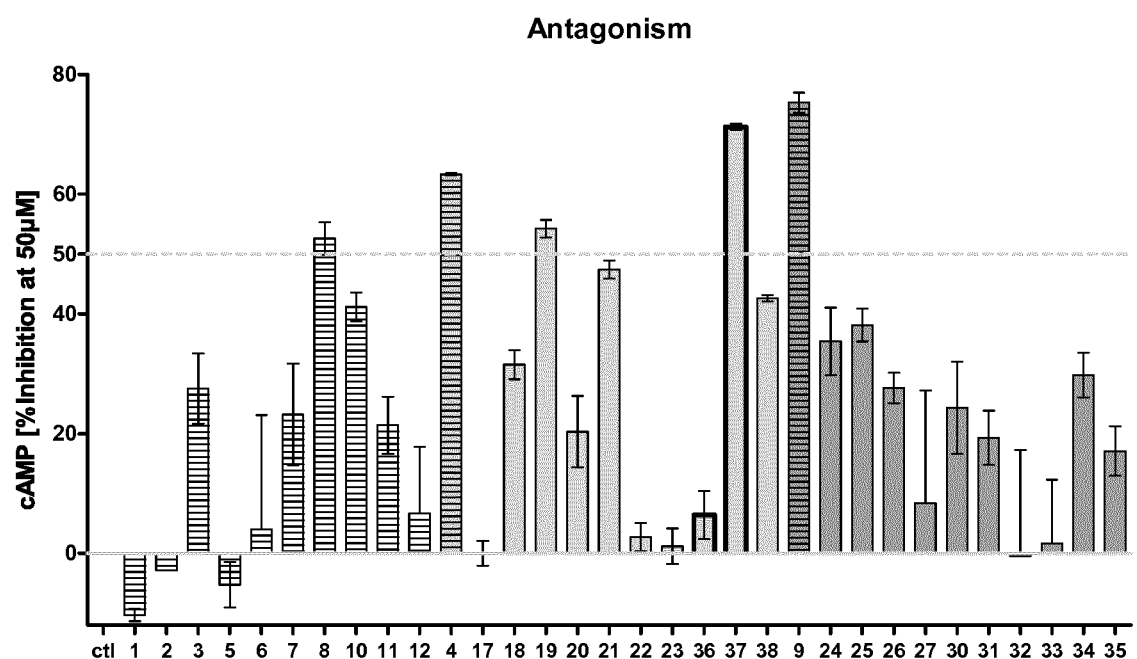
FIG. 2: Initial structure activity relationship analysis.

FIG. 2: Initial structure activity relationship analysis. Inhibition of TSH-induced cAMP production at TSHR by small molecules; measurement using RIA in HEK-293 cells. Shown are tested 38 compounds (see table 2) resulted from i) primary HTS-screen (fasciated), ii) initial secondary screen (white), iii) derivatives with similar scaffold of S4 (light grey), and of S9 (dark grey). Stereoselective synthesis of stereoisomers with successful functional separation are S36 and S37 (thick border). Threshold of 50% inhibition is indicated (dashed line).

Figure 3:
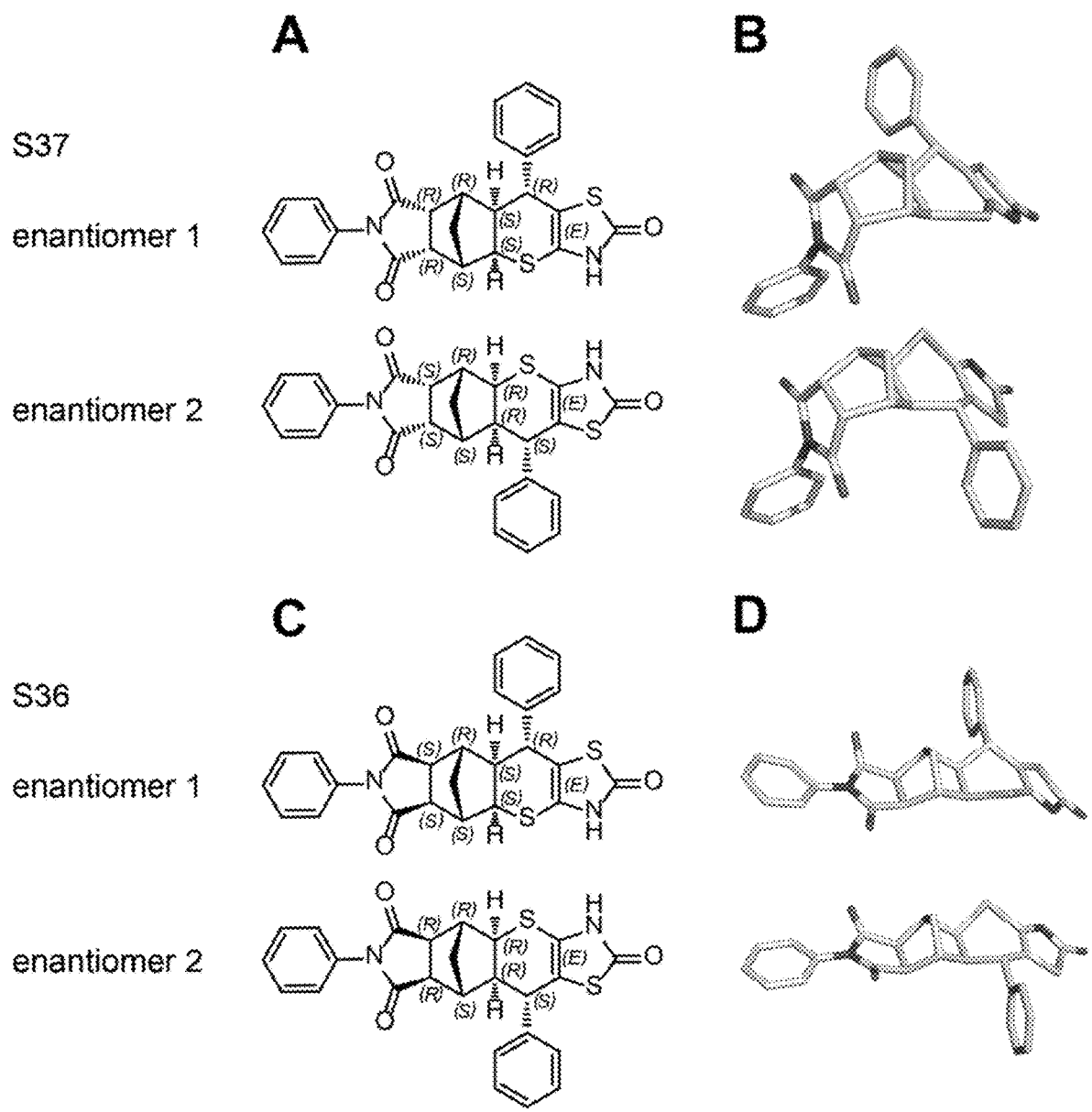
FIG. 3: Sterioisomers S37 and S36, shown as enantiomers.

FIG. 3: Stereoisomers S37 and S36. Shown are the chemical structure (A, C) as well as 3-D structures of (B) bend SS conformation of S37 and (D) extended RR conformations of S36. Chiral centers are annotated (S37 A, S36 C). The S37 and S36 constitute a special form of diastereoisomerism. They are endo- and exo-isomers to each other. B and D clearly show the difference in the conformation of compounds which explains the different behavior in blocking cAMP production.

Figure 4:
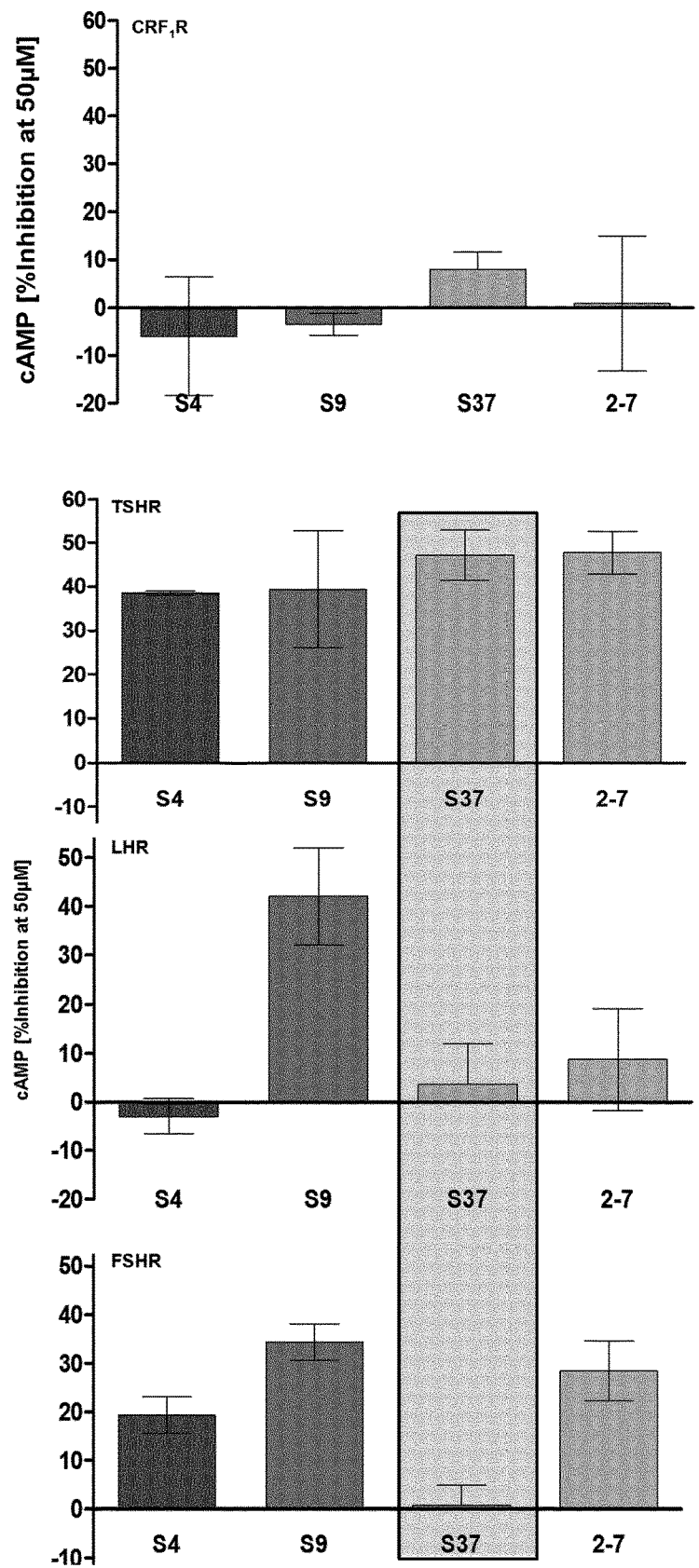
FIG. 4: Antagonistic effect (% cAMP inhibition) on TSHR and homologous receptors LHCGR and FSHR.

FIG. 4: Antagonistic effect (% cAMP inhibition) on TSHR and homologous receptors LHCGR and FSHR. Compound S4 inhibits TSHR and FSHR activation, S9 unspecifically inhibits all three receptors, while S37 inhibits TSHR comparable to the reference compound 2-7(NIH). However, S37 is highly TSHR-selective (high-lighted), while 2-7 exhibits also an effect on FSHR. Inhibition on CRF1R (left panel) was used as negative control. cAMP accumulation was measured using RIA in HEK-293 cell line stably expressing tested receptors. For compound structures see table 1.

Figure 5:
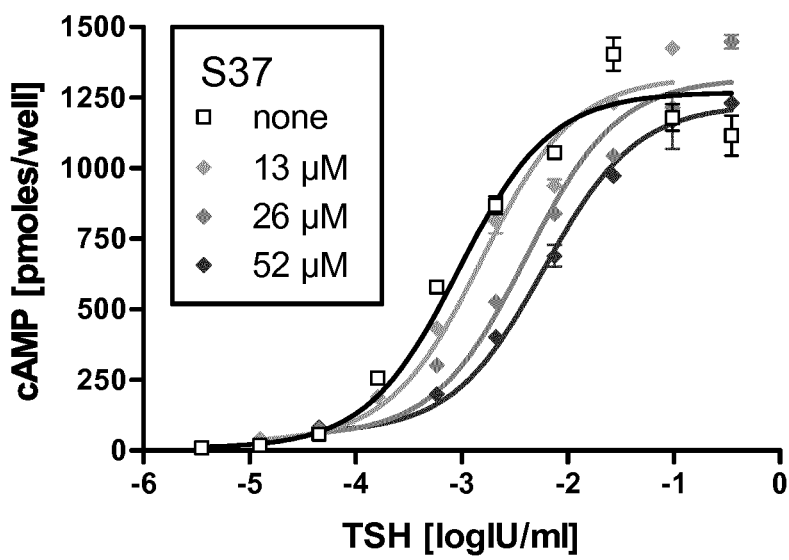
FIG. 5: Schild-Regression-Analysis
Figure 5:
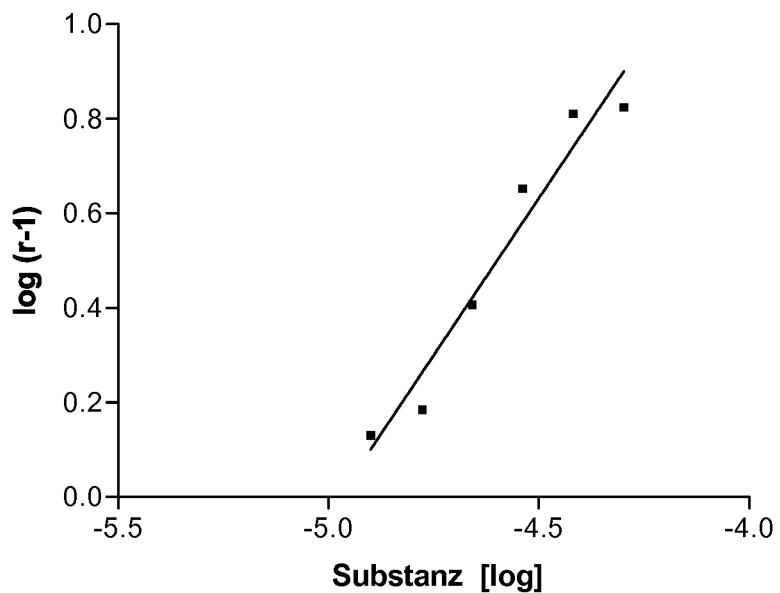
Figure 5:
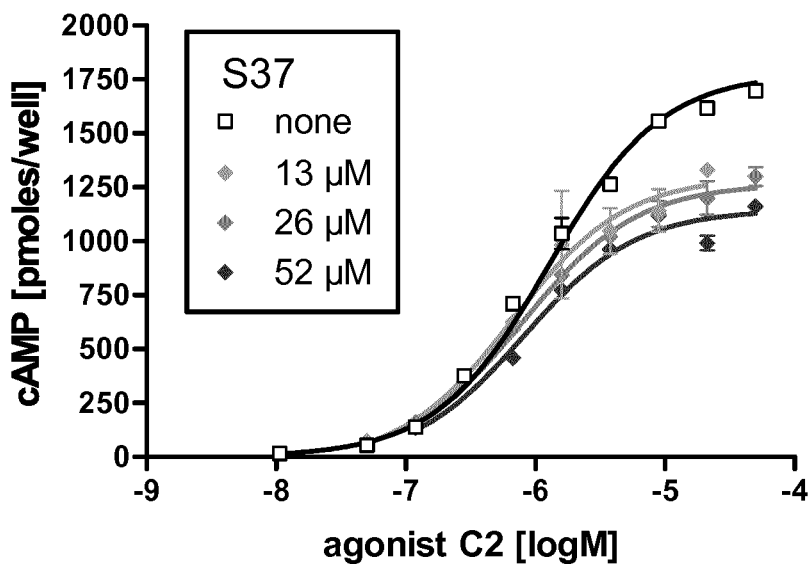
Figure 5:
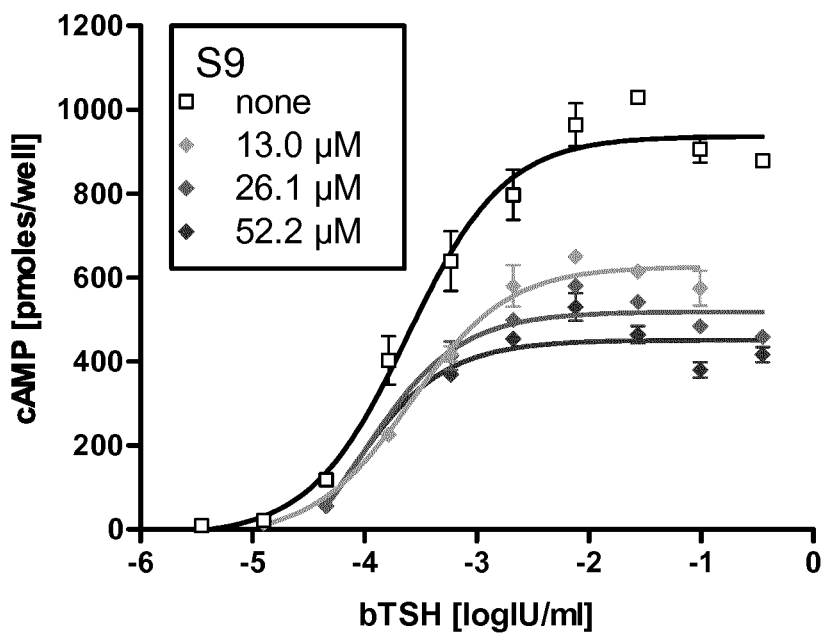
Figure 5:
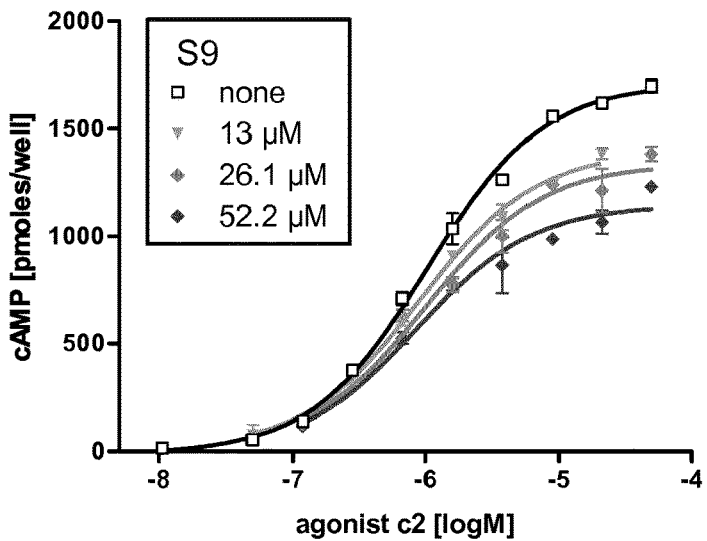

FIG. 5: Results for wt TSHR. A) TSHR cAMP stimulation by TSH with increasing concentration of S37. B) Schild-Regression-Analysis; bTSH resulting in a linear Schild-Plot indicating competitive antagonism of S37 vs. TSH. C) cAMP stimulation by compound C2; dose response curve with stepwise addition of S37 in increasing concentrations indication non-competitive antagonism of S37 vs C2 at the wildtype TSHR. D) cAMP stimulation by bTSH with increasing concentrations of S9 indicating non-competitive antagonism of S9 vs. TSH. E) cAMP stimulation by compound C2 with increasing concentrations of S9 indicating non-competitive antagonism of S9 vs. C2. All was carried out in HEK-293 cells stably expressing TSHR. Each datapoint was determined twice. Shown is arithmetic mean and standard deviations.

Figure 6:
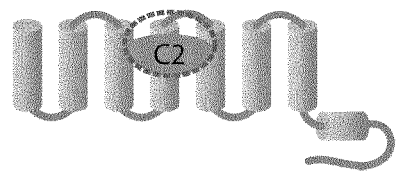
FIG. 6: Signaling patterns of S37—inhibition of truncated TSHR construct.
Figure 6:
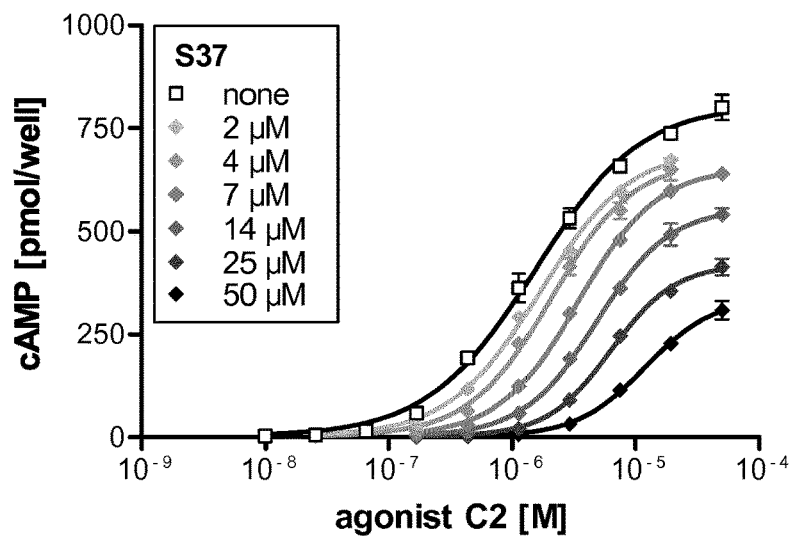

FIG. 6: Results for the truncated Δ1-408-TSHR construct lacking the ectodomain. A) Scheme of Δ1-408-TSHR, the dashed circle indicates the known allosteric binding site for the small molecule agonist compound C2 in between the transmembrane helices. B) cAMP radioimmunoassay shows a non-competitive antagonism of S37 vs. C2 indicating that S37 can also act at the transmembrane domain but elsewhere from the binding site of C2.

Figure 7:
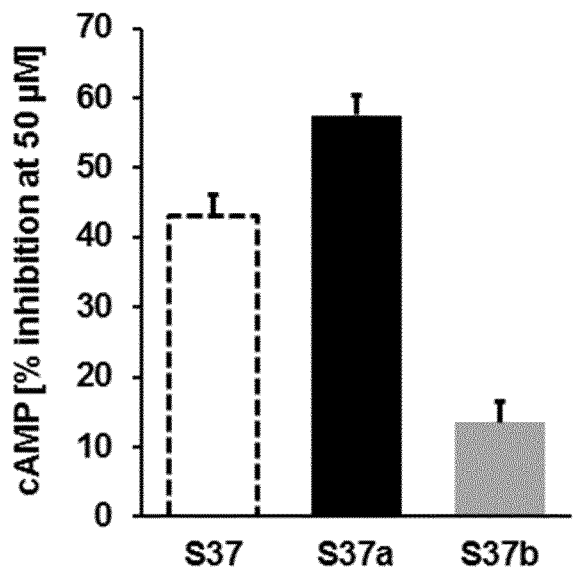
FIG. 7: S37 enantiomers.
Figure 7:
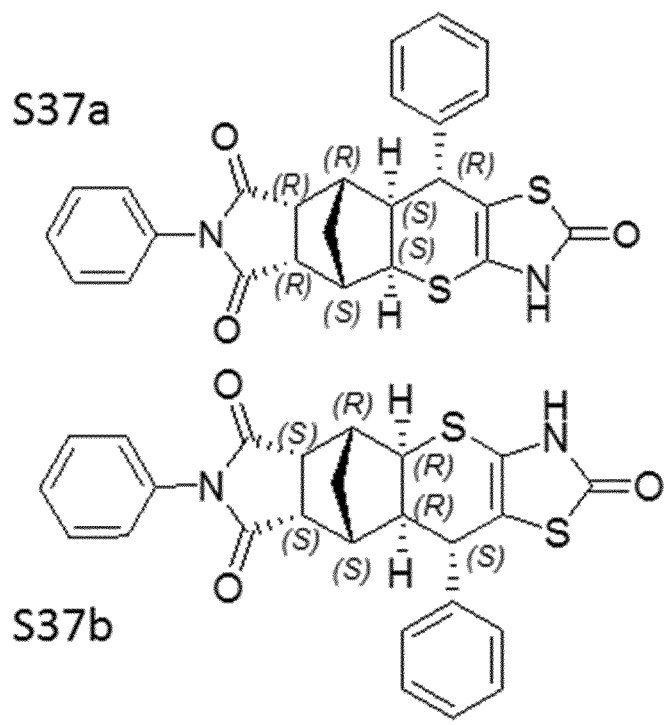
Figure 7:
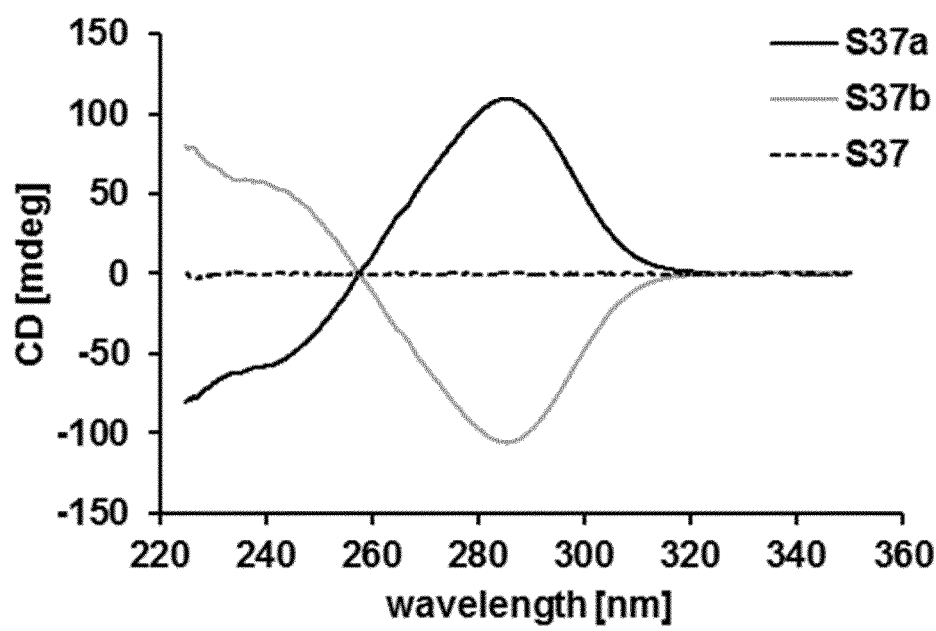
Figure 7:
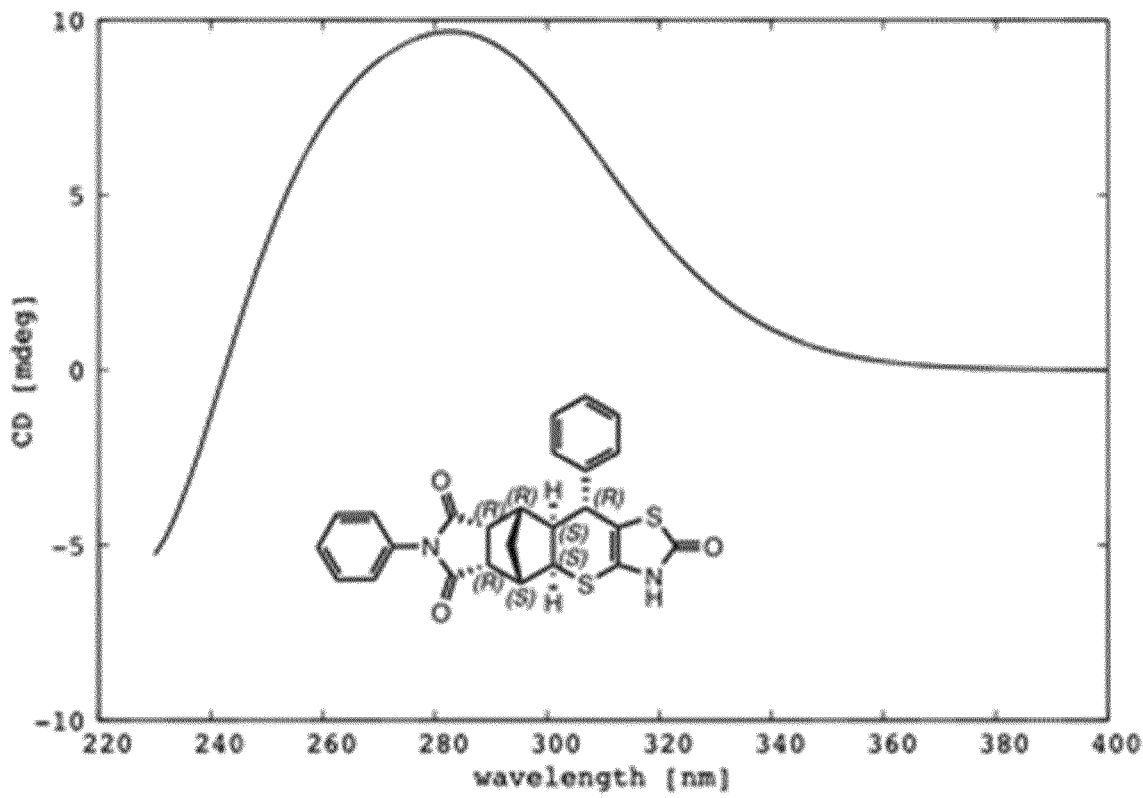

FIG. 7: S37 enantiomers. Assignment of separated enantiomer S37a to the respective formula by combination of experimental CD spectra and prediction of the spectra by time dependent DFT calculations. (A) TSHR cAMP inhibition as measured by cAMP levels (% inhibition at 50 μM) for S37, S37a and S37b employing the RIA assay. The structures of S37a and S37b enantiomers are shown. (B) Experimental circular dichroism (CD) spectrum for S37, S37a and S37b. (C) Calculated CD spectrum are shown using density functional theory (DFT) calculation.

Figure 8:
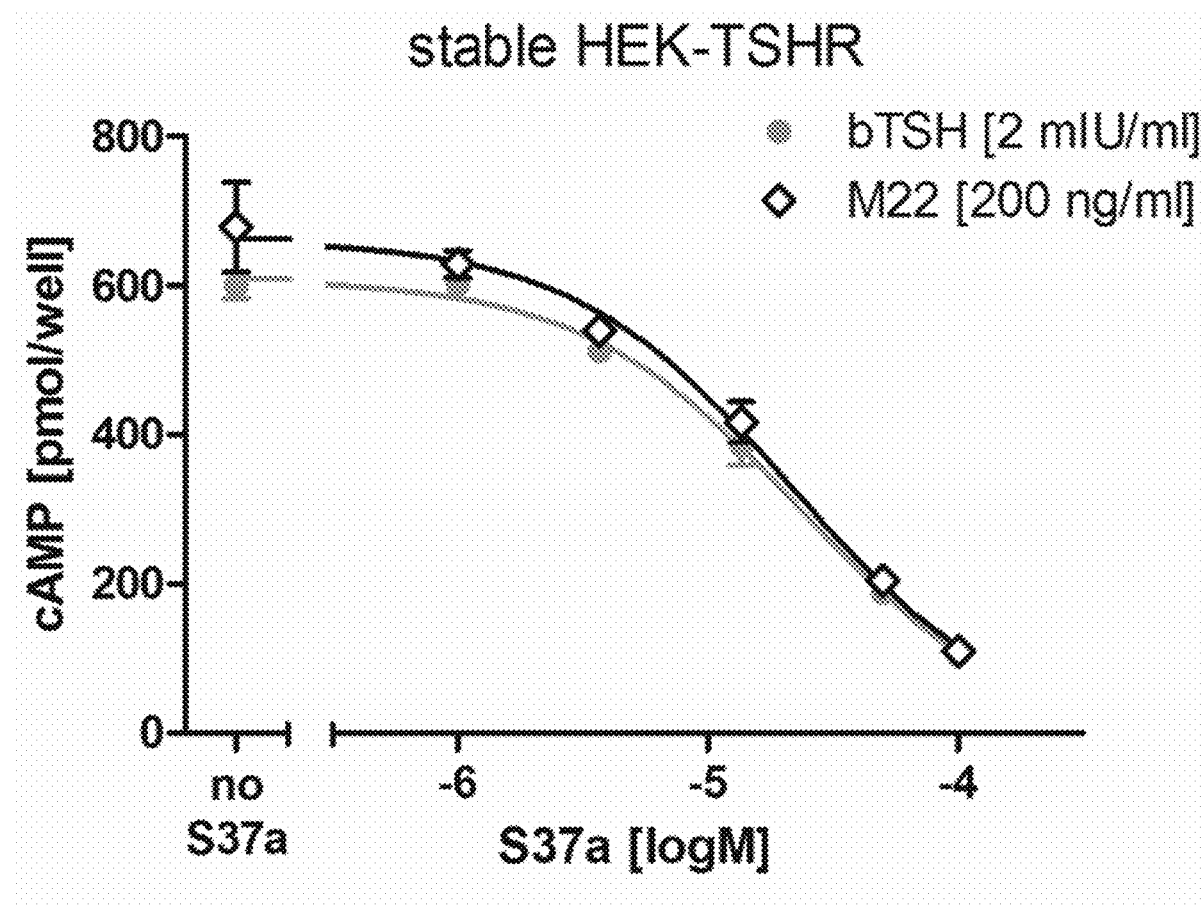
FIG. 8: Inhibition of cAMP production of TSHR induced by the monoclonal antibody M22.

FIG. 8: Inhibition of cAMP production of TSHR induced by the monoclonal antibody M22. cAMP production of TSHR induced by the monoclonal antibody M22 or the endogenous hormone TSH is inhibited by S37a.

Figure 9:
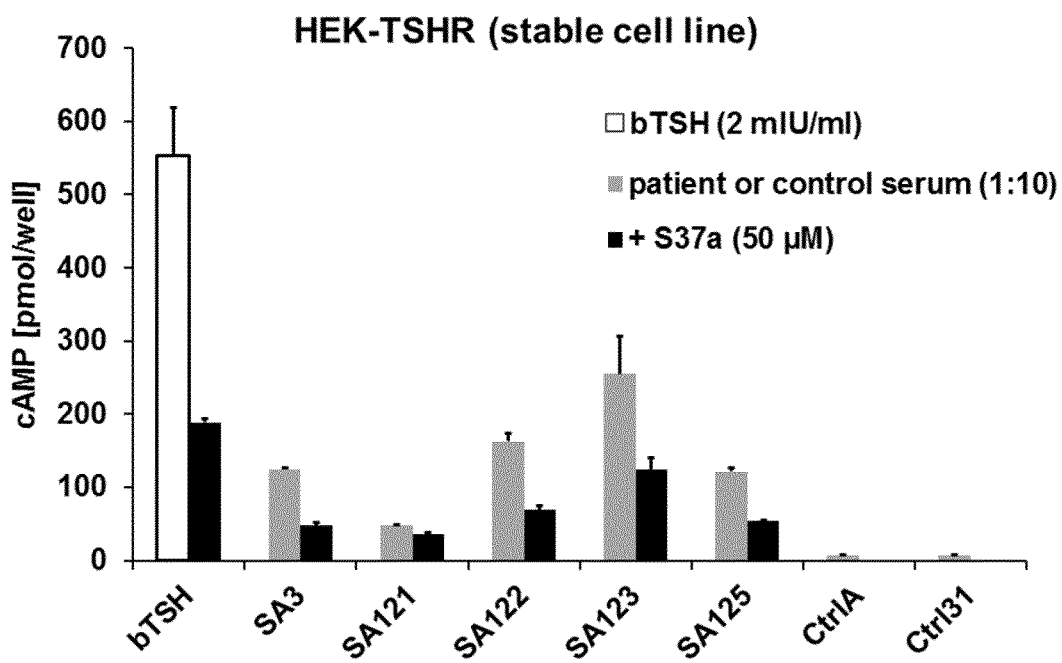
FIG. 9: Inhibition of cAMP production of TSHR induced by antibodies in sera of GO patients.

FIG. 9: Inhibition of cAMP production of TSHR induced by antibodies in sera of GO patients. cAMP production of TSHR induced by poly- or oligoclonal antibodies in sera of GO patients is inhibited by S37a. Control sera of healthy patients showed no activation and thus no inhibition.

EXAMPLES

The invention is further described by the following examples. These are not intended to limit the scope of the invention, but represent preferred embodiments of aspects of the invention provided for greater illustration of the invention described herein.

Methods Employed in the Examples

Structural Bioinformatics Generating Active and Inactive State TSHR Models to Determine Interactions for Antagonist The potential intermolecular interaction with small molecules, S9, S37 and derivatives was studied to estimate the selectivity and affinity of small molecules inside the transmembrane region and on the extracellular region. The components of the proteins and 3D QSAR were generated with the help of Sybyl software package Sybyl X2.0 (Tripos Inc., St. Louis, Mo., 63144, USA).

Docking studies of the diverse derivative molecules into the potential binding pockets of the TM Region were carried out with the program MOE. Homology models were subjected to conjugate gradient minimizations and molecular dynamics simulation of ligand receptor interaction by using the AMBER 7.0 force field. The quality and stability of the model was validated by checking the geometry using PROCHECK.

N-Terminally Truncated Construct of TSHR

Ectodomain-truncated TSHR construct (Δ1-408-TSHR.GFP) was generated using quick change site-directed mutagenesis and restriction digestion to excise the desired fragment of the TSHR sequence. The DNA sequence encoding the truncated TSHR mutant was inserted into the GFP-N1 vector. The construct was fused C-terminally with GFP and N-terminally with a FLAG tag. The FLAG tag was inserted by overlap-extension PCR. A HEK-293 cell line stably expressing this construct was generated. Shortly, cells were transfected with Polyethylenimine and plasmid DNA in a 2:1 ratio in serum free medium (DMEM). Cells were selected with medium containing 400 μg/ml G418 for several weeks and then a polyclonal population was selected for GFP fluorescence in a cell sorting device (BD FACSAria II flow cytometer). Cell surface expression was confirmed by confocal laser-scanning microscopy (GFP fluorescence) and flow cytometry using anti-FLAG M2 (Sigma).

Determination of cAMP Accumulation

HEK-293 cells stably expressing TSHR, FSHR, LHGCR or $CRF_1R$ were cultured for 48 h and stimulated for 1 h at 37° C. with stimulation buffer (DMEM supplemented with 10 mM HEPES, 0.5% BSA, 0.25 mM 3-isobutyl-1-methylxanthine) containing the ligands as indicated. After stimulation medium was aspirated and reactions were stopped by lysis of the cells with 0.1% trifluoroacetic acid, 0.005% Triton X-100 for 30 min at 4° C. Supernatants were collected and heated at 95° C. for 10 min, dried in a rotation vacuum concentrator (Alpha-RCV, Christ) and finally stored at −20° C. until use. After reconstitution and acetylation of the samples (Jäschke et al. 2006), the cAMP content was determined using cAMP-$^{125}$I-tyrosyl methyl ester (10,000 cpm, IBL) and polyclonal rabbit anti cAMP antibodies. The radioactivity of the precipitate was determined in a γ-counter.

Screening Method:

Primary screening was performed using an Enzyme Fragment Complementation (EFC) technology. CHO-K1-TSHR cells (15000/well in a 384 well plate) were treated with 50 μM of each of the 16544 compounds of the ChemBioNet compound library of the Leibniz-Institut fuer Molekulare Pharmakologie (FMP), Berlin, Germany. EFC technology uses two fragments of one enzyme: an enzyme acceptor (EA) and an enzyme donor (ED). ED is labeled to (synthetic) cAMP. Separately, these fragments are inactive, but in solution they rapidly complement to form the active enzyme, which can hydrolyze the substrate to produce a luminescent signal. In this assay, free cAMP from cell lysates and ED-labeled cAMP compete for antibody binding sites. Unbound ED-cAMP is free to complement EA to form active enzyme, which subsequently produces a luminescent signal. Thus the luminescence signal increases with rising level of intracellular cAMP. All assay components were used after the manufacturer's protocol.

Hits were validated by dose-response curves using the EFC assay.

False-positive hits could be excluded by stimulating CHO-K1 cells without TSHR with Forskolin (23.4 μM) followed by addition of the compound of interest. Forskolin activates the Adenylyl-cyclase directly. Inhibition of this effect excludes the interaction between TSHR and compound.

For the Secondary Screening cAMP accumulation was measured by radioimmunoassay (RIA) in HEK-293-TSHR cells as described before.

Results of the Examples

Homology Modeling of TSHR and Docking for Lead Optimization: Characterizing Structural Aspects of TSHR by Combining in Silico and In Vitro Approaches:

Prior to experimental verification of a ligand binding site by mutagenesis, it was necessary to study the localization of residues that come into consideration by in silico structural inspections. To date there are no crystal structures for the full GPHRs available. Initially we considered only fragmented models for the TSHR.

Later on, when the crystal structures for the N-terminal extracellular hormone binding region of the FSH bound ectodomain of the FSHR receptor were published (Jiang et al. 2012), we have applied the new structural insights to the TSHR by generating a homologous structural model of the TSHR LRRD/hinge-region/TSH complex (FIG. 1). Therewith we suggested an extracellular activation mechanism. Hormone-induced displacements of specific hinge region fragments trigger conformational changes at an "intramolecular agonistic unit" in the C-terminus of the ectodomain (confirmed by Brüser et al. JBC 2015) that is likely to convey the signal towards the seven transmembrane (7TM) domain of GPHRs and finally via G-proteins into the cell (Krause et al. 2012).

Utilizing the recent rise in crystal structure data for 7TM domains of GPCRs offers new opportunities for the characterization of the transmembrane binding pockets at various GPCRs (Gloriam et al. 2009). Generating homology models of those receptors not having crystal structures (such as also GPHRs) we provided a web resource of G-protein-coupled receptor template predictions and homology model generation (Worth et al. 2011; Worth et al. 2009).

In silico structural modeling and in vitro experimental functional characterization of model guided mutations served structural verification and led to the identification of interaction partners between both the ligand and its receptor. The GPCR structures available at that time contained a highly conserved proline at TMH5 position 5.50 causing a backbone twist in the helix structure. In contrast, TSHR exhibits at the corresponding position an alanine. Our mutation results of TSHR-(A593$^{5.50}$P) and other TMH5 residues suggests that TSHR has instead of a twist, a regular alpha helical conformation in TMH5, which also relocate some residues to different positions that are interacting with neighbouring helices or are participating differently at the transmembrane binding pocket. Thus we refined our transmembrane domain model of TSHR accordingly (Kleinau, Hoyer, et al. 2011).

Thereafter, this TMH5 conformation in our model was confirmed by crystal structures of another GPCR not having a proline at position 5.50, as well (Zhang et al. 2014). Switching agonism to antagonism and vice versa by changing either SM or residues covering the binding pocket within the transmembrane region of TSHR provides detailed knowledge about discriminative pharmacophores at TSHR and for ligands (Hoyer et al. 2013). It prepares the basis for rational optimization of new antagonists to interfere with the pathological activation of the TSHR.

High Throughput Screening for TSHR Antagonists, Validation Experiments

In order to identify new molecular scaffolds of small molecules that are able to block the TSHR activation, we established cell based screening experiments starting with a library of about 16544 compounds. The ChemBioNet library was used, which is thoroughly compiled to reach maximal scaffold variance by considering the world drug index.

For the implementation of the primary screen the Enzymes Fragment Complementation Technology (EFC) was selected. The completion of the primary screening including hit validation (dose response curves) and exclusion of false positive hits (dose dependence and test in TSHR absence) resulted in 12 compounds potentially abolishing cAMP production induced by the hormone thyrotropin, two of them are demonstrated in table 2 (S4 and S9).

For the secondary screening we used a very sensitive in vitro technique, the radioimmunoassay. This assay was established and performed in HEK-293 cell line stably expressing TSHR.

Therefore RIA was used to measure the cAMP accumulation upon stimulation with TSH ($EC_{80}$ value) and confirmed the desired effect for S4 and S9 with a clear decrease of cAMP production.

The generated response curves for compounds S4, S37 (stereoisomer derivative of S4), S9, and the internal reference compound 2-7 (known to be an inverse TSHR agonist, Neumann et al. 2014) showed dose-dependent inhibition of cAMP production caused by TSH ($EC_{80}$ value). The calculated $IC_{50}$ values are 18.69 µM for S9 and 48.9 µM for S4 (table A).

TABLE A

The $IC_{50}$ values determined in secondary screen (RIA)

| Substance | $IC_{50}$ |
|---|---|
| S4 | 48.96 µM |
| S9 | 18.62 µM |
| S37 | 27.97 µM |
| S2/7 | 10.70 µM |

In order to assess structure activity relationships further derivatives of S4 and derivatives of S9 (table 2) were tested. The desired effect was obtained for the derivatives, although none of them showed a better antagonistic activity at TSHR than their parental compounds S4 and S9 (FIG. 2). Thus initial general structure activity relationships could be drawn from the various derivatives.

TABLE 2

Results of compounds: antagonistic effects on TSHR inhibiting cAMP stimulation by TSH determined by radioimmunoassay.

| ID | antagonistic activity (% inhibition) |
|---|---|
| S4 | 63 |
| S9 | 75 |
| S18 | 30 |
| S19 | 50 |
| S20 | 50 |
| S21 | 55 |
| S26 | 35 |
| S30 | 20 |
| S34 | 30 |
| S35 | 15 |
| S36 | 0 |
| S37 | 70 |
| S38 | 40 |
| S79 | 29 |
| S80 | 25 |
| S87 | 29 |
| S89 | 22 |
| S90 | 53 |
| S96 | 34 |
| S100 | 34 |
| S122 | 38 |
| S124 | 22 |
| S125 | 34 |

Stereoselective Synthesis Resulted in S37

Since the screened and tested molecules were only available as racemates, and our rational modelling-based docking approach indicates favoured enantiomeres, we developed a stereo-selective synthesis of a few selected compounds as an initial probe. For the parental compound S4, three additional stereoselective substances (S36, S37, S38, table 2) and for the other parental compound S9, two stereoselective derivatives (S34, S35, table 2) were tested (FIG. 2).

Indeed, two of these chiral selective compounds S36 and S37 exhibit a clear separation of the functional effect. The SS-endo-stereoisomer S37 has an antagonistic effect of 70%, whereas the second isomer, which is in RR-exo-conformation does not have an antagonistic effect at all. This is confirmed by compound S38, however exhibiting the same stereoisomerism as compound S37 (FIG. 2). FIG. 3 highlights the conformational difference of the two stereoisomers. S36 exhibits an extended whereas S37 takes up a bended conformation that is responsible for its selective function.

Further 17 derivatives (S79-S128) of S37 were synthesized (table 1) of which most show also inhibition of TSH-induced cAMP accumulation, but no more than S37. The strongest inhibition (53%) of these derivatives showed S90 (table 2).

Selectivity Test Versus Homologous or Related Target Proteins

The antagonistic activity of compounds S4, S9, S37 and as reference compound, the micromolar inverse agonist 2-7 (Neumann et al. 2010) were tested on homologous members of the glycoprotein hormone receptor family, FSHR and LHCGR. As a negative control the $CRF_1R$ (Corticotropin-releasing factor 1 Receptor), a GPCR of family B was tested as well. All receptors were stably expressed in HEK-293 cells and the impact of each substance was measured upon administration of 50 µM together with the respective agonist. cAMP accumulation was quantified by RIA. The antagonistic potential of each compound was calculated. For the negative control ($CRF_1R$) no antagonistic behaviour was observed. The reference substance 2-7 exhibits, as expected, no activity at either CRF$_1$R or LHCGR. The antagonistic effect in cAMP inhibition upon hormone stimulation for TSHR is observed for compound S37 in the low micromolar range comparable to the reference substance 2-7. However we observed a significant inhibitory effect of 2-7 also on the FSHR (FIG. 4).

Schild Plot Analysis Indicates that S37 but not S9 is Competing with TSH

Moreover, a Schild plot analysis provided first interesting hints that S37 might compete with the binding site of TSH, since increasing concentrations of added S37 led to a right shift of the TSH dose response curve (FIG. 5A) and to a linear Schild plot (FIG. 5B). S37 seems not to compete with the transmembrane binding site of the previous reported agonist compound 2 (Neumann et al. 2009), since increasing concentrations of added S37 led to diminished maximal values of the dose response curve for compound 2 by unchanged EC$_{50}$ value (FIG. 5C).

Nonetheless another scaffold of our antagonistic compounds, S9 shows neither competitive behaviour with the binding site of C2 nor to that of TSH (FIGS. 5 D and E). In contrast to S9, S37 seems rather to interact with the extracellular domain competing with TSH. In summary, S37 probably interacts at the extracellular part of the receptor and is highly TSHR specific while S9 blocks also LHCGR and FSHR activation by the respective hormone (FIGS. 4 and 5).

Narrowing Down the Binding Sites for S37

Since the results of the Schild plot analysis (FIG. 5) pointed to a probable extracellular binding site of the S37 the inventors set out to clarify whether S37 is indeed binding to the extracellular domain or to the transmembrane region of TSHR. Therefore, an ectodomain-truncated TSHR construct related a previous report (Vlaeminck-Guillem et al. 2002) was generated (FIG. 6). This short construct (Δ1-408-TSHR.GFP) only consists of the transmembrane region (FIG. 6 A). As the truncated receptor lacks the hormone binding LRRD it should not be activated by TSH. Cells expressing the construct were treated with the SM agonist, compound 2, which is known to bind within the TM domain (Neumann et al. 2009). The mutant was activated by compound 2 though to a lesser extent than the wild type receptor. This was a prerequisite for further inhibition studies with the antagonist S37.

The effect of S37 was tested in the truncated construct and wt TSHR in combination with the agonist compound 2. S37 was capable of inhibiting the compound-2-induced cAMP accumulation also in the short TMD construct. However, the Schild plot indicates that in the truncated TSHR construct S37 is inhibiting cAMP activation that is induced by the small agonist C2, but is not competing with C2 within the transmembrane binding pocket (FIG. 6 B). From this data it may be concluded that S37 can bind on the transmembrane domain elsewhere of the binding pocket of agonist C2. Considering the fact that in case of the full length TSHR receptor S37 seems to compete with TSH (according the Schild plot), it indicates that S37 potentially binds in between the extracellular loops of TSHR where TSH might interact at least indirectly.

Toxicity Tests of the Compounds

The stereoisomer S37 which exhibits a TSHR selective antagonistic effect was tested for its toxicity. The vitality of the cells was measured by the alamar blue test using Hek293 cell line stably expressing TSHR. Untreated cells and DMSO-treated cells (0.2% DMSO) were used as control.

The concentration-dependent (10 μM-100 μM) toxicity test did not reveal any toxic effect for the cells upon treatment with the substances. Therefore, we conclude that substance S37 is not toxic for the concentration range evaluated by this assay.

Molecular Assignment of the Bioactive Enantiomer S37a

S37 was separated into its enantiomers S37a and S37b using chiral chromatography. The TSHR receptor was stably expressed in HEK-293 cells and the impact of each substance was measured upon administration of 50 μM together with the respective agonist. cAMP accumulation was quantified by RIA. The antagonistic potential of each compound was calculated. The two separated enantiomers S37a and S37b differ in their cAMP inhibition induced by TSH on TSHR. S37a is the more effective TSHR antagonist, while S37b show a lesser activity (FIG. 7A).

The assignment of the two enantiomers to the respective formula was possible by combining results of experimental circular dicroism (CD) spectroscopy (FIG. 7B) with predictions of CD spectra for the two enantiomers by time dependent DFT calculations (FIG. 7C), which corresponds to the respective formula representing the effective TSHR antagonist S37a.

S37a Inhibits cAMP Stimulation by Monoclonal Antibody M22 and Sera of GO Patients Of particular relevance in the present invention is the treatment of autoimmune Graves' disease and especially Graves' ophthalmopathy (GO), which are triggered by autoantibodies that are acting on TSHR at the same site as the endogenous hormone TSH. Thus the inventors have demonstrated that TSHR inhibition of cAMP stimulation induced by either monoclonal antibody M22 or by the sera of GO patients that contain autoimmune polyclonal antibodies.

The TSHR receptor was stably expressed in HEK-293 cells and the impact of each substance was measured upon administration of 50 μM together with the respective agonist, in this case either the monoclonal antibody M22 or by the sera of GO patients. cAMP accumulation was quantified by RIA. The antagonistic potential of each compound was calculated.

As is shown in FIG. 8, S37a inhibits the cAMP stimulation of TSHR caused by the monoclonal antibody M22 in the same manner as S37a inhibits the hormone TSH.

In the next step towards in vivo evidence of the desired TSHR antagonistic effect of S37a, the inventors tested sera obtained from GO patients that contain polyclonal antibodies, which pathogenically activate the TSHR. According to FIG. 9, the data indicate that S37a is able to block the pathogenic cAMP production caused by polyclonal antibodies in sera of GO patients by almost 50%. In control sera of healthy patients no activation is evident, such that no inhibition is detectable in this assay.

In Vivo Test of S37/S37a in a Mouse Model of Graves' Ophthalmopathy (GO)

The compounds of the present invention are tolerated in mouse models. The bioavailability in blood, distribution of the compound in diverse organs and the kinetics of S37a are investigated in a suitable model. Suitable mouse models for TSHR hyperthyroidism are described in Holthoff H-P et al (Endocrinology 2015; 156: 1577-89) and in Banga J et al (Horm Metab Res 2015; 47: 797-803). Pathogenic parameters of the eye are investigated employing the mouse models described above in order to show a therapeutic effect of the tested compounds.

Concluding Remarks

In summary, after pinpointing residue features for antagonist interactions at the TSHR itself, screening for TSHR antagonists as SM and initial SAR approaches we have observed different antagonistic effects for two different chemical scaffolds of the hit compounds:

S4 at TSHR and FSHR;

S9 likely interacts in the transmembrane region of TSHR, as a pure antagonist, but is not selective, acting also at LHCGR and FSHR; Compound S9 shows pure antagonistic activity in a micromolar range, however also to LHR and FSHR.

S37 (stereo selective isomer of S4) is exclusively selective for TSHR and exhibits inhibitory capacity equal to the inverse agonist 2-7 (as reference compound) in micromolar range, but 2-7 has also an antagonistic cross reactivity effect at FSHR (FIG. 4). S37 may compete with TSH (FIG. 5) indicating a different interaction site than for C2 and S9.

Two separated enantiomers of S37 (S37a and S37b) differ in their cAMP inhibition induced by TSH on TSHR. S37a is the more effective TSHR antagonist, while S37b shows less activity.

S37a shows an effect on the TSHR evident by inhibition of cAMP stimulation when induced by (i) monoclonal antibody M22 or (ii) by sera of GO patients that contain autoimmune polyclonal antibodies.

S37 and S37a are the first compounds known to the inventors with antagonistic properties which is both effective and exclusively selective at the TSHR and competes with TSH. It could not have been expected from the art that compounds of this structure show sufficient TSHR antagonism, as evident by blocking TSHR activation by stimulating autoantibodies) to enable a therapeutic effect in the treatment of hyperthyroidism.

Chemical Synthesis 1.1 General Outline of the Synthetic Steps Carried Out to Produce the Backbone Structure According to Formula I:

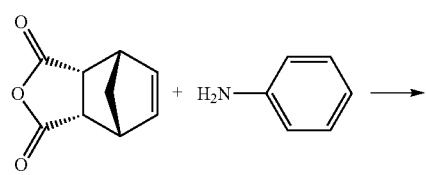

EtOAc, 18 h, RT; then NaOAc, Ac₂O, 1 h, reflux.

1.2 General Outline of the Synthetic Steps Carried Out to Produce a Potential Substituent at R4 and R5 of Formula I (Present in the Structural Backbone of Formula II):

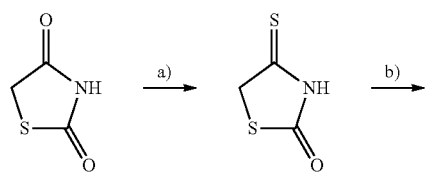

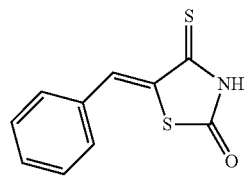

a) 1.0 eq. Lawesson-reagent, 1,4-dioxane, 4 h, reflux.
b) 1.0 eq. PhCHO, 1.0 eq. NaOAc, 4 h, reflux 1.3 General Outline of the Synthetic Steps Carried Out to Produce the Compounds According to Formula I and III:

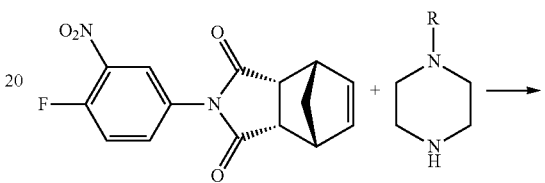

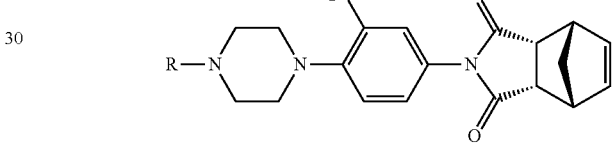

DMF, Na₂CO₃

1.4 General Outline of the Synthetic Steps Carried Out to Produce the Compounds According to Formula I and II, Using the Potential Substituent at R4 and R5 of Formula I According to Formula

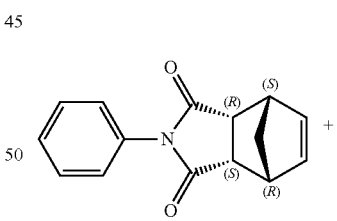

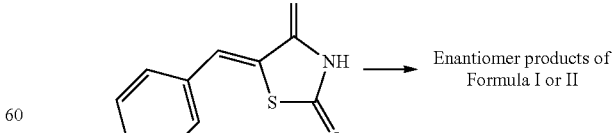

AcOH, hydrochinone, 1 h reflux

A Structural Characterization of the Components is Provided Below:

(3aR,4S,7R,7aS)-2-phenyl-3a,4,7,7a-tetrahydro-1H-4,7-methanoisoindole-1,3(2H)-dione

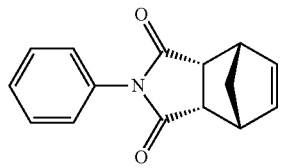

¹H-NMR (300 MHz, d6-DMSO): δ 7.49-7.34 (m, 3H), 7.09 (d, J=7.2 Hz, 2H), 6.25-6.20 (m, 2H), 3.50-3.46 (m, 2H), 3.40-3.30 (m, 2H, overlay H₂O-peak), 1.62-1.58 (m, 2H).
HRMS (ESI-TOF): m/z calculated C15H13NO2 [M+H]⁺ 240.1019 found 240.1012.

(3aR,4S,7R,7aS)-2-(4-fluoro-3-nitrophenyl)-3a,4,7,7a-tetrahydro-1H-4,7-methanoisoindole-1,3(2H)-dione

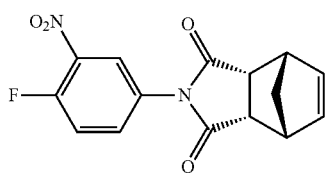

¹H-NMR (300 MHz, d6-DMSO): δ 7.96 (dd, J=2.5, 6.9 Hz, 1H), 7.70 (dd, J=8.9, 11.0 Hz, 1H), 7.60 (ddd, J=2.4, 4.2, 8.9 Hz, 1H), 6.27-6.22 (m, 2H), 3.53 (dd, J=1.3, 2.6 Hz, 2H), 3.37-3.32 (m, 2H), 1.64-1.57 (m, 2H).
HRMS (ESI-TOF): m/z calculated für C15H11FNO2 [M+H]⁺ 303.0776 found 303.0796.

(3aR,4R,7S,7aS)-2-(4-fluoro-3-nitrophenyl)-3a,4,7,7a-tetrahydro-1H-4,7-methanoisoindole-1,3(2H)-dione

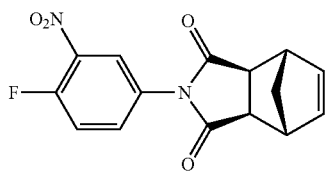

¹H-NMR (300 MHz, d6-DMSO): δ 8.19 (dd, J=2.5, 6.8 Hz, 1H), 7.80 (ddd, J=2.5, 4.4, 8.9 Hz, 1H), 7.73 (dd, J=8.9, 10.8 Hz, 1H), 6.37-6.34 (m, 2H), 3.23-3.19 (m, 2H), 2.86 (s, 2H), 1.51 (d, J=10.0 Hz, 1H), 1.44 (d, J=10.0 Hz, 1H).
HRMS (ESI-TOF): m/z calculated für C15H11FNO2 [M+H]⁺ 303.0776 found 303.0796.

4-Thioxo-thiazolidin-2-on

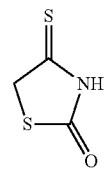

¹H-NMR (300 MHz, d6-DMSO): δ 13.51 (s, 1H), 4.59 (s, 2H).

5-Aryliden-4-thioxo-thiazolidin-2-on

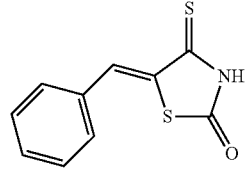 [SMILES: O=C1NC(=S)/C(=C/c2ccccc2)S1]

¹H-NMR (300 MHz, d6-DMSO): δ 13.89 (s, 1H), 8.09 (s, 1H), 7.71-7.64 (m, 2H), 7.57-7.51 (m, 3H).
HRMS (ESI-TOF): m/z calculated C10H7NOS2 [M+H]⁺ 222.0042, found 222.0050.

Both Enantiomer Products of the Synthesis Described Under 1.1-1.4 were Separated Using Chiral Chromatography:

(4aS,5S,5aR,8aR,9R,9aS,10R)-7,10-diphenyl-3,4a,5,5a,8a,9,9a,10-octahydro-5,9-methanothiazolo[5',4':5,6]thiopyrano[2,3-f]isoindole-2,6,8(7H)-trione (S37)

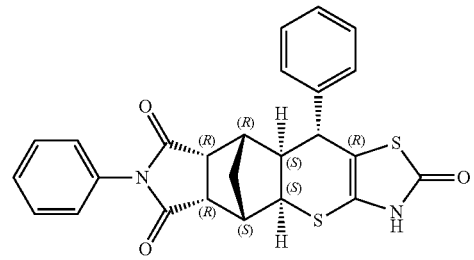

(4aR,5R,5aR,8aR,9S,9aR,10S)-7,10-Diphenyl-5,5a,8a,9,9a,10-hexahydro-5,9-methanthiazolo[5',4':5,6]thiopyrano[2,3-f]isoindol-2,6,8(3H,4aH,7H)-trion (S37)

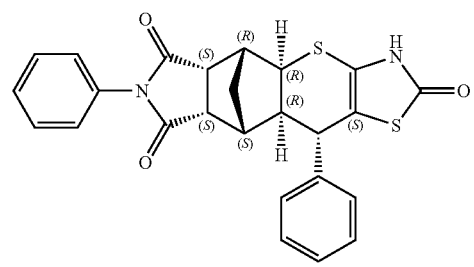

¹H-NMR (300 MHz, CDCl3): δ 9.52 (s, 1H), 7.55-7.47- (m, 2H), 7.46-7.33 (m, 4H), 7.28-7.21 (m, 4H), 3.61-3.51 (m, 2H), 3.42 (dd, J=5.4, 9.7 Hz, 1H), 3.27 (dd, J=5.3, 9.5 Hz, 1H), 2.93-2.86 (m, 1H), 2.73 (d, J=5.2 Hz, 1H), 2.61 (d, J=10.8 Hz, 1H), 2.41 (t, J=9.1 Hz, 1H), 1.73 (d, J=10.7 Hz, 1H).

HRMS (ESI-TOF): m/z calculated C$_{25}$H$_{20}$N$_2$O$_3$S$_2$ [M+H]$^+$ 461.0988 found 461.1003.

The Following Diastereomers were Shown to be Inactive and Due to Lack of Activity the Racemic Mixture was not Separated into its Enantiomers:

(4aS,5S,5aS,8aS,9R,9aS,10R)-7,10-diphenyl-3,4a,5, 5a,8a,9,9a,10-octahydro-5,9-methanothiazolo[5',4':5, 6]thiopyrano[2,3-f]isoindole-2,6,8(7H)-trione (S36)

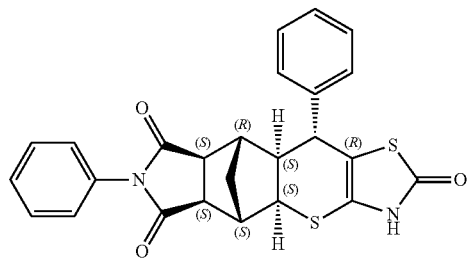

(4aR,5R,5aR,8aR,9S,9aR,10S)-7,10-diphenyl-3,4a,5, 5a,8a,9,9a,10-octahydro-5,9-methanothiazolo[5',4':5, 6]thiopyrano[2,3-f]isoindole-2,6,8(7H)-trione (S36)

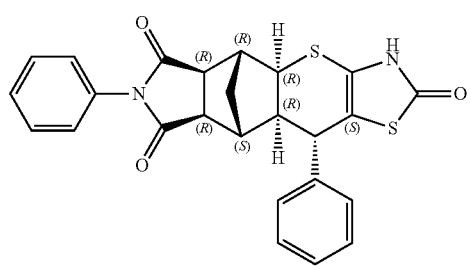

¹H-NMR (300 MHz, CDCl3): δ 10.69 (s, 1H), 7.42-7.18 (m, 8H), 7.15-7.05 (m, 2H), 3.51 (t, J=7.4 Hz, 1H), 3.45-3.34 (m, 1H), 2.87 (t, J=7.2 Hz, 1H), 2.79-2.63 (m, 2H), 2.59-2.47 (m, 1H), 2.40-2.22 (m, 2H), 1.32 (d, J=12.0 Hz, 1H).

HRMS (ESI-TOF): m/z calculated C$_{25}$H$_{20}$N$_2$O$_3$S$_2$[M+ H]$^+$ 461.0988 found 461.1001.

A Number of Further Derivatives According to Formulae I and II were Synthesized Based on the General Outlines Provided Above Under 1.1-1.4 Using Appropriate Starting Materials:

(4aS,5S,5aR,8aR,9R,9aS,10R)-7-(4-(4-methylpiper-azin-1-yl)-3-nitrophenyl)-10-phenyl-3,4a,5,5a,8a,9, 9a,10-octahydro-5,9-methanothiazolo[5',4':5,6]thio-pyrano[2,3-f]isoindole-2,6,8(7H)-trione (S38)

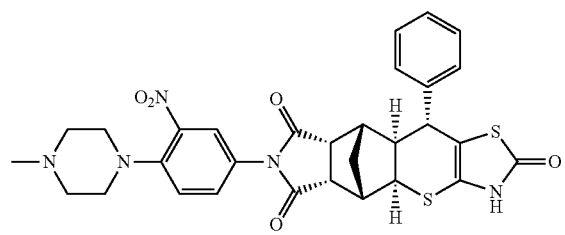 [SMILES: CN1CCN(c2ccc(N3C(=O)[C@@H]4[C@H]5C[C@H]([C@@H]6Sc7[nH]c(=O)sc7[C@@H](c7ccccc7)[C@H]56)[C@@H]4C3=O)cc2[N+](=O)[O-])CC1]

(4aR,5R,5aS,8aS,9S,9aR,10 S)-7-(4-(4-Methylpiper-azin-1-yl)-3-nitrophenyl)-10-phenyl-5,5a,8a,9,9a,10-hexahydro-5,9-methanthiazolo[5',4':5,6]thiopyrano [2,3-f]isoindol-2,6,8(3H,4aH,7H)-trion (S38)

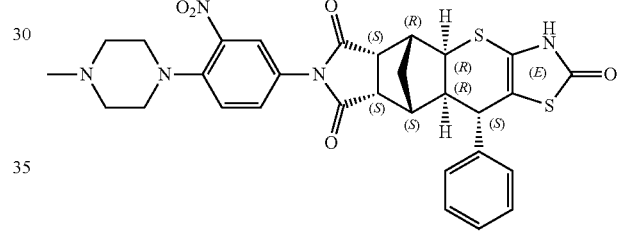

¹H-NMR (300 MHz, d$_6$-DMSO): δ 11.49 (s, 1H), 7.83 (d, J=2.4 Hz, 1H), 7.53 (dd, J=2.4, 8.8 Hz, 1H), 7.39 (s, 1H), 7.37-7.30 (m, 5H), 3.60-3.53 (m, 2H), 3.45 (dd, J=5.5, 9.7 Hz, 1H), 3.32-3.26 (m, 2H, overlay H$_2$O-peak), 3.08-3.00 (m, 4H), 2.74-2.69 (m, 1H), 2.54-2.51 (m, 1H), 2.38-2.33 (m, 1H), 2.21 (s, 3H), 1.75-1.67 (m, 1H).

HRMS (ESI-TOF): m/z calculated C$_{30}$H$_{29}$N$_5$O$_5$S$_2$[M+ H]$^+$ 604.1683 found 604.1685.

(4aR,5R,5aS,8aS,9S,9aR,10S)-7-(4-aminophenyl)-10-phenyl-3,4a,5,5a,8a,9,9a,10-octahydro-5,9-methanothiazolo[5',4':5,6]thiopyrano[2,3-f]isoin-dole-2,6,8(7H)-trione Compound with (4aS,5S,5aR, 8aR,9R,9aS,10R)-7-(4-aminophenyl)-10-phenyl-3, 4a,5,5a,8a,9,9a,10-octahydro-5,9-methanothiazolo [5',4':5,6]thiopyrano[2,3-t]isoindole-2,6,8(7H)-trione (1:1) (S79)

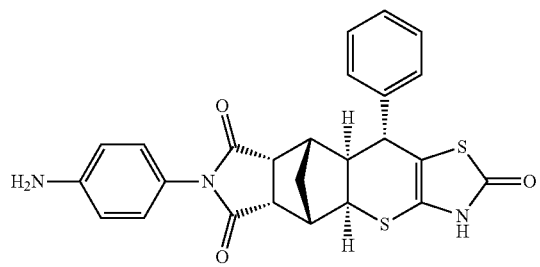

-continued

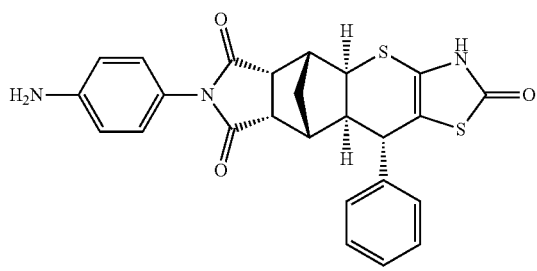

HRMS (ESI-TOF): m/z calculated $C_{25}H_{21}N_3O_3S_2$ [M+H]$^+$ 476.1097 found 476.1083.

methyl 4-((4aR,5R,5aS,8aS,9S,9aR,10S)-2,6,8-trioxo-10-phenyl-3,4a,5,5a,6,8,8a,9,9a,10-decahydro-5,9-methanothiazolo[5',4':5,6]thiopyrano[2,3-f]isoindol-7(2H)-yl)benzoate compound with methyl 4-((4aS,5S,5aR,8aR,9R,9aS,10R)-2,6,8-trioxo-10-phenyl-3,4a,5,5a,6,8,8a,9,9a,10-decahydro-5,9-methanothiazolo[5',4':5,6]thiopyrano[2,3-f]isoindol-7(2H)-yl)benzoate (1:1)(S87)

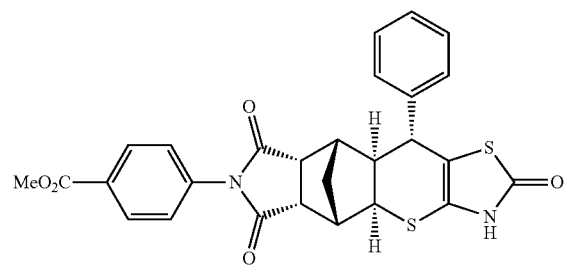

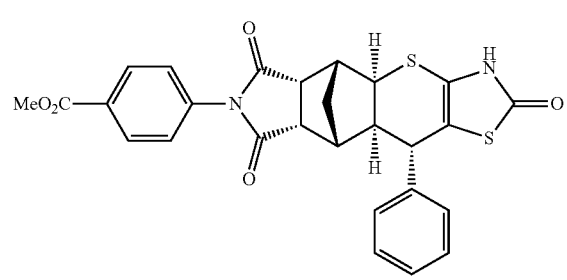

$^1$H NMR (300 MHz, d$_6$-DMSO) δ 11.56 (s, 1H), 8.07 (d, J=8.4 Hz, 2H), 7.51 (d, J=8.4 Hz, 2H), 7.36 (m, 5H), 3.88 (s, 3H), 3.63-3.46 (m, 3H), 3.32 (m, 1H, overlay H$_2$O-peak), 2.75 (d, J=5.4 Hz, 1H), 2.55-2.45 (m, 1H, overlay DMSO-peak), 2.43-2.31 (m, 2H), 1.72 (d, J=10.4 Hz, 1H).

HRMS (ESI-TOF): m/z calculated $C_{27}H_{22}N_2O_4S_2$ [M+H]$^+$ 519.1043 found 519.1049.

(4aR,5R,5aS,8aS,9S,9aR,10S)-7-(4-acetylphenyl)-10-phenyl-3,4a,5,5a,8a,9,9a,10-octahydro-5,9-methanothiazolo[5',4':5,6]thiopyrano[2,3-f]isoindole-2,6,8(7H)-trione Compound with (4aS,5S,5aR,8aR,9R,9aS,10R)-7-(4-acetylphenyl)-10-phenyl-3,4a,5,5a,8a,9,9a,10-octahydro-5,9-methanothiazolo[5',4':5,6]thiopyrano[2,3-f]isoindole-2,6,8(7H)-trione (1:1)(S80)

$^1$H NMR (300 MHz, d$_6$-DMSO) δ 11.55 (s, 1H), 8.06 (d, J=8.5 Hz, 2H), 7.49 (d, J=8.5 Hz, 2H), 7.42-7.30 (m, 5H), 3.60 (d, J=10.1 Hz, 1H), 3.57-3.48 (m, 2H), 3.41-3.29 (m, 1H, overlay H$_2$O-peak), 2.75 (d, J=5.7 Hz, 1H), 2.61 (s, 3H), 2.55-2.45 (m, 1H, overlay DMSO-peak) 2.42 (d, J=5.3 Hz, 1H), 2.35 (t, J=8.9 Hz, 1H), 1.73 (d, J=10.5 Hz, 1H).

HRMS (ESI-TOF): m/z calculated $C_{27}H_{22}N_2O_4S_2$ [M+H]$^+$ 503.1094 found 503.1075.

(4aR,5R,5aS,8aS,9S,9aR,10S)-10-phenyl-7-(p-tolyl)-3,4a,5,5a,8a,9,9a,10-octahydro-5,9-methanothiazolo[5',4':5,6]thiopyrano[2,3-f]isoindole-2,6,8(7H)-trione Compound with (4aS,5S,5aR,8aR,9R,9aS,10R)-10-phenyl-7-(p-tolyl)-3,4a,5,5a,8a,9,9a,10-octahydro-5,9-methanothiazolo[5',4':5,6]thiopyrano[2,3-f]isoindole-2,6,8(7H)-trione (1:1) (S90)

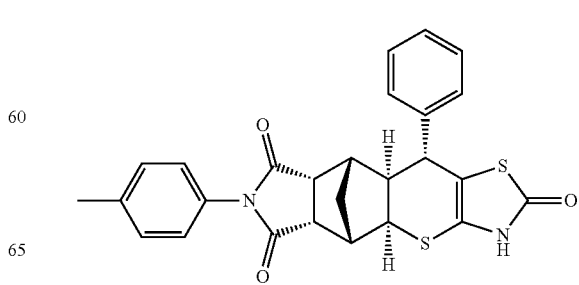

-continued

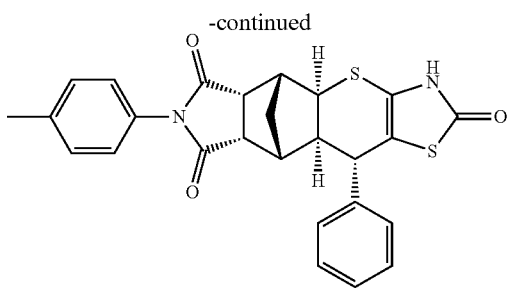

¹H NMR (300 MHz, Chloroform-d) δ 9.04 (s, 1H), 7.44-7.36 (m, 3H), 7.35-7.30 (m, 2H), 7.25 (d, J=6.9 Hz, 2H), 7.14 (d, J=8.3 Hz, 2H), 3.57 (d, J=9.7 Hz, 2H), 3.42 (dd, J=5.3, 9.7 Hz, 1H), 3.28 (dd, J=5.3, 9.6 Hz, 1H), 2.90 (d, J=5.6 Hz, 1H), 2.74 (d, J=5.3 Hz, 1H), 2.62 (d, J=10.8 Hz, 1H), 2.45-2.37 (m, 4H), 1.74 (d, J=10.9 Hz, 1H).

HRMS (ESI-TOF): m/z calculated $C_{26}H_{22}N_2O_3S_2$[M+H]$^+$ 475.1145 found 475.1137.

(4aR,5R,5aS,8aS,9S,9aR,10S)-7-(4-methoxyphenyl)-10-phenyl-3,4a,5,5a,8a,9,9a,10-octahydro-5,9-methanothiazolo[5',4':5,6]thiopyrano[2,3-t]isoindole-2,6,8(7H)-trione compound with (4aS,5S,5aR,8aR,9R,9aS,10R)-7-(4-methoxyphenyl)-10-phenyl-3,4a,5,5a,8a,9,9a,10-octahydro-5,9-methanothiazolo[5',4':5,6]thiopyrano[2,3-t]isoindole-2,6,8(7H)-trione (1:1) (S89)

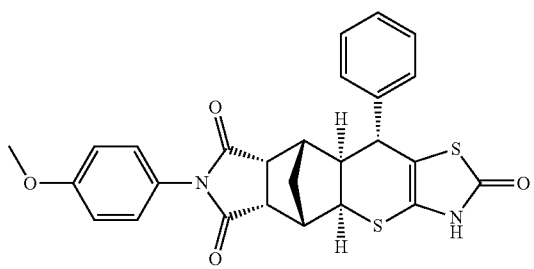

¹H NMR (300 MHz, Chloroform-d) δ 7.44-7.34 (m, 3H), 7.25 (d, J=7.2 Hz, 2H), 7.18 (d, J=8.8 Hz, 2H), 7.03 (d, J=9.1 Hz, 2H), 3.85 (s, 3H), 3.59-3.50 (m, 2H), 3.47-3.38 (m, 1H), 3.28 (dd, J=5.2, 9.6 Hz, 1H), 2.90 (d, J=5.2 Hz, 1H), 2.74 (d, J=5.5 Hz, 1H), 2.62 (d, J=10.7 Hz, 1H), 2.44-2.35 (m, 1H), 1.72 (m, 1H, overlay H₂O-peak).

HRMS (ESI-TOF): m/z calculated $C_{27}H_{22}N_2O_4S_2$ [M+H]$^+$ 503.1094 found 503.1075.

methyl 3-((4aR,5R,5aS,8aS,9S,9aR,10S)-2,6,8-trioxo-10-phenyl-3,4a,5,5a,6,8,8a,9,9a,10-decahydro-5,9-methanothiazolo[5',4':5,6]thiopyrano[2,3-f]isoindol-7(2H)-yl)benzoate compound with methyl 3-((4aS,5S,5aR,8aR,9R,9aS,10R)-2,6,8-trioxo-10-phenyl-3,4a,5,5a,6,8,8a,9,9a,10-decahydro-5,9-methanothiazolo[5',4':5,6]thiopyrano[2,3-f]isoindol-7(2H)-yl)benzoate (1:1) (S96)

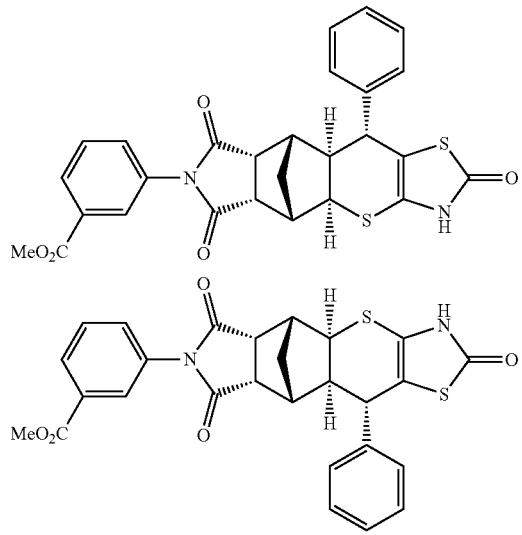

¹H NMR (300 MHz, d₆-DMSO) δ 11.55 (s, 1H), 8.03-7.97 (m, 1H), 7.90 (s, 1H), 7.70-7.64 (m, 2H), 7.41-7.31 (m, 5H), 3.86 (s, 3H), 3.58 (dd, J=9.0, 13.7 Hz, 2H), 3.49 (dd, J=5.5, 9.6 Hz, 1H), 3.39-3.29 (m, 1H, overlay H₂O-peak), 2.75 (d, J=5.6 Hz, 1H), 2.55-2.45 (m, 1H, overlay DMSO-peak), 2.44-2.32 (m, 2H), 1.73 (d, J=10.4 Hz, 1H).

HRMS (ESI-TOF): m/z calculated $C_{27}H_{22}N_2O_5S_2$ [M+H]$^+$ 519.1043 found 519.1039.

Methyl 4'-((4aR,5R,5aS,8aS,9S,9aR,10S)-2,6,8-trioxo-10-phenyl-3,4a,5,5a,6,8,8a,9,9a,10-decahydro-5,9-methanothiazolo[5',4':5,6]thiopyrano[2,3-f]isoindol-7(2H)-yl)-[1,1'-biphenyl]-3-carboxylate compound with methyl 4'-((4aS,5S,5aR,8aR,9R,9aS,10R)-2,6,8-trioxo-10-phenyl-3,4a,5,5a,6,8,8a,9,9a,10-decahydro-5,9-methanothiazolo[5',4':5,6]thiopyrano[2,3-f]isoindol-7(2H)-yl)-[1,1'-biphenyl]-3-carboxylate (1:1) (S98)

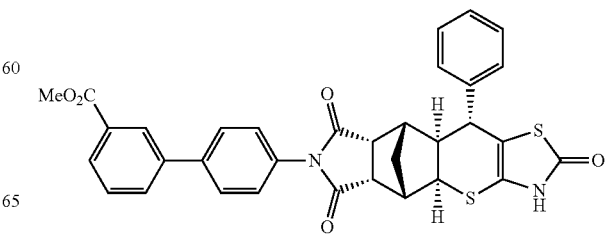

-continued

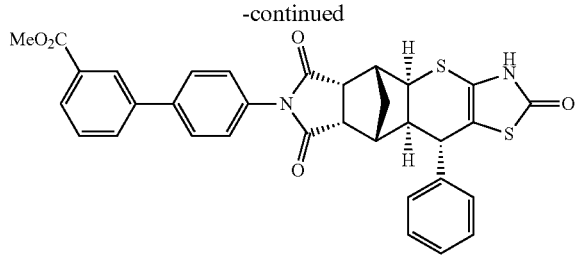

HRMS (ESI-TOF): m/z calculated $C_{33}H_{26}N_2O_5S_2$ [M+H]$^+$ 595.1356 found 595.1332.

(4aR,5R,5aS,8aS,9S,9aR,10S)-7-(2-methoxyphenyl)-10-phenyl-3,4a,5,5a,8a,9,9a,10-octahydro-5,9-methanothiazolo[5',4':5,6]thiopyrano[2,3-t]isoindole-2,6,8(7H)-trione compound with (4aS,5S,5aR,8aR,9R,9aS,10R)-7-(2-methoxyphenyl)-10-phenyl-3,4a,5,5a,8a,9,9a,10-octahydro-5,9-methanothiazolo[5',4':5,6]thiopyrano[2,3-f]isoindole-2,6,8(7H)-trione (1:1) (S99)

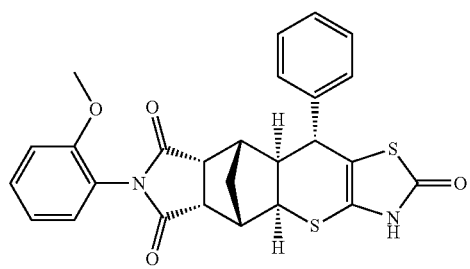

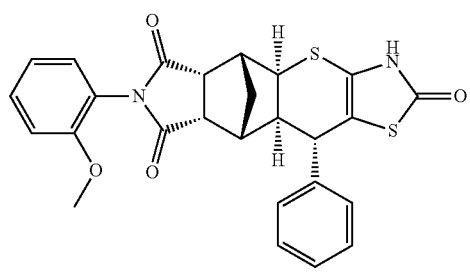

$^1$H NMR (300 MHz, d$_6$-DMSO) δ 11.67 (s, 1H), 7.51-7.43 (m, 1H), 7.36 (dd, J=7.1, 13.2 Hz, 3H), 7.27 (d, J=7.4 Hz, 2H), 7.21-7.12 (m, 2H), 7.10-7.00 (m, 1H), 3.72-3.55 (m, 2H), 3.59 (s, 3H), 3.46 (dd, J=5.5, 9.3 Hz, 1H), 3.29 (dd, J=5.3, 9.3 Hz, 1H), 2.76 (d, J=5.6 Hz, 1H), 2.62-2.54 (m, 1H), 2.54-2.45 (m, 1H, overlay DMSO-peak), 2.38 (d, J=5.6 Hz, 1H), 1.70 (d, J=10.6 Hz, 1H).

HRMS (ESI-TOF): m/z calculated $C_{26}H_{22}N_2O_4S_2$ [M+H]$^+$ 491.1094 found 491.1095.

(4aR,5R,5aS,8aS,9S,9aR,10S)-7-(4-hydroxyphenyl)-10-phenyl-3,4a,5,5a,8a,9,9a,10-octahydro-5,9-methanothiazolo[5',4':5,6]thiopyrano[2,3-f]isoindole-2,6,8(7H)-trione compound with (4aS,5S,5aR,8aR,9R,9aS,10R)-7-(4-hydroxyphenyl)-10-phenyl-3,4a,5,5a,8a,9,9a,10-octahydro-5,9-methanothiazolo[5',4':5,6]thiopyrano[2,3-f]isoindole-2,6,8(7H)-trione (1:1) (S100)

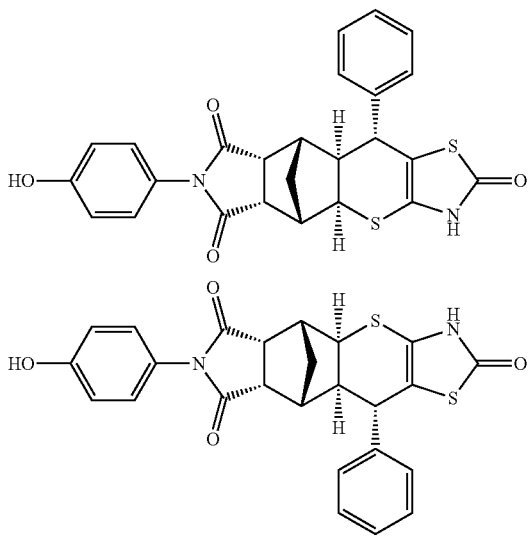

$^1$H NMR (300 MHz, d$_6$-DMSO) δ 11.56 (s, 1H), 9.75 (s, 1H), 7.43-7.28 (m, 5H), 7.06 (d, J=8.8 Hz, 2H), 6.83 (d, J=8.8 Hz, 2H), 3.59 (d, J=10.1 Hz, 1H), 3.48-3.31 (m, 3H, overlay H$_2$O-peak), 3.26 (dd, J=5.3, 9.5 Hz, 1H), 2.72 (d, J=5.7 Hz, 1H), 2.39 (d, J=5.6 Hz, 1H), 2.28 (t, J=9.0 Hz, 1H), 1.69 (d, J=10.8 Hz, 1H).

HRMS (ESI-TOF): m/z calculated $C_{25}H_{21}N_2O_4S_2$[M+H]$^+$ 477.0937 found 477.0947.

(4aR,5R,5aS,8aS,9S,9aR,10S)-7-(4-bromophenyl)-10-phenyl-3,4a,5,5a,8a,9,9a,10-octahydro-5,9-methanothiazolo[5',4':5,6]thiopyrano[2,3-t]isoindole-2,6,8(7H)-trione compound with (4aS,5S,5aR,8aR,9R,9aS,10R)-7-(4-bromophenyl)-10-phenyl-3,4a,5,5a,8a,9,9a,10-octahydro-5,9-methanothiazolo[5',4':5,6]thiopyrano[2,3-t]isoindole-2,6,8(7H)-trione (1:1) (S101)

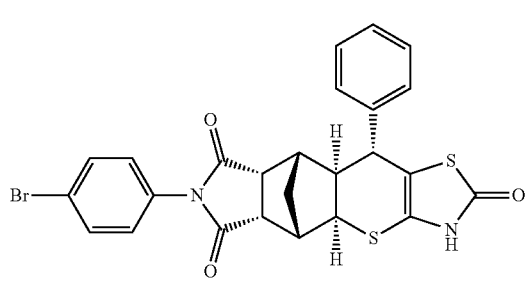

-continued

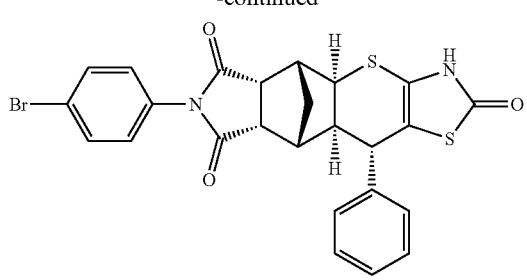

¹H NMR (300 MHz, d₆-DMSO) δ 11.54 (s, 1H), 7.70 (d, J=8.6 Hz, 2H), 7.42-7.29 (m, 7H), 3.56 (dd, J=9.2, 21.2 Hz, 2H), 3.49-3.42 (m, 1H), 3.32-3.26 (m, 1H), 2.73 (d, J=5.6 Hz, 1H), 2.55-2.45 (m, 1H, overlay DMSO-peak), 2.40 (d, J=5.4 Hz, 1H), 2.33 (t, J=9.1 Hz, 1H), 1.71 (d, J=10.5 Hz, 1H).

HRMS (ESI-TOF): m/z calculated $C_{25}H_{19}BrN_2O_3S_2$ [M+H]⁺ 539.0081/541.0078 found 539.0093/541.0063.

(4aR,5R,5aS,8aS,9S,9aR,10S)-7-([1,1'-biphenyl]-4-yl)-10-phenyl-3,4a,5,5a,8a,9,9a,10-octahydro-5,9-methanothiazolo[5',4':5,6]thiopyrano[2,3-f]isoindole-2,6,8(7H)-trione compound with (4aS,5S,5aR,8aR,9R,9aS,10R)-7-([1,1'-biphenyl]-4-yl)-10-phenyl-3,4a,5,5a,8a,9,9a,10-octahydro-5,9-methanothiazolo[5',4':5,6]thiopyrano[2,3-f] isoindole-2,6,8(7H)-trione (1:1) (S102)

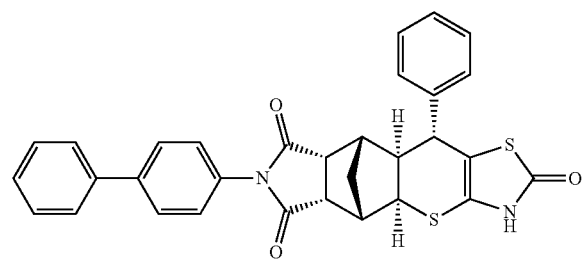

¹H NMR (300 MHz, d₆-DMSO) δ 11.56 (s, 1H), 7.77 (d, J=8.5 Hz, 2H), 7.70 (d, J=7.4 Hz, 2H), 7.55-7.45 (m, 2H), 7.44-7.30 (m, 8H), 3.62 (d, J=10.2 Hz, 1H), 3.57-3.46 (m, 2H), 3.35-3.30 (m, 1H, overlay H₂O-peak), 2.76 (d, J=5.8 Hz, 1H), 2.55-2.45 (m, 1H, overlay DMSO-peak), 2.43 (d, J=5.6 Hz, 1H), 2.40-2.31 (m, 1H), 1.73 (d, J=10.8 Hz, 1H).

HRMS (ESI-TOF): m/z calculated $C_{30}H_{24}N_2O_3S_2$ [M+H]⁺ 537.1301 found 537.1283.

(4aR,5R,5aS,8aS,9S,9aR,10S)-10-(4-methoxyphenyl)-7-phenyl-3,4a,5,5a,8a,9,9a,10-octahydro-5,9-methanothiazolo[5',4':5,6]thiopyrano[2,3-t]isoindole-2,6,8(7H)-trione compound with (4aS,5S,5aR,8aR,9R,9aS,10R)-10-(4-methoxyphenyl)-7-phenyl-3,4a,5,5a,8a,9,9a,10-octahydro-5,9-methanothiazolo[5',4':5,6]thiopyrano[2,3-f]isoindole-2,6,8(7H)-trione (1:1) (S123)

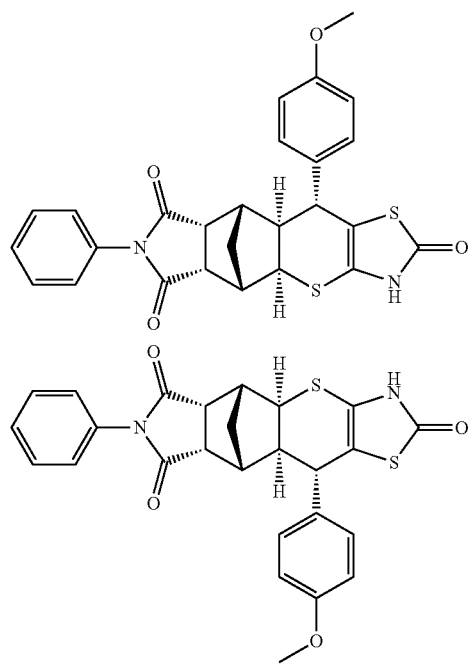

¹H NMR (300 MHz, d₆-DMSO) δ 11.53 (s, 1H), 7.46 (dd, J=7.1, 14.5 Hz, 3H), 7.28 (dd, J=8.0, 14.1 Hz, 4H), 6.93 (d, J=8.7 Hz, 2H), 3.58-3.43 (m, 3H), 3.33-3.26 (m, 1H), 2.74 (d, J=5.6 Hz, 1H), 2.55-2.45 (m, 1H, overlay DMSO-peak), 2.42 (d, J=5.5 Hz, 1H), 2.27 (t, J=9.1 Hz, 1H), 1.71 (d, J=10.6 Hz, 1H).

HRMS (ESI-TOF): m/z calculated $C_{26}H_{22}N_2O_4S_2$ [M+H]⁺ 491.1094 found 491.1094.

(4aR,5R,5aS,8aS,9S,9aR,10S)-10-(4-hydroxyphenyl)-7-phenyl-3,4a,5,5a,8a,9,9a,10-octahydro-5,9-methanothiazolo[5',4':5,6]thiopyrano[2,3-f]isoindole-2,6,8(7H)-trione compound with (4aS,5S,5aR,8aR,9R,9aS,10R)-10-(4-hydroxyphenyl)-7-phenyl-3,4a,5,5a,8a,9,9a,10-octahydro-5,9-methanothiazolo[5',4':5,6]thiopyrano[2,3-f]isoindole-2,6,8(7H)-trione (1:1) (S122)

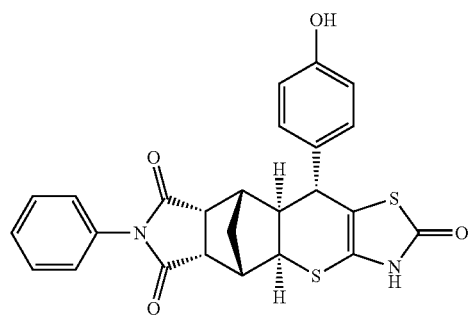

63

-continued

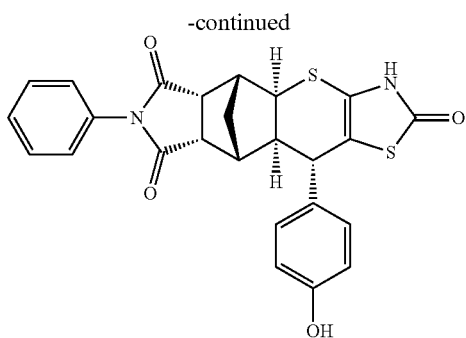

¹H NMR (300 MHz, d₆-DMSO) δ 11.50 (s, 1H), 9.47 (s, 1H), 7.47 (dd, J=7.0, 14.4 Hz, 3H), 7.29 (d, J=7.4 Hz, 2H), 7.11 (d, J=8.5 Hz, 2H), 6.74 (d, J=8.4 Hz, 2H), 3.51-3.44 (m, 3H), 3.31 (dd, J=5.3, 9.6 Hz, 1H), 2.73 (d, J=5.0 Hz, 1H), 2.50-2.39 (m, 2H, overlay DMSO-peak), 2.30-2.18 (m, 1H), 1.70 (d, J=10.2 Hz, 1H). HRMS (ESI-TOF): m/z calculated $C_{25}H_{20}N_2O_4S_2$ [M+H]⁺ 477.0937 found 477.0939.

(4aR,5R,5aS,8aS,9S,9aR,10S)-10-(4-(dimethylamino)phenyl)-7-phenyl-3,4a,5,5a,8a,9,9a,10-octahydro-5,9-methanothiazolo[5',4':5,6]thiopyrano[2,3-f]isoindole-2,6,8(7H)-trione compound with (4aS,5S,5aR,8aR,9R,9aS,10R)-10-(4-(dimethylamino)phenyl)-7-phenyl-3,4a,5,5a,8a,9,9a,10-octahydro-5,9-methanothiazolo[5',4':5,6]thiopyrano[2,3-f]isoindole-2,6,8(7H)-trione (1:1) (S121)

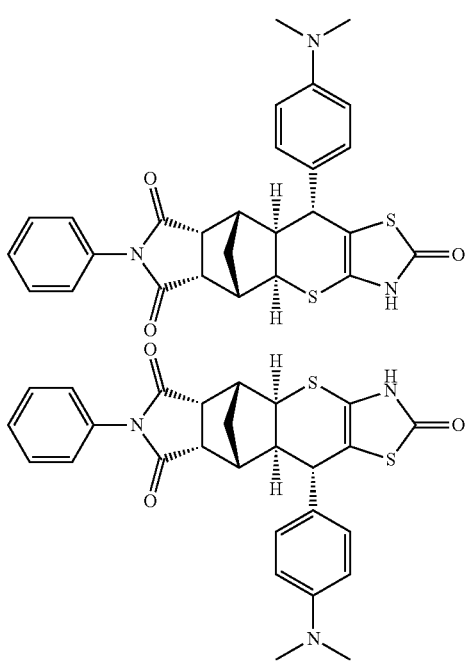

¹H NMR (300 MHz, d₆-DMSO) δ 11.49 (s, 1H), 7.47 (dd, J=7.0, 14.5 Hz, 3H), 7.29 (d, J=7.5 Hz, 2H), 7.12 (d, J=8.6 Hz, 2H), 6.72 (d, J=8.5 Hz, 2H), 3.52-3.44 (m, 3H), 3.31 (dd, J=5.3, 9.6 Hz, 1H), 2.90 (s, 6H), 2.73 (d, J=5.6 Hz, 1H), 2.55-2.45 (m, 1H, overlay DMSO-peak), 2.44 (d, J=5.6 Hz, 1H), 2.25 (t, J=9.1 Hz, 1H), 1.70 (d, J=10.5 Hz, 1H).
HRMS (ESI-TOF): m/z calculated $C_{27}H_{25}N_3O_3S_2$ [M+H]⁺ 504.1410 found 504.1412.

64

(4aR,5R,5aS,8aS,9S,9aR,10S)-10-(4-fluorophenyl)-7-phenyl-3,4a,5,5a,8a,9,9a,10-octahydro-5,9-methanothiazolo[5',4':5,6]thiopyrano[2,3-f]isoindole-2,6,8(7H)-trione compound with (4aS,5S,5aR,8aR,9R,9aS,10R)-10-(4-fluorophenyl)-7-phenyl-3,4a,5,5a,8a,9,9a,10-octahydro-5,9-methanothiazolo[5',4':5,6]thiopyrano[2,3-f]isoindole-2,6,8(7H)-trione (1:1) (S124)

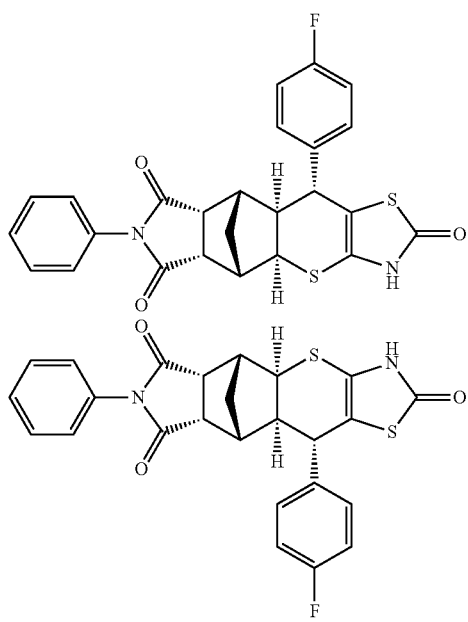

¹H NMR (300 MHz, d₆-DMSO) δ 11.57 (s, 1H), 7.52-7.39 (m, 5H), 7.31 (d, J=7.6 Hz, 2H), 7.22 (t, J=8.8 Hz, 2H), 3.65 (d, J=10.1 Hz, 1H), 3.60-3.45 (m, 1H, overlay H₂O-peak), 3.41-3.28 (m, 2H), 2.74 (d, J=5.7 Hz, 1H), 2.55-2.45 (m, 1H, overlay DMSO-peak), 2.39 (d, J=5.6 Hz, 1H), 2.30 (t, J=9.0 Hz, 1H), 1.72 (d, J=10.5 Hz, 1H).
HRMS (ESI-TOF): m/z calculated $C_{25}H_{19}FN_2O_3S_2$ [M+H]⁺ 479.0894 found 479.0915.

(4aR,5R,5aS,8aS,9S,9aR,10S)-10-(3-hydroxyphenyl)-7-phenyl-3,4a,5,5a,8a,9,9a,10-octahydro-5,9-methanothiazolo[5',4':5,6]thiopyrano[2,3-f]isoindole-2,6,8(7H)-trione compound with (4aS,5S,5aR,8aR,9R,9aS,10R)-10-(3-hydroxyphenyl)-7-phenyl-3,4a,5,5a,8a,9,9a,10-octahydro-5,9-methanothiazolo[5',4':5,6]thiopyrano[2,3-f]isoindole-2,6,8(7H)-trione (1:1) (S125)

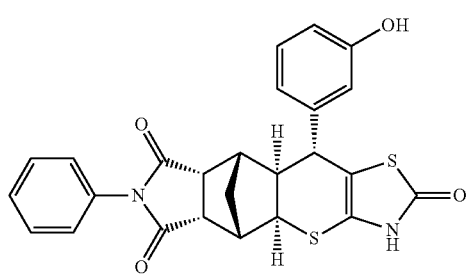

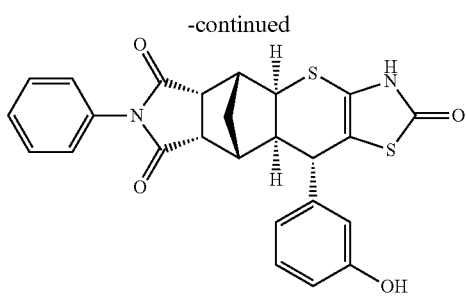

¹H NMR (300 MHz, d₆-DMSO) δ 11.57 (s, 1H), 7.52-7.38 (m, 5H), 7.31 (d, J=7.6 Hz, 2H), 7.22 (t, J=8.8 Hz, 2H), 3.65 (d, J=10.2 Hz, 1H), 3.59-3.45 (m, 1H, overlay H₂O-peak), 3.41-3.27 (m, 2H), 2.74 (d, J=5.7 Hz, 1H), 2.55-2.45 (m, 1H, overlay DMSO-peak), 2.39 (d, J=5.8 Hz, 1H), 2.30 (t, J=9.0 Hz, 1H), 1.72 (d, J=10.6 Hz, 1H).

HRMS (ESI-TOF): m/z calculated $C_{25}H_{20}N_2O_4S_2$[M+H]⁺ 477.0937 found 477.0938.

(4aR,5R,5aS,8aS,9S,9aR,10S)-7-phenyl-10-(4-(trifluoromethyl)phenyl)-3,4a,5,5a,8a,9,9a,10-octahydro-5,9-methanothiazolo[5',4':5,6]thiopyrano[2,3-f]isoindole-2,6,8(7H)-trione compound with (4aS,5S,5aR,8aR,9R,9aS,10R)-7-phenyl-10-(4-(trifluoromethyl)phenyl)-3,4a,5,5a,8a,9,9a,10-octahydro-5,9-methanothiazolo[5',4':5,6]thiopyrano[2,3-f]isoindole-2,6,8(7H)-trione (1:1) (S128)

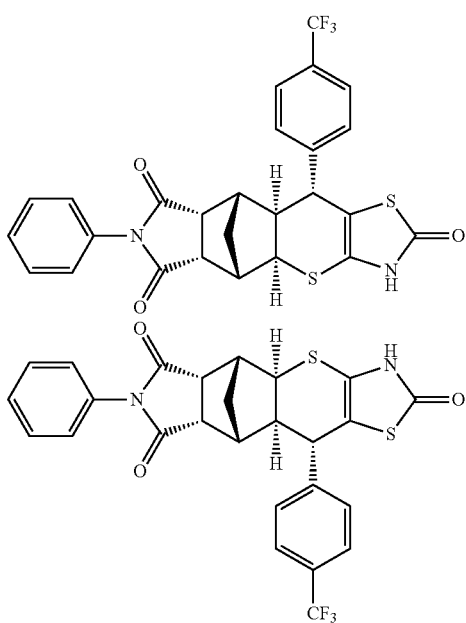

¹H NMR (300 MHz, d₆-DMSO) δ 11.63 (s, 1H), 7.78 (d, J=8.3 Hz, 2H), 7.62 (d, J=8.2 Hz, 2H), 7.53-7.40 (m, 3H), 7.32 (d, J=7.6 Hz, 2H), 3.78 (d, J=10.1 Hz, 1H), 3.54 (d, J=7.8 Hz, 1H), 3.51-3.46 (m, 1H), 3.34-3.28 (m, 1H, overlay H₂O-peak), 2.75 (d, J=5.6 Hz, 1H), 2.55-2.45 (m, 1H, overlay DMSO-peak), 2.41-2.32 (m, 1H), 1.73 (d, J=10.2 Hz, 1H). HRMS (ESI-TOF): m/z calculated $C_{26}H_{19}F_3N_2O_3S_2$ [M+H]⁺ 529.0862 found 529.0875.

A Number of Further Derivatives According to Formulae I and III were Synthesized Based on the General Outlines Provided Above Under 1.1-1.4 Using Appropriate Starting Materials:

(3aR,4S,7R,7aS)-2-(3-nitro-4-(4-phenylpiperazin-1-yl)phenyl)-3a,4,7,7a-tetrahydro-1H-4,7-methanoisoindole-1,3(2H)-dione

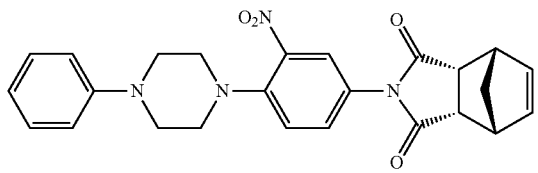 [SMILES: O=C1[C@@H]2[C@H](C(=O)N1c1ccc(N3CCN(c4ccccc4)CC3)c([N+](=O)[O-])c1)[C@@H]1C=C[C@H]2C1]

¹H-NMR (300 MHz, d6-DMSO): 7.64 (d, J=1.90 Hz, 1H), 7.43 (d, J=8.9 Hz, 1H), 7.35 (dd, J=1.9, 8.8 Hz, 1H), 7.27-7.20 (m, 2H), 6.96 (d, J=8.4 Hz, 2H), 6.85-6.75 (m, 1H), 6.24-6.21 (m, 2H), 3.51-3.48 (m, 2H), 3.40-3.30 (m, 2H overlay H₂O-peak), 3.28-3.22 (m, 4H), 3.22-3.17 (m, 4H), 1.60 (s, 2H). HRMS (ESI-TOF): m/z calculated $C_{25}H_{24}N_4O_4$ [M+H]⁺ 445.1870 found 445.1878.

(3aR,4R,7S,7aS)-2-(3-nitro-4-(4-phenylpiperazin-1-yl)phenyl)-3a,4,7,7a-tetrahydro-1H-4,7-methanoisoindole-1,3(2H)-dione

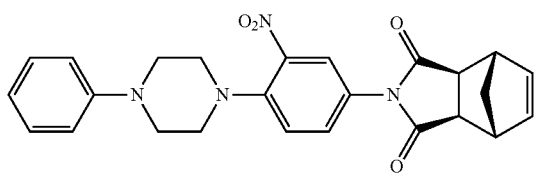 [SMILES: O=C1[C@@H]2[C@H](C(=O)N1c1ccc(N3CCN(c4ccccc4)CC3)c([N+](=O)[O-])c1)[C@H]1C=C[C@@H]2C1]

¹H-NMR (300 MHz, d6-DMSO): δ 7.84 (s, 1H), 7.52 (d, J=8.6 Hz, 1H), 7.45 (d, J=8.9 Hz, 1H), 7.27-7.18 (m, 2H), 7.00-6.94 (m, 2H), 6.85-6.75 (m, 1H), 6.35 (s, 2H), 3.30-3.24 (m, 4H), 3.23-3.17 (m, 4H, overlay H₂O-peak), 3.13-3.06 (m, 1H), 2.97-2.90 (m, 1H), 2.84 (s, 2H), 1.50-1.40 (m, 2H).

HRMS (ESI-TOF): m/z calculated $C_{25}H_{24}N_4O_4$ [M+H]⁺ 445.1870 found 445.1883.

(3aR,4S,7R,7aS)-2-(4-(4-methylpiperazin-1-yl)-3-nitrophenyl)-3a,4,7,7a-tetrahydro-1H-4,7-methanoisoindole-1,3(2H)-dione

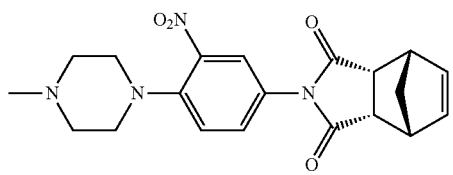 [SMILES: CN1CCN(c2ccc(N3C(=O)[C@@H]4[C@H](C3=O)[C@@H]3C=C[C@H]4C3)cc2[N+](=O)[O-])CC1]

¹H-NMR (300 MHz, d6-DMSO): δ 7.58 (d, J=1.7 Hz, 1H), 7.37-7.27 (m, 2H), 6.23-6.18 (m, 2H), 3.51-3.45 (m, 2H), 3.31 (s, 2H), 3.06-2.97 (m, 4H), 2.44-2.37 (m, 4H), 2.20 (s, 3H), 1.62-1.55 (m, 2H). HRMS (ESI-TOF): m/z calculated $C_{20}H_{22}N_4O_4$ [M+H]$^+$ 383.1714 found 383.1713.

(3aR,4R,7S,7aS)-2-(4-(4-methylpiperazin-1-yl)-3-nitrophenyl)-3a,4,7,7a-tetrahydro-1H-4,7-methanoisoindole-1,3(2H)-dione

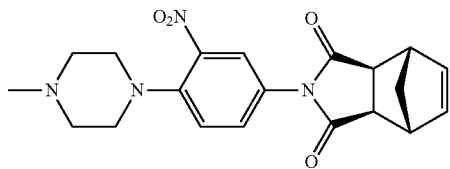 [SMILES: CN1CCN(c2ccc(N3C(=O)[C@@H]4[C@H](C3=O)[C@H]3C=C[C@@H]4C3)cc2[N+](=O)[O-])CC1]

$^1$H-NMR (300 MHz, d6-DMSO): δ 7.79 (d, J=2.4 Hz, 1H), 7.48 (dd, J=2.4, 8.8 Hz, 1H), 7.38 (d, J=8.9 Hz, 1H), 6.37-6.32 (m, 2H), 3.20-3.17 (m, 2H), 3.08-3.02 (m, 4H), 2.83 (s, 2H), 2.50-2.43 (m, 6H), 2.24 (s, 3H), 1.46-1.41 (m, 2H). HRMS (ESI-TOF): m/z calculated $C_{20}H_{22}N_4O_4$ [M+H]$^+$ 383.1714, found 383.1713.

Ethyl 4-(4-((3aR,4S,7R,7aS)-1,3-dioxo-1,3,3a,4,7,7a-hexahydro-2H-4,7-methanoisoindol-2-yl)-2-nitrophenyl)piperazine-1-carboxylate

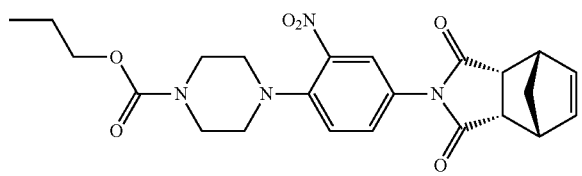 [SMILES: CCCOC(=O)N1CCN(c2ccc(N3C(=O)[C@@H]4[C@H](C3=O)[C@@H]3C=C[C@H]4C3)cc2[N+](=O)[O-])CC1]

$^1$H-NMR (300 MHz, d6-DMSO): δ 7.63 (d, J=2.3 Hz, 1H), 7.39 (d, J=8.8 Hz, 1H), 7.34 (dd, J=2.4, 8.8 Hz, 1H), 6.23-6.19 (m, 2H), 4.05 (q, J=7.1 Hz, 2H), 3.51-3.45 (m, 6H), 3.27-3.22 (m, 1H), 3.04-2.99 (m, 4H), 2.63-2.57 (m, 1H), 1.63-1.55 (m, 2H), 1.18 (t, J=7.1 Hz, 3H). HRMS (ESI-TOF): m/z calculated $C_{22}H_{24}N_4O_6$ [M+H]$^+$ 441.1769 found 441.1772.

Ethyl 4-(4-((3aR,4R,7S,7aS)-1,3-dioxo-1,3,3a,4,7,7a-hexahydro-2H-4,7-methanoisoindol-2-yl)-2-nitrophenyl)piperazine-1-carboxylate

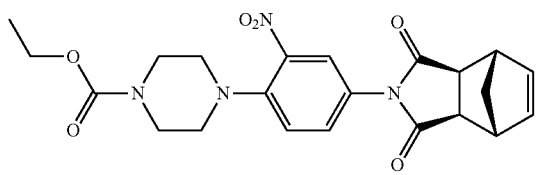 [SMILES: CCOC(=O)N1CCN(c2ccc(N3C(=O)[C@@H]4[C@H](C3=O)[C@H]3C=C[C@@H]4C3)cc2[N+](=O)[O-])CC1]

HRMS (ESI-TOF): m/z calculated $C_{22}H_{24}N_4O_6$ [M+H]$^+$ 441.1769 found 441.1781.

REFERENCES

Bahn, R. S., 2010. Graves' ophthalmopathy. The New England journal of medicine, 362(8), pp. 726-38.

Bartalena, L., 2013. Graves' orbitopathy: imperfect treatments for a rare disease. European thyroid journal, 2(4), pp. 259-69.

Bartalena, L., 2011. The dilemma of how to manage Graves' hyperthyroidism in patients with associated orbitopathy. The Journal of clinical endocrinology and metabolism, 96(3), pp. 592-9.

Brüser, A. et al., 2016. The Activation Mechanism of Glycoprotein Hormone Receptors with Implications in the Cause and Therapy of Endocrine Diseases. Journal of Biological Chemistry, 291(2), pp. 508-520.

Burton, B. R. et al., 2014. Sequential transcriptional changes dictate safe and effective antigen-specific immunotherapy. Nature Communications, 5, p. 4741.

Eckstein, A., Schittkowski, M. & Esser, J., 2012. Surgical treatment of Graves' ophthalmopathy. Best practice & research. Clinical endocrinology & metabolism, 26(3), pp. 339-58.

Gloriam, D. E. et al., 2009. Definition of the G protein-coupled receptor transmembrane bundle binding pocket and calculation of receptor similarities for drug design. Journal of medicinal chemistry, 52(14), pp. 4429-42.

Grzesik, P. et al., 2014. Differences between lutropin-mediated and choriogonadotropin-mediated receptor activation. The FEBS journal, 281(5), pp. 1479-92.

Haas, A.-K. et al., 2011. Mutations that silence constitutive signaling activity in the allosteric ligand-binding site of the thyrotropin receptor. Cellular and Molecular Life Sciences, 68(1), pp. 159-167.

Jäschke, H. et al., 2006. A low molecular weight agonist signals by binding to the transmembrane domain of thyroid-stimulating hormone receptor (TSHR) and luteinizing hormone/chorionic gonadotropin receptor (LHCGR). The Journal of biological chemistry, 281(15), pp. 9841-4.

Jiang, X. et al., 2012. Structure of follicle-stimulating hormone in complex with the entire ectodomain of its receptor. Proceedings of the National Academy of Sciences of the United States of America, 109(31), pp. 12491-6.

Kleinau, G., Mueller, S., et al., 2011. Defining structural and functional dimensions of the extracellular thyrotropin receptor region. The Journal of biological chemistry, 286(25), pp. 22622-31.

Kleinau, G. et al., 2008. Evidence for cooperative signal triggering at the extracellular loops of the TSH receptor. FASEB journal: official publication of the Federation of American Societies for Experimental Biology, 22(8), pp. 2798-808.

Kleinau, G. et al., 2008. Molecular and structural effects of inverse agonistic mutations on signaling of the thyrotropin receptor—a basally active GPCR. Cellular and molecular life sciences: CMLS, 65(22), pp. 3664-76.

Kleinau, G. et al., 2010. Signaling-sensitive amino acids surround the allosteric ligand binding site of the thyrotropin receptor. The FASEB Journal, 24(7), pp. 2347-2354.

Kleinau, G. & Krause, G., 2009. Thyrotropin and homologous glycoprotein hormone receptors: structural and functional aspects of extracellular signaling mechanisms. Endocrine reviews, 30(2), pp. 133-51.

Van Koppen, C. J. et al., 2012. Mechanism of action of a nanomolar potent, allosteric antagonist of the thyroid-stimulating hormone receptor. British journal of pharmacology, 165(7), pp. 2314-24.

Krause, G., Kreuchwig, A. & Kleinau, G., 2012. Extended and structurally supported insights into extracellular hormone binding, signal transduction and organization of the thyrotropin receptor. PloS one, 7(12), p.e52920.

Kreuchwig, A. et al., 2011. Research resource: Update and extension of a glycoprotein hormone receptors web application. Molecular endocrinology (Baltimore, Md.), 25(4), pp. 707-12.

M C. Gershengorn, S. Neumann, B. C. Raaka, C. Thomas, J. Inglese, J. Southal, S. Titus, W. Zheng, W. Huang, G. Krause, G. K., 2014. LOW MOLECULAR WEIGHT THYROID STIMULATING HORMONE RECEPTOR (TSHR) AGONISTS.

Neumann, S. et al., 2014. A selective TSH receptor antagonist inhibits stimulation of thyroid function in female mice. Endocrinology, 155(1), pp. 310-4.

Neumann, S. et al., 2010. A small molecule inverse agonist for the human thyroid-stimulating hormone receptor. Endocrinology, 151(7), pp. 3454-9.

Neumann, S. et al., 2009. Small-molecule agonists for the thyrotropin receptor stimulate thyroid function in human thyrocytes and mice. Proceedings of the National Academy of Sciences of the United States of America, 106(30), pp. 12471-6.

Sato, S. et al., 2014. Comparison of Efficacy and Adverse Effects Between Methimazole 15 mg+Inorganic Iodine 38 mg/Day and Methimazole 30 mg/Day as Initial Therapy for Graves' Disease Patients with Moderate to Severe Hyperthyroidism. Thyroid: official journal of the American Thyroid Association.

Sorisky, A. et al., 1996. Evidence of adipocyte differentiation in human orbital fibroblasts in primary culture. The Journal of clinical endocrinology and metabolism, 81(9), pp. 3428-31.

Van Straten, N. C. R. et al., 2005. Identification of substituted 6-amino-4-phenyltetrahydroquinoline derivatives: potent antagonists for the follicle-stimulating hormone receptor. Journal of medicinal chemistry, 48(6), pp. 1697-700.

Van Straten, N. C. R. et al., 2002. The first orally active low molecular weight agonists for the LH receptor: thienopyr(im)idines with therapeutic potential for ovulation induction. Chembiochem: a European journal of chemical biology, 3(10), pp. 1023-6.

Titus, S. et al., 2008. Quantitative high-throughput screening using a live-cell cAMP assay identifies small-molecule agonists of the TSH receptor. Journal of biomolecular screening, 13(2), pp. 120-7.

Turcu, A. F. et al., 2013. A small molecule antagonist inhibits thyrotropin receptor antibody-induced orbital fibroblast functions involved in the pathogenesis of Graves ophthalmopathy. The Journal of clinical endocrinology and metabolism, 98(5), pp. 2153-9.

Vlaeminck-Guillem, V. et al., 2002. Activation of the cAMP pathway by the TSH receptor involves switching of the ectodomain from a tethered inverse agonist to an agonist. Molecular endocrinology (Baltimore, Md.), 16(4), pp. 736-46.

Worth, C. L. et al., 2011. GPCR-SSFE: a comprehensive database of G-protein-coupled receptor template predictions and homology models. BMC bioinformatics, 12, p. 185.

Worth, C. L., Kleinau, G. & Krause, G., 2009. Comparative sequence and structural analyses of G-protein-coupled receptor crystal structures and implications for molecular models. PloS Zhang, D. et al., 2015. Two disparate ligand-binding sites in the human P2Y1 receptor. Nature. Available at: http://www.nature.com/doifinder/10.1038/nature14287.

Zhang, K. et al., 2014. Structure of the human P2Y12 receptor in complex with an antithrombotic drug. Nature, 509(7498), pp. 115-118.

Atamanyuk et al. 2008, Journal of Sulfur Chemistry, 29:2, p 151-162.

Lesyk et al. 2011, Biopolimery I Kletka, 27:2, p 107-111.

Holthoff et al. Prolonged TSH Receptor A Subunit Immunization of Female Mice Leads to a Long-Term Model of Graves' Disease, Tachycardia, and Cardiac Hypertrophy. Endocrinology 2015; 156: 1577-89.

Banga J et al. Modeling Graves' Orbitopathy in Experimental Graves' Disease. Horm Metab Res 2015; 47: 797-803.

The invention claimed is:

1. A method of treating hyperthyroidism in a subject, the method comprising administering to said subject a compound according to Formula I:

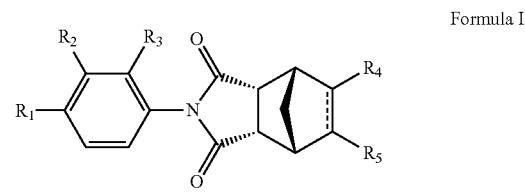

Formula I wherein $R_1$=H, OH, alkyl, alkoxy, carbonyl, alkoxycarbonyl, $NH_2$, halogen, an optionally substituted 6-member ring, wherein said optional substituent is selected from the group consisting of OH, alkyl, alkoxy, carbonyl, alkoxycarbonyl, $NO_2$, amine, halogen, $CX_3$, wherein X is a halogen, or wherein $R_1 = $ 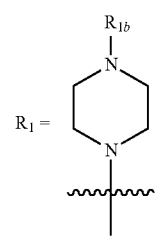

wherein $R_{1b}$=alkyl, an optionally substituted 6-member ring, wherein said optional substituent is selected from the group consisting of OH, alkyl, alkoxy, carbonyl, alkoxycarbonyl, NO2, amine, halogen, $CX_3$, wherein X is a halogen;

$R_2$=H, OH, alkyl, alkoxy, carbonyl, alkoxycarbonyl, $NO_2$, amine, aminocarbonyl;

$R_3$=H, OH, alkyl, alkoxy, carbonyl, alkoxycarbonyl, halogen;

$R_4$, $R_5$=alkyl, alkoxy, alkoxycarbonyl, wherein $R_4$ and $R_5$ can be the same or different, or wherein
R₄ and R₅=

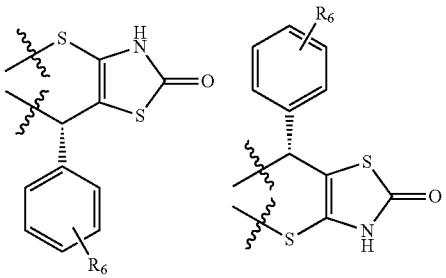

wherein R₆=H, OH, alkyl, alkoxy, carbonyl, alkoxy-carbonyl, NO₂, amine, aminocarbonyl, halogen, CX₃, wherein X is a halogen.

2. The method according to claim 1
wherein R₁ to R₃ are as in claim 1,
wherein R₄ and R₅=

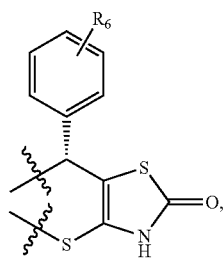

and
wherein R₆=H, OH, alkyl, alkoxy, carbonyl, alkoxycarbonyl, NO₂, amine, aminocarbonyl, halogen, CX₃, wherein X is a halogen.

3. The method according to claim 1
wherein
R₁=H, OH, alkyl, O-alkyl, CO-alkyl, C(O)O-alkyl, NH₂, halogen, an optionally substituted 6-member ring, wherein said optional substituent is selected from the group consisting of OH, alkyl, O-alkyl, CO-alkyl, C(O)O-alkyl, NO₂, NH₂, halogen, CX₃, wherein X is halogen,
or wherein

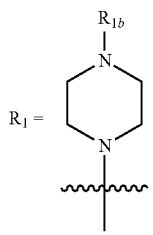

wherein R₁ᵦ=alkyl, an optionally substituted 6-member ring, wherein said optional substituent is selected from the group consisting of OH, alkyl, O-alkyl, CO-alkyl, C(O)O-alkyl, NO₂, NH₂, halogen, CX₃, wherein X is a halogen;
R₂=H, OH, alkyl, O-alkyl, CO-alkyl, C(O)O-alkyl, NO₂, NH₂, NHR₂ₐ, NHR₂ₐR₂ᵦ, NHCOR₂꜀, wherein R₂ₐ, R₂ᵦ, R₂꜀ is alkyl;

R₃=H, OH, alkyl, O-alkyl, C(O)O-alkyl, halogen;
R₄, R₅=alkyl, wherein R₄ and R₅ can be the same or different, or wherein
R₄ and R₅= wherein R₆=H, OH, alkyl, O-alkyl, CO-alkyl, C(O)O-alkyl, NO₂, NH₂, NHR₂ₐ, NHR₂ₐR₂ᵦ, NHCOR₂꜀, wherein R₂ₐ, R₂ᵦ, R₂꜀ is alkyl, X, CX₃, wherein X is a halogen;
and wherein any one or more of said alkyl groups is straight-chained or branched.

4. The method according to claim 3
wherein R₁ to R₃ are as in claim 3,
and wherein R₄ and R₅= and
wherein R₆=H, OH, alkyl, O-alkyl, CO-alkyl, C(O)O-alkyl, NO₂, NH₂, NHR₂ₐ, NHR₂ₐR₂ᵦ, NHCOR₂꜀, wherein R₂ₐ, R₂ᵦ, R₂꜀ is alkyl, X, CX₃, wherein X is a halogen;
and wherein any one or more of said alkyl groups is straight-chained or branched.

5. The method according to claim 1, wherein the compound according to formula I is a compound according to Formula II:

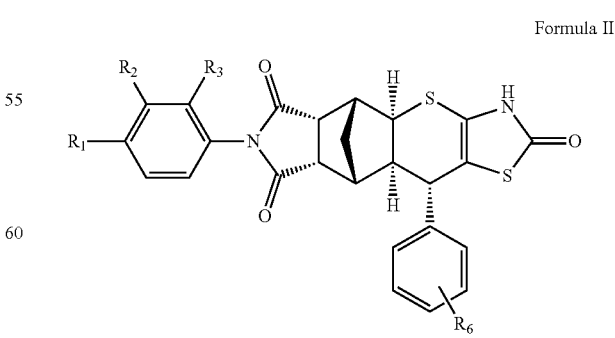

Formula II and/or enantiomers of structures according to Formula II, wherein

R=H, OH, alkyl, alkoxy, carbonyl, alkoxycarbonyl, NH$_2$, halogen, an optionally substituted 6-member ring, wherein said optional substituent is selected from the group consisting of OH, alkyl, alkoxy, carbonyl, alkoxycarbonyl, NO$_2$, amine, halogen, CX$_3$, wherein X is a halogen, or wherein

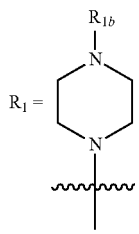

wherein R$_{1b}$=alkyl, an optionally substituted 6-member ring, wherein said optional substituent is selected from the group consisting of OH, alkyl, alkoxy, carbonyl, alkoxycarbonyl, NO$_2$, amine, halogen, CX$_3$, wherein X is a halogen;
R$_2$=H, OH, alkyl, alkoxy, carbonyl, alkoxycarbonyl, NO$_2$, amine, aminocarbonyl;
R$_3$=H, OH, alkyl, alkoxy, carbonyl, alkoxycarbonyl, halogen;
R$_6$=H, OH, alkyl, alkoxy, carbonyl, alkoxycarbonyl, NO$_2$, amine, aminocarbonyl, halogen, CX$_3$, wherein X is a halogen.

6. The method according to claim 1, wherein the compound according to Formula I is a compound according to Formula III:

Formula III

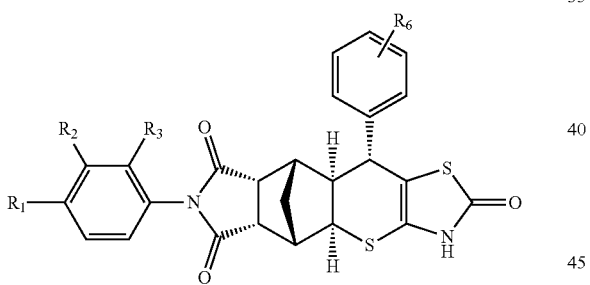

Formula III
wherein
R$_1$=H, OH, alkyl, alkoxy, carbonyl, alkoxycarbonyl, NH$_2$, halogen, an optionally substituted 6-member ring, wherein said optional substituent is selected from the group consisting of OH, alkyl, alkoxy, carbonyl, alkoxycarbonyl, NO$_2$, amine, halogen, CX$_3$, wherein X is a halogen,
or wherein

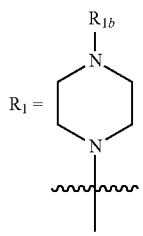

wherein R$_{1b}$=alkyl, an optionally substituted 6-member ring, wherein said optional substituent is selected from the group consisting of OH, alkyl, alkoxy, carbonyl, alkoxycarbonyl, NO$_2$, amine, halogen, CX$_3$, wherein X is a halogen;
R$_2$=H, OH, alkyl, alkoxy, carbonyl, alkoxycarbonyl, NO$_2$, amine, aminocarbonyl;
R$_3$=H, OH, alkyl, alkoxy, carbonyl, alkoxycarbonyl, halogen;
R$_6$=H, OH, alkyl, alkoxy, carbonyl, alkoxycarbonyl, NO$_2$, amine, aminocarbonyl, halogen, CX$_3$, wherein X is a halogen.

7. The method according to claim 1, wherein the compound according to Formula I is a compound according to Formula II Formula II

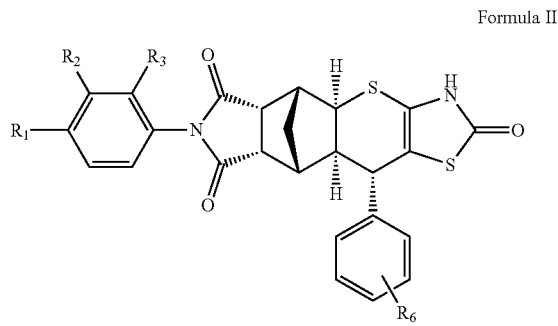

and/or enantiomers of structures according to Formula II, wherein
R$_1$=H, OH, alkyl, O-alkyl, CO-alkyl, C(O)O-alkyl, NH$_2$, halogen, an optionally substituted 6-member ring, wherein said optional substituent is selected from the group consisting of OH, alkyl, O-alkyl, CO-alkyl, C(O)O-alkyl, NO$_2$, NH$_2$, halogen, CX$_3$, wherein X is halogen,
or wherein

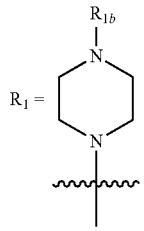

wherein R$_{1b}$=alkyl, an optionally substituted 6-member ring, wherein said optional substituent is selected from the group consisting of OH, alkyl, O-alkyl, CO-alkyl, C(O)O-alkyl, NO$_2$, NH$_2$, halogen, CX$_3$, wherein X is a halogen;
R$_2$=H, OH, alkyl, O-alkyl, CO-alkyl, C(O)O-alkyl, NO$_2$, NH$_2$, NHR$_{2a}$, NHR$_{2a}$R$_{2b}$, NHCOR$_{2c}$, wherein R$_{2a}$, R$_{2b}$, R$_{2c}$ is alkyl;
R$_3$=H, OH, alkyl, O-alkyl, C(O)O-alkyl, halogen;
R$_6$=H, OH, alkyl, O-alkyl, CO-alkyl, C(O)O-alkyl, NO$_2$, NH$_2$, NHR$_{2a}$, NHR$_{2a}$R$_{2b}$, NHCOR$_{2c}$, wherein R$_{2a}$, R$_{2b}$, R$_{2c}$ is alkyl, halogen, CX$_3$, wherein X is a halogen;
and wherein any one or more of said alkyl groups is straight-chained or branched.

8. The method according to claim 1, wherein the compound according to Formula I is a compound according to Formula III:

Formula III

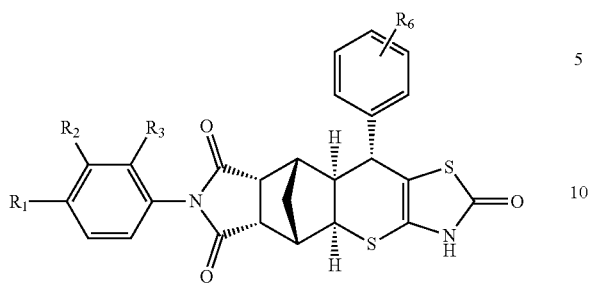

wherein
R₁=H, OH, alkyl, O-alkyl, CO-alkyl, C(O)O-alkyl, NH₂, halogen, an optionally substituted 6-member ring, wherein said optional substituent is selected from the group consisting of OH, alkyl, O-alkyl, CO-alkyl, C(O)O-alkyl, NO₂, NH₂, halogen, CX₃, wherein X is halogen,
or wherein

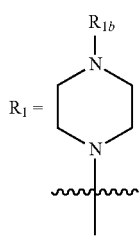

wherein R₁ₐ=alkyl, an optionally substituted 6-member ring, wherein said optional substituent is selected from the group consisting of OH, alkyl, O-alkyl, CO-alkyl, C(O)O-alkyl, NO₂, NH₂, halogen, CX₃, wherein X is a halogen;
R₂=H, OH, alkyl, O-alkyl, CO-alkyl, C(O)O-alkyl, NO₂, NH₂, NHR₂ₐ, NHR₂ₐR₂ᵦ, NHCOR₂𝒸, wherein R₂ₐ, R₂ᵦ, R₂𝒸 is alkyl;
R₃=H, OH, alkyl, O-alkyl, C(O)O-alkyl, halogen;
R₆=H, OH, alkyl, O-alkyl, CO-alkyl, C(O)O-alkyl, NO₂, NH₂, NHR₂ₐ, NHR₂ₐR₂ᵦ, NHCOR₂𝒸, wherein R₂ₐ, R₂ᵦ, R₂𝒸 is alkyl, halogen, CX₃, wherein X is a halogen;
and wherein any one or more of said alkyl groups is straight-chained or branched.

9. The method according to claim 1, wherein

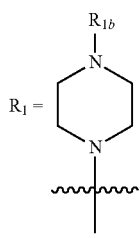

wherein R₁ᵦ=alkyl, an optionally substituted 6-member ring, wherein said optional substituent is selected from the group consisting of OH, alkyl, alkoxy, carbonyl, alkoxycarbonyl, NO₂, amine, halogen, CX₃, wherein X is a halogen;
R₂=H, OH, alkyl, alkoxy, carbonyl, alkoxycarbonyl, NO₂, amine, aminocarbonyl;
R₃=H, OH, alkyl, alkoxy, carbonyl, alkoxycarbonyl, halogen;
R₄, R₅=alkyl, alkoxy, alkoxycarbonyl.

10. The method according to claim 1, wherein

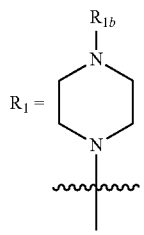

wherein R₁ᵦ=alkyl, an optionally substituted 6-member ring, wherein said optional substituent is selected from the group consisting of OH, alkyl, O-alkyl, CO-alkyl, C(O)O-alkyl, NO₂, NH₂, halogen, CX₃, wherein X is a halogen;
R₂=H, OH, alkyl, O-alkyl, CO-alkyl, C(O)O-alkyl, NO₂, NH₂, NHR₂ₐ, NHR₂ₐR₂ᵦ, NHCOR₂𝒸, wherein R₂ₐ, R₂ᵦ, R₂𝒸 is alkyl;
R₃=H, OH, alkyl, O-alkyl, C(O)O-alkyl, halogen;
R₄, R₅=alkyl;
and wherein any one or more of said alkyl groups is straight-chained or branched.

11. The method according to claim 1, wherein
R₁=H, OH, Me, O-Me, CO-Me, C(O)O-Me, NH₂, halogen, phenyl, or substituted phenyl comprising a C(O)O-Me group,
or wherein

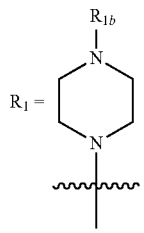

wherein R₁ᵦ=Me, phenyl;
R₂=H, Me, NO₂, NH₂;
R₃=H, OH, Me, O-Me, C(O)O-Me;
R₆=H, OH, Me, O-Me, CO-Me, C(O)O-Me, N(CH₃)₂, F, CF₃.

12. The method according to claim 1, wherein

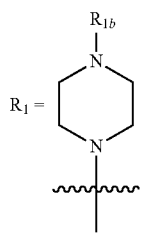

wherein R$_{1b}$=Me, C(O)O(CH$_2$)$_2$CH$_3$, phenyl, or substituted phenyl comprising a CF$_3$ group;
R$_2$=H, Me, NO$_2$, NH$_2$;
R$_3$=H, OH, Me, O-Me, C(O)O-Me.
13. The method according to claim 1, wherein the compound is
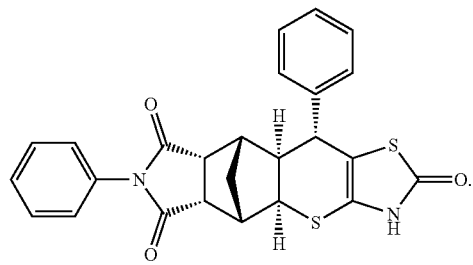 [SMILES: O=C1[C@@H]2[C@H]3C[C@H]([C@@H]4Sc5[nH]c(=O)sc5[C@@H](c5ccccc5)[C@H]34)[C@@H]2C(=O)N1c1ccccc1]
14. The method according to claim 1, wherein the compound is
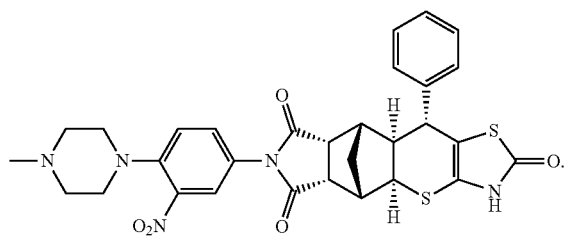 [SMILES: CN1CCN(c2ccc(N3C(=O)[C@@H]4[C@H]5C[C@H]([C@@H]6Sc7[nH]c(=O)sc7[C@@H](c7ccccc7)[C@H]56)[C@@H]4C3=O)cc2[N+](=O)[O-])CC1]
15. The method according to claim 1, wherein the compound is selected from the group consisting of:
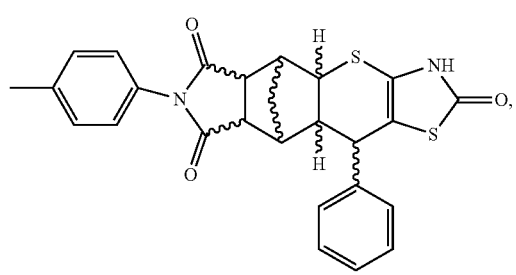
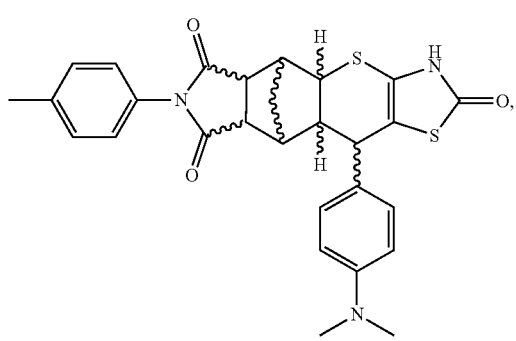
-continued
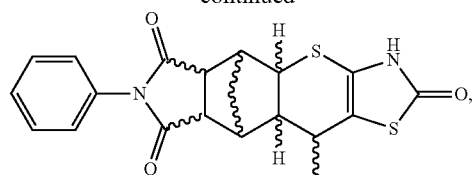
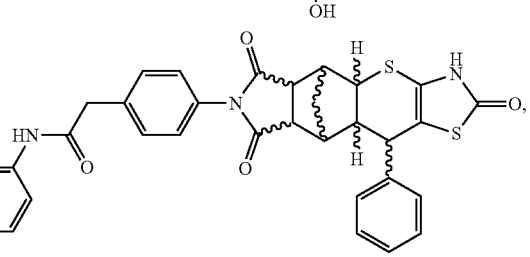
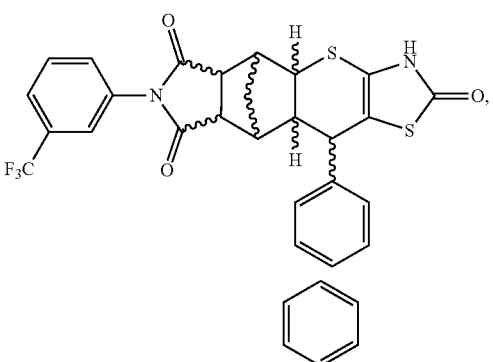
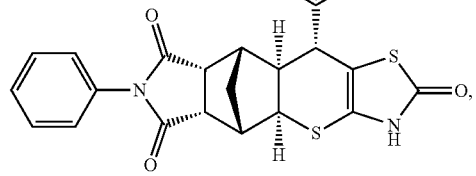
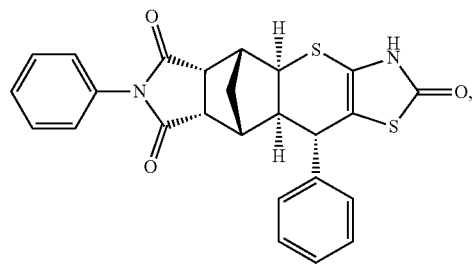
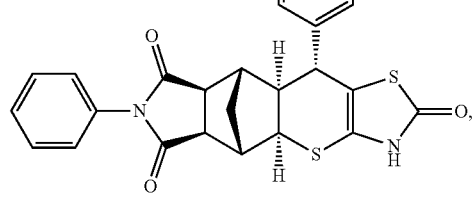

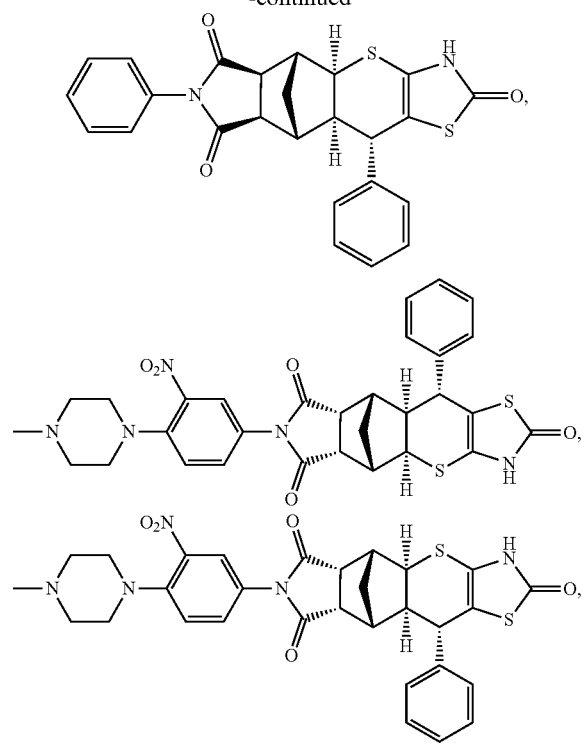
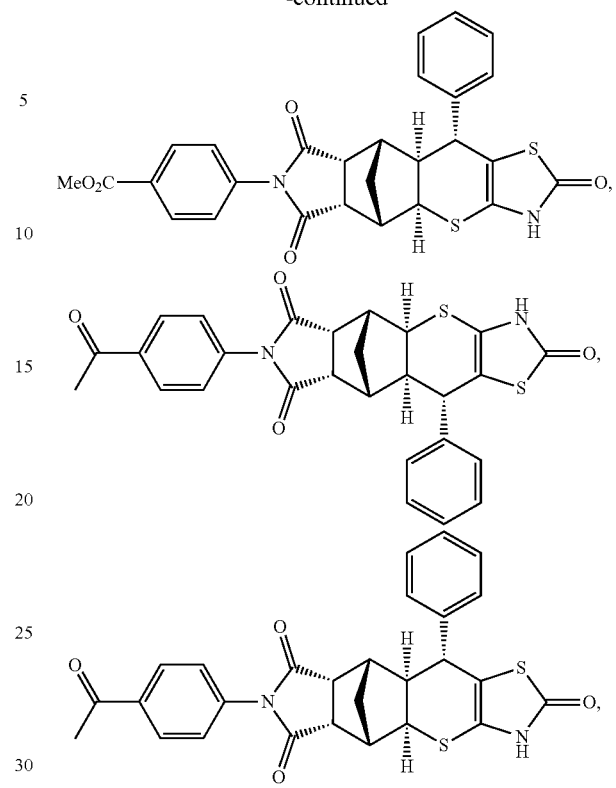
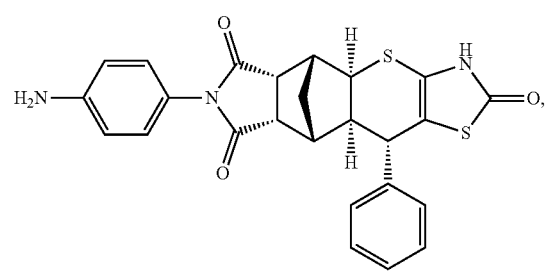
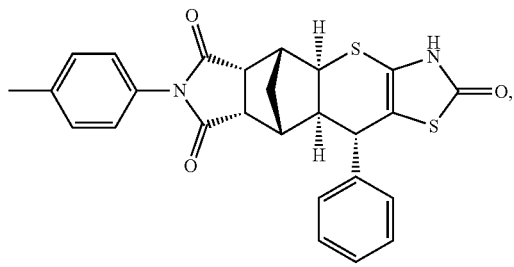
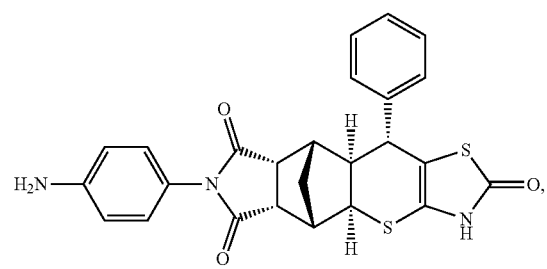
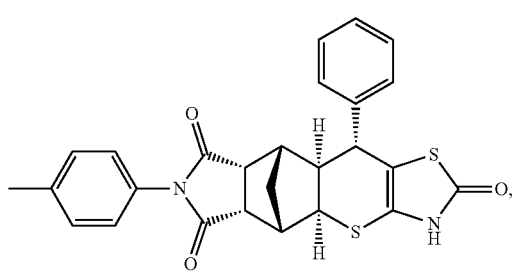
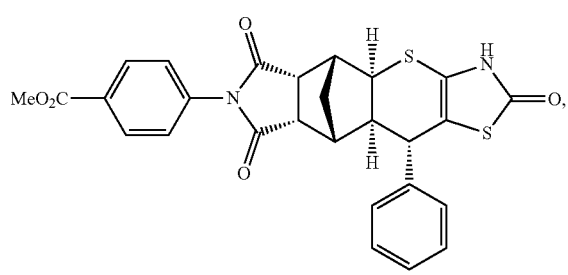
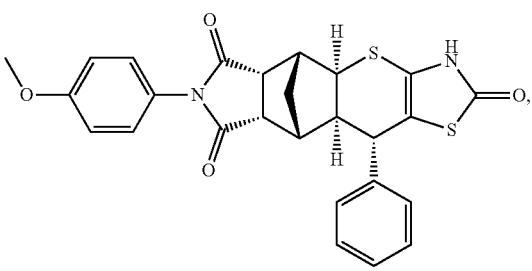

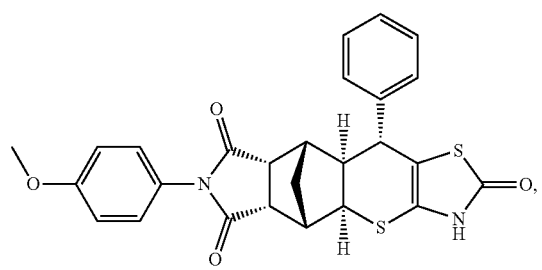
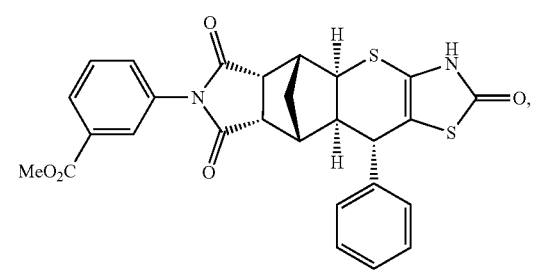
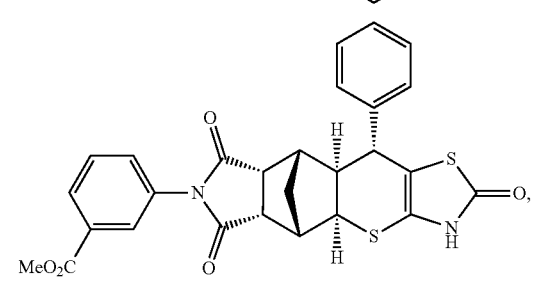
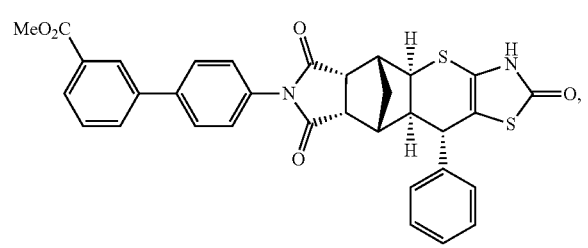
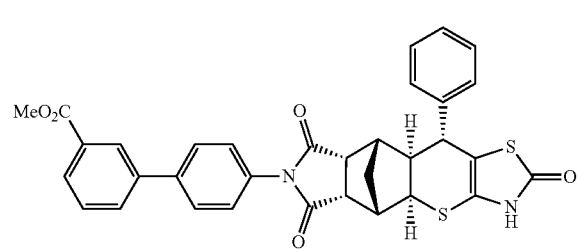
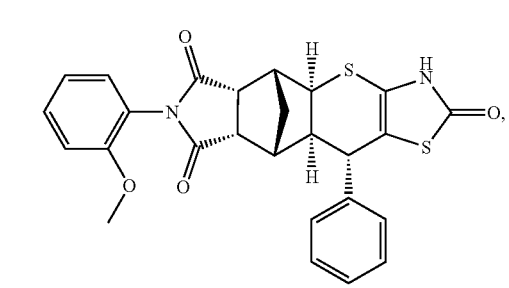
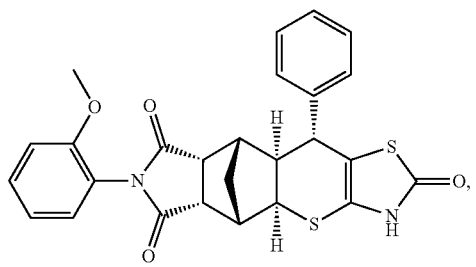
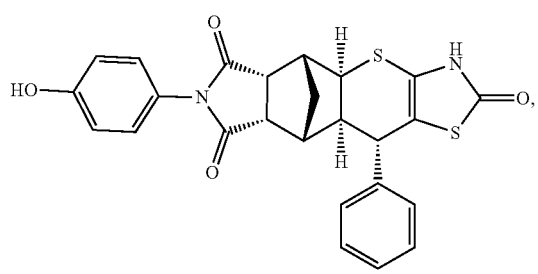
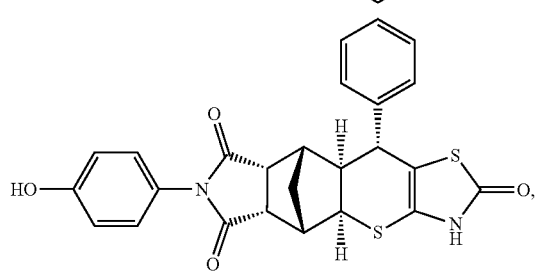
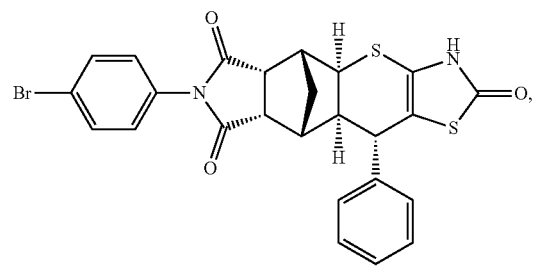
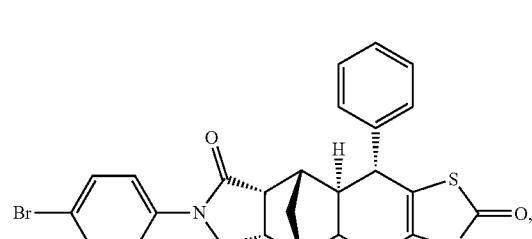
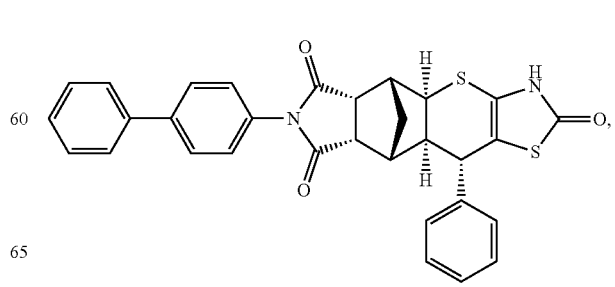

-continued
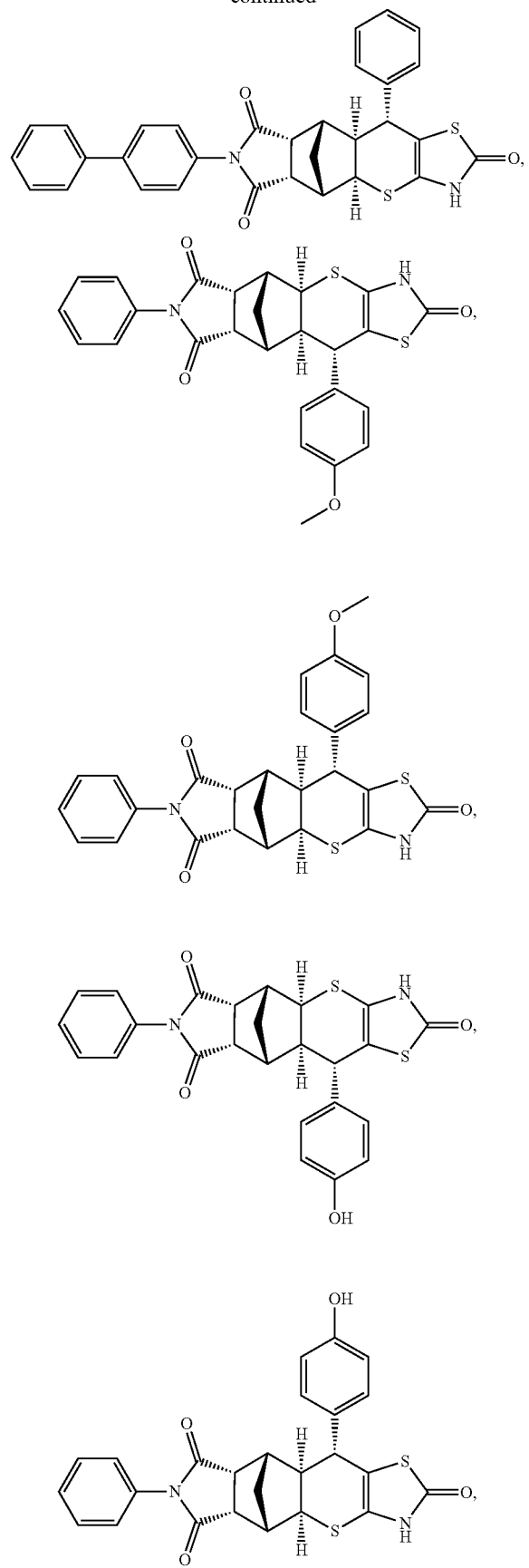
-continued
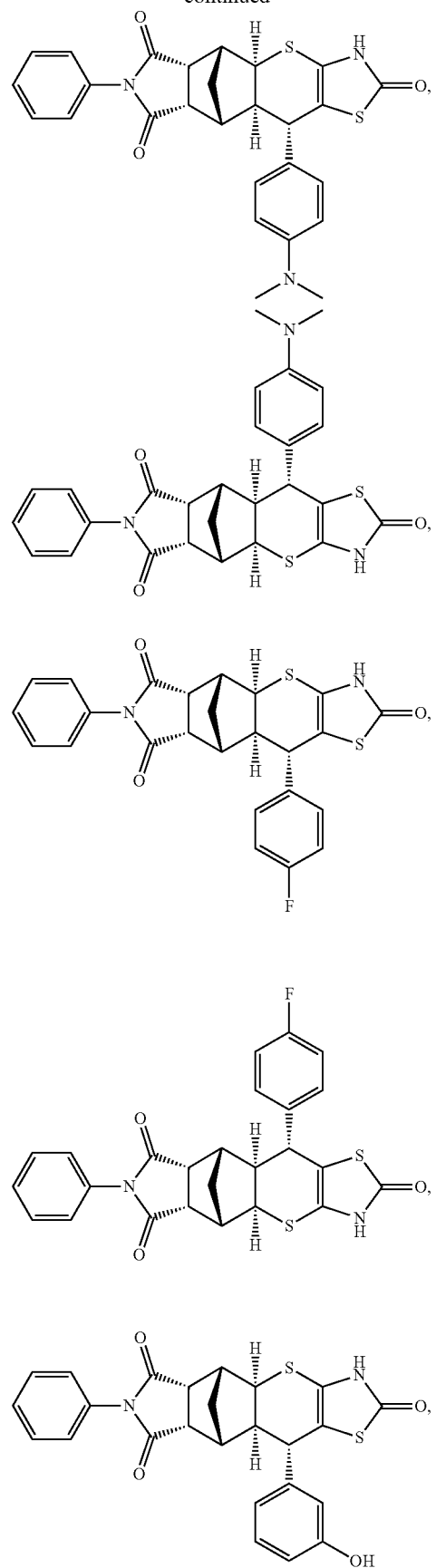

-continued
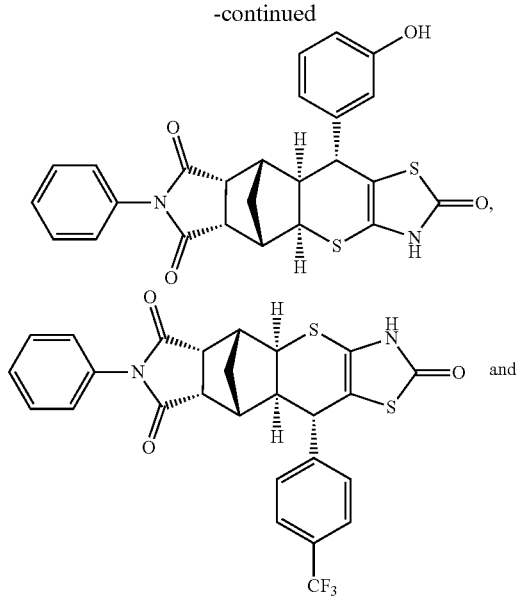
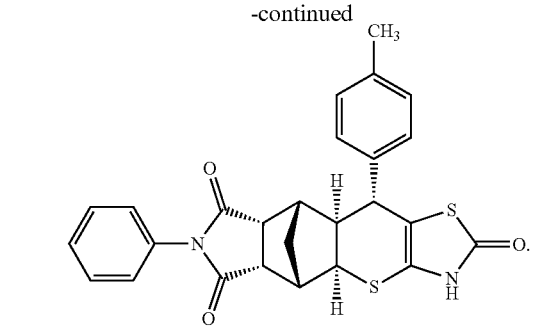
16. The method according to claim 1, wherein the hyperthyroidism is Graves' disease.
17. The method according to claim 1, wherein the hyperthyroidism is Graves' ophthalmopathy.
18. The method according to claim 1, wherein the hyperthyroidism is Graves' dermopathy.
19. The method according to claim 1, wherein the hyperthyroidism is thyroid cancer.
* * * * *